US008030060B2

(12) United States Patent
Guo

(10) Patent No.: US 8,030,060 B2
(45) Date of Patent: Oct. 4, 2011

(54) GENE SIGNATURE FOR DIAGNOSIS AND PROGNOSIS OF BREAST CANCER AND OVARIAN CANCER

(75) Inventor: Nancy Lan Guo, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 392 days.

(21) Appl. No.: 12/077,992

(22) Filed: Mar. 24, 2008

(65) Prior Publication Data
US 2009/0197259 A1 Aug. 6, 2009

Related U.S. Application Data

(60) Provisional application No. 60/919,369, filed on Mar. 22, 2007.

(51) Int. Cl.
| | |
|---|---|
| C12M 3/00 | (2006.01) |
| C12M 1/34 | (2006.01) |
| C12Q 1/68 | (2006.01) |
| C07H 21/02 | (2006.01) |
| C07H 21/04 | (2006.01) |

(52) U.S. Cl. .................. 435/287.2; 536/23.1; 536/24.3; 435/6

(58) Field of Classification Search ........................ None
See application file for complete search history.

(56) References Cited

U.S. PATENT DOCUMENTS

| | | | |
|---|---|---|---|
| 6,974,667 B2 | 12/2005 | Horne | |
| 7,056,674 B2 | 6/2006 | Baker | |
| 2003/0224374 A1 | 12/2003 | Dai | |

OTHER PUBLICATIONS

Richer et al. (The Journal of Biological Chemistry 2002 vol. 277 p. 5209).*
Map2k2 probe Affymetrix 6800 Microarray www.affymetrix.com.*
Smarcd2 probe Affymetrix 6800 Microarray www.affymetrix.com.*
S100P probe Affymetrix 6800 Microarray www.affymetrix.com.*
FAT probe Affymetrix 6800 Microarray www.affymetrix.com.*
DDOST probe Affymetrix 6800 Microarray www.affymetrix.com.*
SSBP1 probe Affymetrix 6800 Microarray www.affymetrix.com.*
PDGFRA probe Affymetrix 6800 Microarray www.affymetrix.com.*
INPPL1 probe Affymetrix 6800 Microarray www.affymetrix.com.*
RAD50 probe Affymetrix 6800 Microarray www.affymetrix.com.*
PLSCR1 probe Affymetrix 6800 Microarray www.affymetrix.com.*
RAD52 probe Affymetrix 6800 Microarray www.affymetrix.com.*
C18B11 probe Affymetrix 6800 Microarray www.affymetrix.com.*
MCM2 probe Affymetrix 6800 Microarray www.affymetrix.com.*
MCF2L probe Affymetrix 6800 Microarray www.affymetrix.com.*
TXNRD1 probe Affymetrix 6800 Microarray www.affymetrix.com.*

* cited by examiner

*Primary Examiner* — Katherine Salmon
(74) *Attorney, Agent, or Firm* — William Aylor

(57) ABSTRACT

A first embodiment is a breast cancer prognosticator comprising a detection mechanism consisting a 15-gene signature. In addition there are embodiments comprised of 23-gene signatures and 28-gene signatures. The 28-gene signature may also be used for the prognosis of ovarian cancer. A second embodiment is a method to determine metastatic potential, relapse potential, or both in breast cancer patients comprising collecting a sample from an individual, removing marker-derived polynucleotide from said sample, using a detection mechanism to search for positive matches of said polynucleotides and either the 15, 23, or 28-gene signatures, and developing a quantitative expression profile. Utilizing risk analysis the individual can be placed into one of two or more groups predicting risk and/or clincopathogic variables. Another embodiment is a method to determine relapse free potential in breast cancer patients comprising collecting a sample from an individual, removing marker-derived polynucleotide from said sample, using a detection mechanism to search for positive matches of said polynucleotides and a 24-gene signature, and developing a quantitative expression profile.

2 Claims, 10 Drawing Sheets

GENE SIGNATURE FOR DIAGNOSIS AND PROGNOSIS OF BREAST CANCER AND OVARIAN CANCER

CROSS-REFERENCE TO RELATED APPLICATIONS

This application claims priority of U.S. provisional patent application numbered 60/919,369 filed on the date Mar. 22, 2007.

REFERENCE TO SEQUENCE LISTING, A TABLE, OR A COMPUTER PROGRAM LISTING COMPACT DISC APPENDIX

This application contains a Sequence Listing submitted on compact disk containing file name 387.5 eq. The sequence listing on the compact disc is incorporated by reference herein in its entirety.

BRIEF DESCRIPTION OF THE SEVERAL VIEWS OF THE DRAWINGS

The following figures are not drawn to scale and are for illustrative purposes only.

FIG. 1 is a Time dependent ROC (t=5 years) curve of the 28-gene signature on the training set from Sotiriou et al. (8) The area under the ROC curve (AUC)=0.983.

FIG. 2 is a AUC in year 1 to year 11 during follow-up after surgery in the patient cohort from Sotiriou et al. (8).

FIG. 3 is a Time-dependent ROC (t=5 years) curves of the 28-gene signature on two validation sets. AUC=0.843 with 25 overlapping genes on data from van't Veer et al. (27) AUC=0.764 with 8 overlapping genes on data from Sorlie et al. (10).

FIG. 4 is a AUC in year 1 to year 13 during follow-up after surgery on two independent patient cohorts (10;28).

FIG. 5 is a Time-dependent ROC curves at time=5 years. AUC=0.927 on data from Sotiriou et al. (8) AUC=0.808 on data from Sorlie et al. (10)

FIG. 6 is the area under the ROC curve (AUC) of overall survival prediction during the follow-up after surgery.

FIG. 7 are Time-dependent ROC curves at time=5 years. AUC=0.92 on data from Sotiriou et al. (8)

FIG. 8 are Time-dependent ROC curves at time=5 years. AUC=0.87 on data from Sorlie et al. (10)

FIG. 9 are Time-dependent ROC curves at time=5 years. AUC=0.79 on data from van't Veer et al. (26).

DETAILED DESCRIPTION OF THE INVENTION

Figure 1:
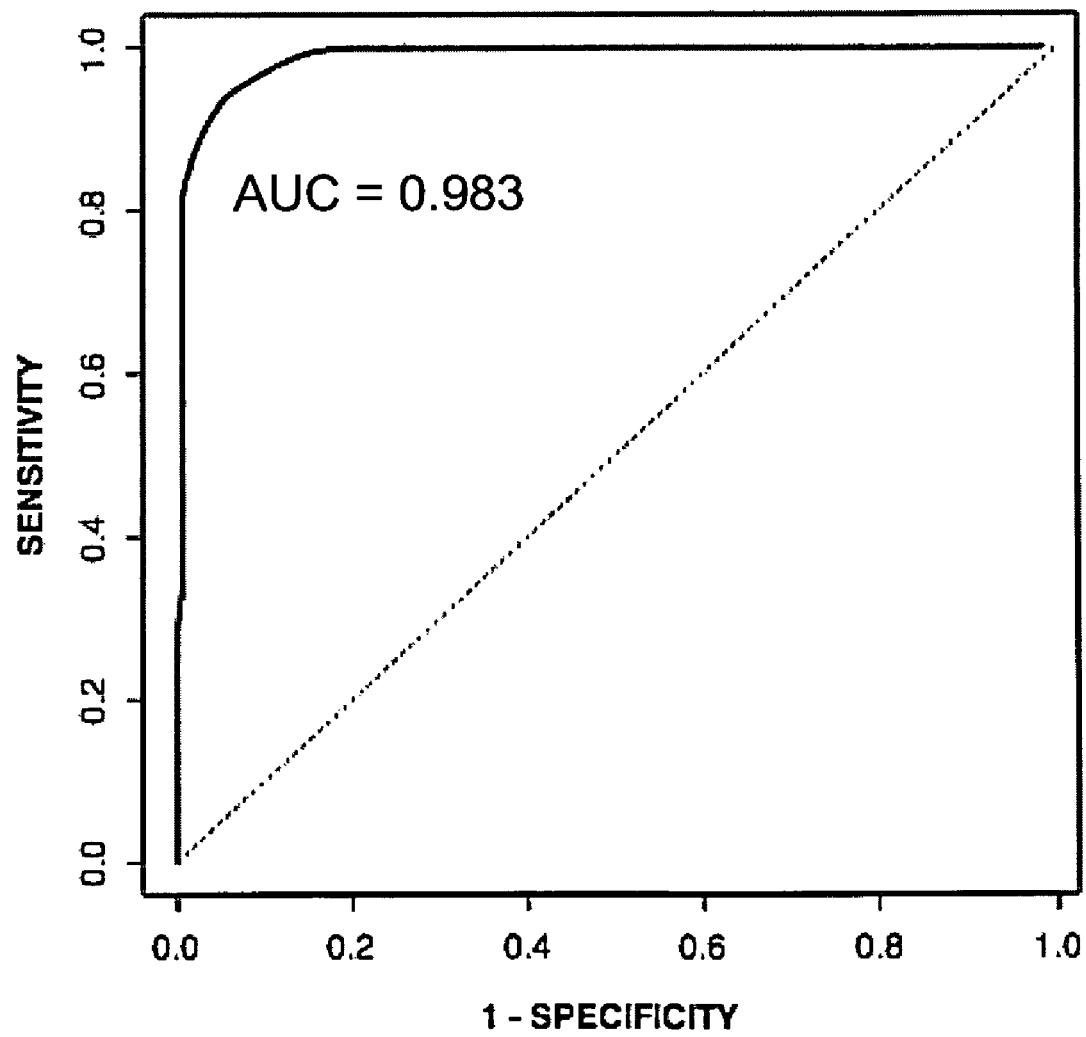
FIG. 1 is a Time dependent ROC analyses of the 28-gene signature in disease-free survival prediction in three breast cancer patient cohorts.

A first embodiment in this application can be an expression profile-defined prognostic model able to predict the recurrence and metastases of breast cancer and ovarian cancer by using unique gene expression patterns in tumors. Additionally, the expression profile-defined prognostic model may be used to predict the relapse-free interval and metastases-free interval. The expression based profile-defined prognostic model has been developed and is a highly accurate predictor of disease-free survival as well as overall survival in individual breast cancer patients. The expression based profile-defined prognostic model can be a gene signature such as a 15-gene signature, a 23-gene signature, or a 28-gene signature comprised of a combination of the following genes (Table 1).

TABLE 1

28 genes that quantifies disease-free survival and overall survival of breast cancer

| Gene | Clone_IMAGE | UniGene Cluster ID | Sequence ID | Seq. ID No |
|---|---|---|---|---|
| FAM134C | 198917 | Hs.463079 | NM_178126 | Seq. ID No 30 |
| TOMM70A | 198312 | Hs.227253 | NM_014820 | Seq. ID No 7 |
| MCF2 | 268412 | Hs.387262 | NM_001099855 | Seq. ID No 8 |
|  |  |  | NM_005369 | Seq. ID No 9 |
| RAD52 Pseudogene | 1377154 | Hs.552577 | NM_134424 | Seq. ID No 10 |
| MCM2 | 239799 | Hs.477481 | NM_004526 | Seq. ID No 11 |
| C18B11 | 131988 | Hs.173311 | NM_152260 | Seq. ID No 12 |
| SEC13L | 757210 | Hs.301048 | NM_031216 | Seq. ID No 13 |
|  |  |  | NM_001013437 | Seq. ID No 14 |
| SLC25A5 | 291660 | Hs.522767 | NM_001152 | Seq. ID No 15 |
| PLSCR1 | 268736 | Hs.130759 | NM_021105 | Seq. ID No 16 |
| TXNRD1 | 789376 | Hs.434367 | NM_003330 | Seq. ID No 17 |
|  |  |  | NM_001093771 | Seq. ID No 18 |
|  |  |  | NM_182742 | Seq. ID No 19 |
|  |  |  | NM_182729 | Seq. ID No 20 |
|  |  |  | NM_182743 | Seq. ID No 21 |
| RAD50 | 261828 | Hs.242635 | NM_005732 | Seq. ID No 22 |
|  |  |  | NM_133482 | Seq. ID No 23 |
| — | 46196 |  | BX100884 | Seq. ID No 4 |
|  |  |  | H09243 | Seq. ID No 5 |
|  |  |  | H09242 | Seq. ID No 6 |
| INPPL1 | 703964 | Hs.523875 | NM_001567 | Seq. ID No 24 |
| — | 501651 | Hs.439445 | AK025546 | Seq. ID No 3 |
| PBX2 | 80549 | Hs.509545 | NM_002586 | Seq. ID No 25 |
| SSBP1 | 125183 | Hs.490394 | NM_003143 | Seq. ID No 26 |
| — | 34396 | Hs.448229 | BE870371 | Seq. ID No 1 |
| PDGFRA | 376499 | Hs.74615 | NM_006206 | Seq. ID No 27 |
| ACOT4 | 488202 | Hs.49433 | NM_152331 | Seq. ID No 28 |
| DDOST | 50666 | Hs.523145 | NM_005216 | Seq. ID No 29 |
| IGHA1 | 182930 | Hs.497723 | AK128652 | Seq. ID No 30 |
| S100P | 135221 | Hs.2962 | NM_005980 | Seq. ID No 31 |
| FAT | 591266 | Hs.481371 | NM_005245 | Seq. ID No 32 |
| FGF2 | 324383 | Hs.284244 | NM_002006 | Seq. ID No 33 |
| INSM1 | 22895 | Hs.89584 | NM_002196 | Seq. ID No 34 |

TABLE 1-continued 28 genes that quantifies disease-free survival
and overall survival of breast cancer

| Gene | Clone_ IMAGE | UniGene Cluster ID | Sequence ID | Seq. ID No |
|---|---|---|---|---|
| IRF5 | 260035 | Hs.521181 | NM_001098629 | Seq. ID No 35 |
| | | | NM_002200 | Seq. ID No 36 |
| | | | NM_001098627 | Seq. ID No 37 |
| | | | NM_001098630 | Seq. ID No 38 |
| | | | NM_001098628 | Seq. ID No 39 |
| | | | NM_032643 | Seq. ID No 40 |
| | | | NM_001098631 | Seq. ID No 41 |
| SMARCD2 | 741067 | Hs.250581 | NM_001098426 | Seq. ID No 42 |
| | | | NM_003077 | Seq. ID No 43 |
| MAP2K2 | 769579 | Hs.465627 | NM_030662 | Seq. ID No 44 |

There is no overlap between the disclosed gene signature and previously reported gene signatures. Of the 28 genes in Table 1, 17 are related to tumorigenesis (Table 2) and 9 genes are linked to breast cancer pathogenesis (Table 3). Furthermore, among the nine breast cancer-related genes, five genes are established breast cancer biomarkers ((MCM2, Rad50, PDGFRA, S100P, and FGF2) (Table 3)).

TABLE 2

Genes that are related to tumorigenesis

| Gene | Gene Name | Function |
|---|---|---|
| MCF2 | Mcf.2 cell line derived transforming sequence | Guanine nucleotide exchange factor |
| MCM2 | Mcm2 minichromosome maintenance deficient 2, mitotin | DNA replication |
| SEC13L | Seh1-like | mRNA export, nuclear pore distribution and cell division |
| PLSCR1 | Phospholipid scramblase 1 | Lipid transfer signaling |
| RAD50 | RAD50 homolog | DNA repair |
| INPPL1 | Inositol polyphosphate phosphatase-like 1 | Lipid metabolism |
| TXNRD1 | Thioredoxin reductase 1 | Antioxidant and redox regulator |
| PBX2 | Pre-b-cell leukemia transcription factor 2 | Transcriptional repressor and tumor suppressor |
| SSBP1 | Single-stranded dna binding protein 1 | DNA binding protein |
| PDGFRA | Platelet-derived growth factor receptor | Growth factor receptor |
| S100P | S100 calcium binding protein p | Cell differentiation |
| FAT | Fat tumor suppressor homolog 1 | Cell signaling suppressor |
| FGF2 | Fibroblast growth factor 2 | Signaling tranduction |
| INSM1 | Insulinoma-associated 1 | Transcriptional repressor |
| IRF5 | Interferon regulatory factor 5 | Tumor suppressor gene |
| SMARCD2 | Swi/snf related, matrix associated, actin dependent regulator of chromatin, subfamily d, member 2 | chromatin remodelling |
| MAP2K2 | Mitogen-activated protein kinase kinase 2 | Signaling transduction |

TABLE 3

Genes that are linked to breast cancer pathogenesis

| Gene | Gene Name | Function | Breast Cancer Involvement |
|---|---|---|---|
| MCF2 | Mcf.2 cell line derived transforming sequence | Guanine nucleotide exchange factor | (+) |
| MCM2 | Mcm2 minichromosome maintenance deficient 2, mitotin | DNA replication | (+) biomarker (1) |
| RAD50 | | DNA repair | (+) biomarker (2) |
| TXNRD1 | Thioredoxin reductase 1 | Antioxidant and redox regulator | (+) |
| PDGFRA | Platelet-derived growth factor receptor | Growth factor receptor | (+) biomarker (3; 4) |
| S100P | S100 calcium binding protein p | Cell differentiation | (+) biomarker (5; 6) |
| FGF2 | Fibroblast growth factor 2 | Signaling tranduction | (+) biomarker (7) |
| SMARCD2 | Swi/snf related, matrix associated, actin dependent regulator of chromatin, subfamily d, member 2 | chromatin remodelling | (+) |
| MAP2K2 | Mitogen-activated protein kinase kinase 2 | Signaling transduction | (+) |

Figure 2:
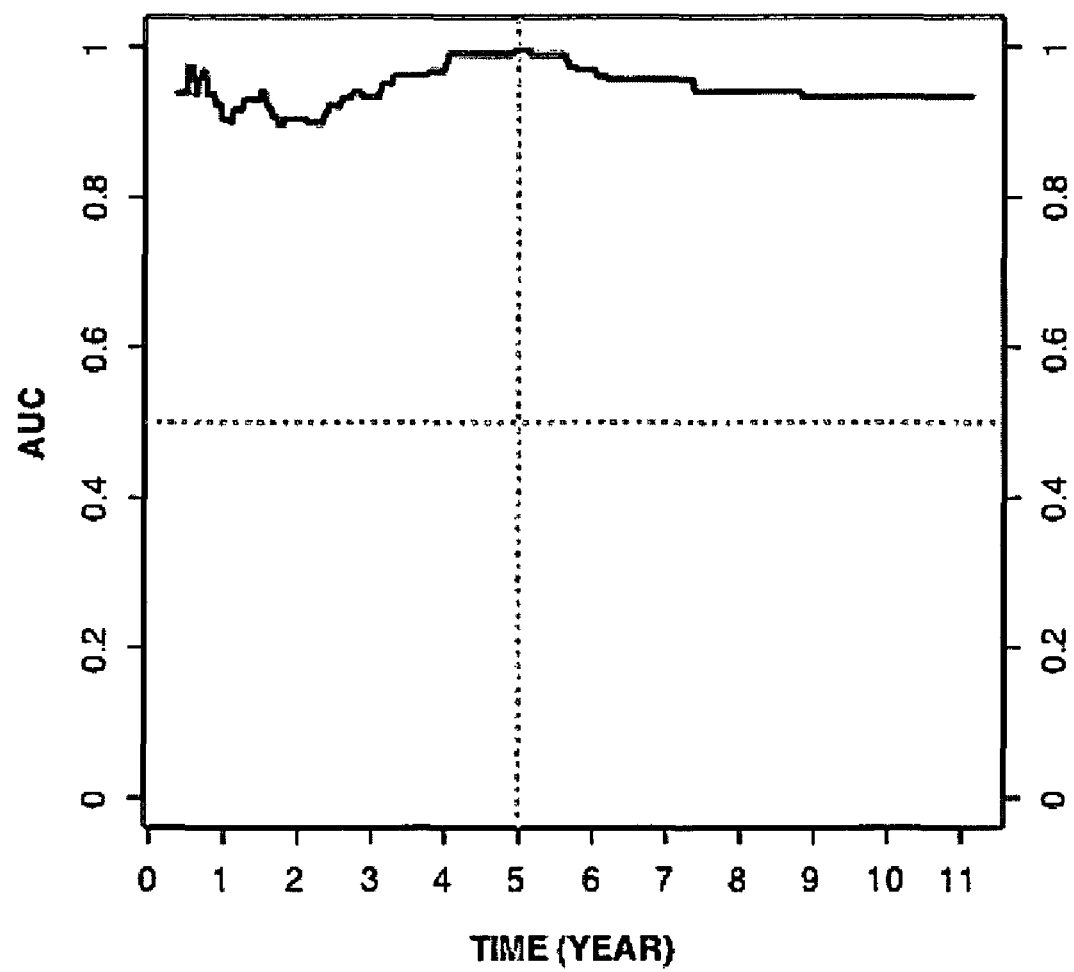
FIG. 2 is a Time dependent ROC analyses of the 28-gene signature in disease-free survival prediction in three breast cancer patient cohorts.

Based upon the expression profiles of these 28 genes in the data from Sotiriou et al. (8), a Linear Discriminant Analysis function classified 5-year relapse status for patients provided an accuracy of 0.92, a sensitivity of 0.90, and a specificity of 0.95. To evaluate relapse-free survival prediction, a Cox proportional hazards model was built on the 28-gene signature and the risk score was used to construct the time-dependent receiver operating curve (ROC). The area under the ROC curve (AUC) during year five was 0.983 (FIG. 1), and remained 0.92 between years 8 and 11 during the follow up (FIG. 2).

Figure 3:
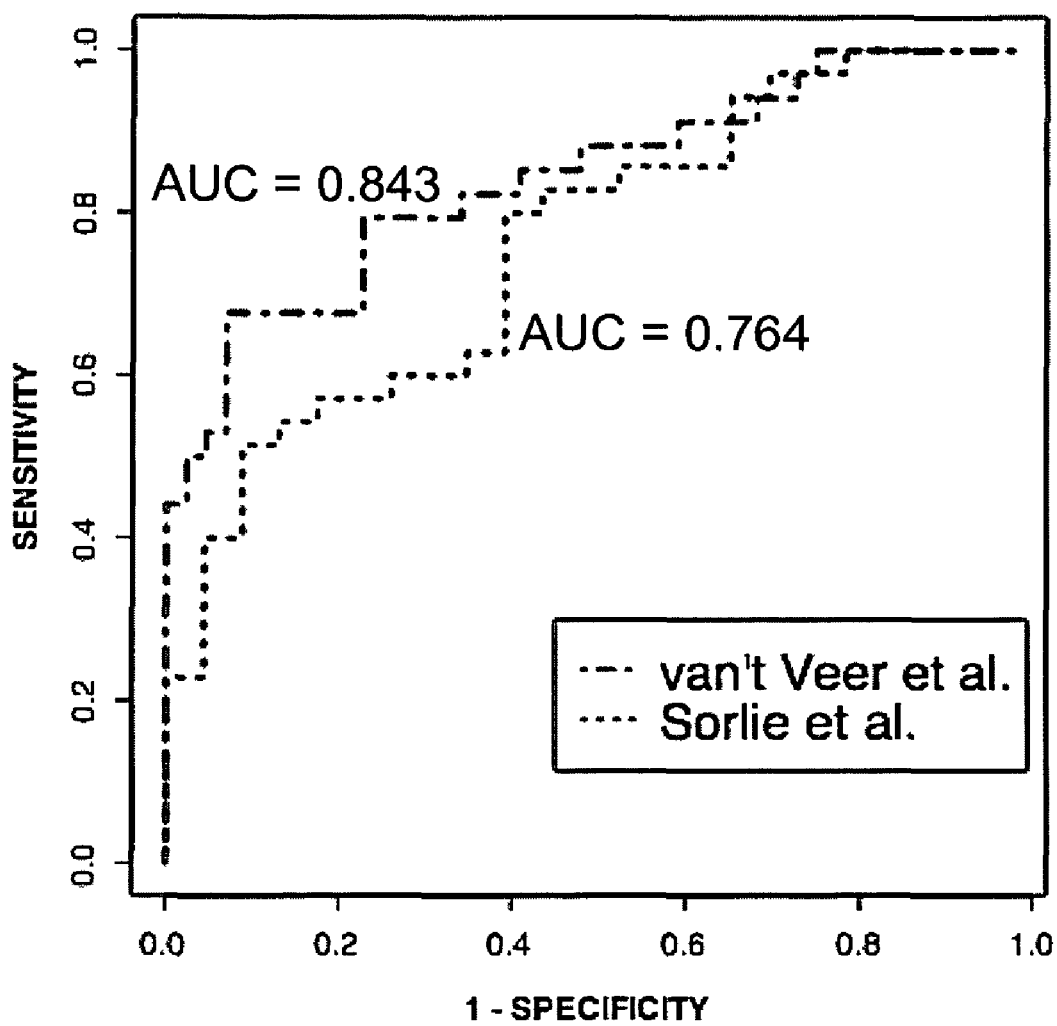
FIG. 3 is a Time dependent ROC analyses of the 28-gene signature in disease-free survival prediction in three breast cancer patient cohorts.
Figure 4:
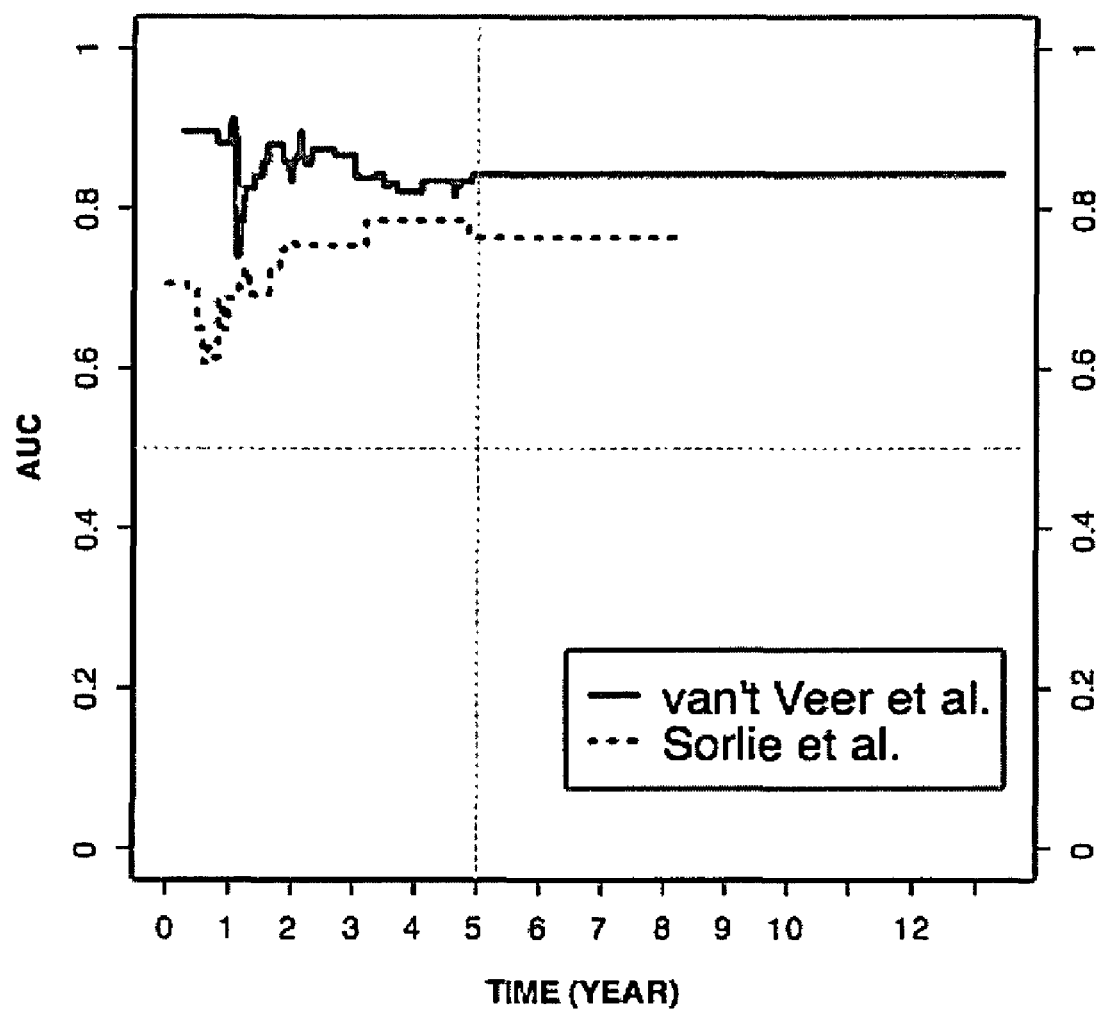
FIG. 4 is a Time dependent ROC analyses of the 28-gene signature in disease-free survival prediction in three breast cancer patient cohorts.

To evaluate the prognostic power of the identified gene signature, two independent validation sets were used (9;10). Using the signature genes, time-dependent ROC analyses were performed to evaluate relapse/metastases prediction on two independent patient cohorts (FIGS. 3 and 4). The area under the ROC (5-year) curve on the data from van't Veer et al. (11) was 0.843 with 25 signature genes in predicting metastatic potential. The AUC (5-year) was 0.764 on the data from Sorlie et al. (10) with eight overlapped genes in the relapse-free survival prediction (FIG. 3).

Figure 5:
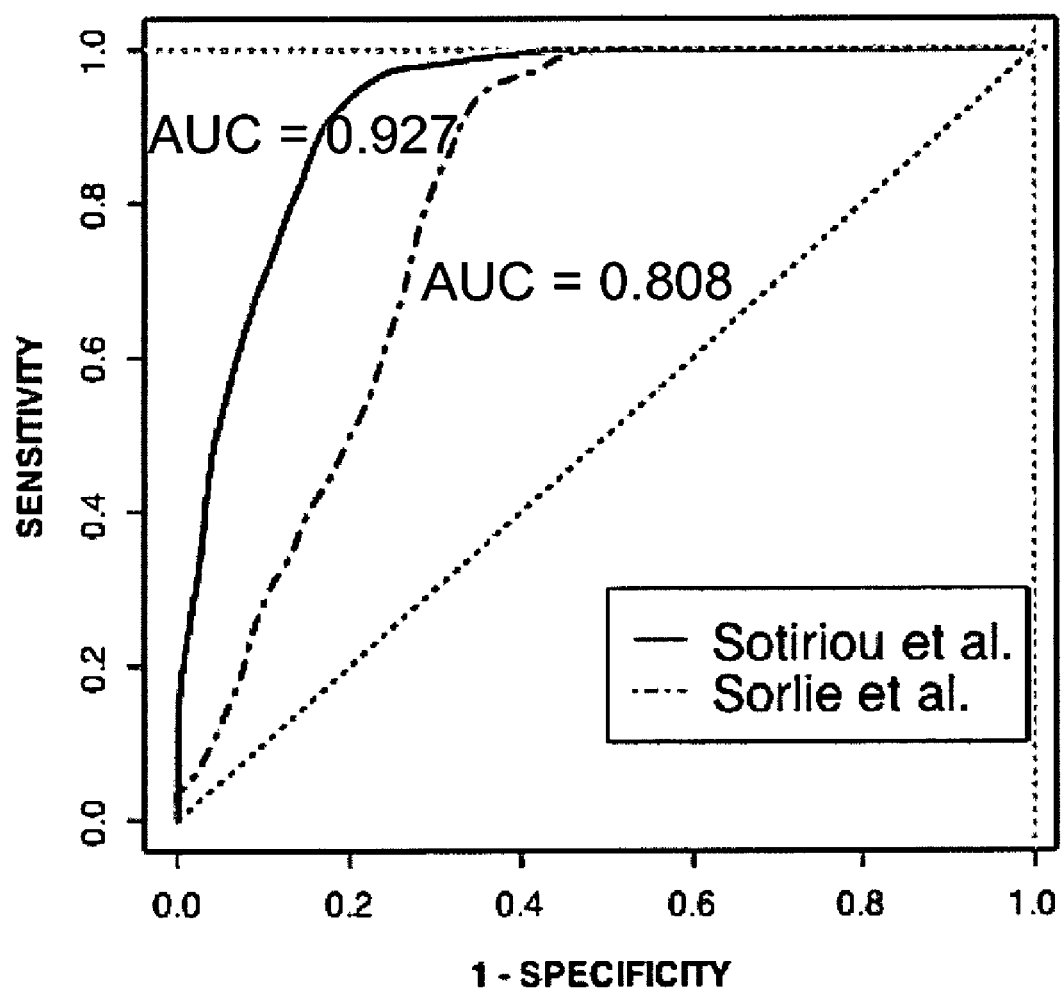
FIG. 5 is a Time-dependent ROC analyses of the 28-gene signature in overall survival prediction in there breast cancer patient cohorts.
Figure 6:
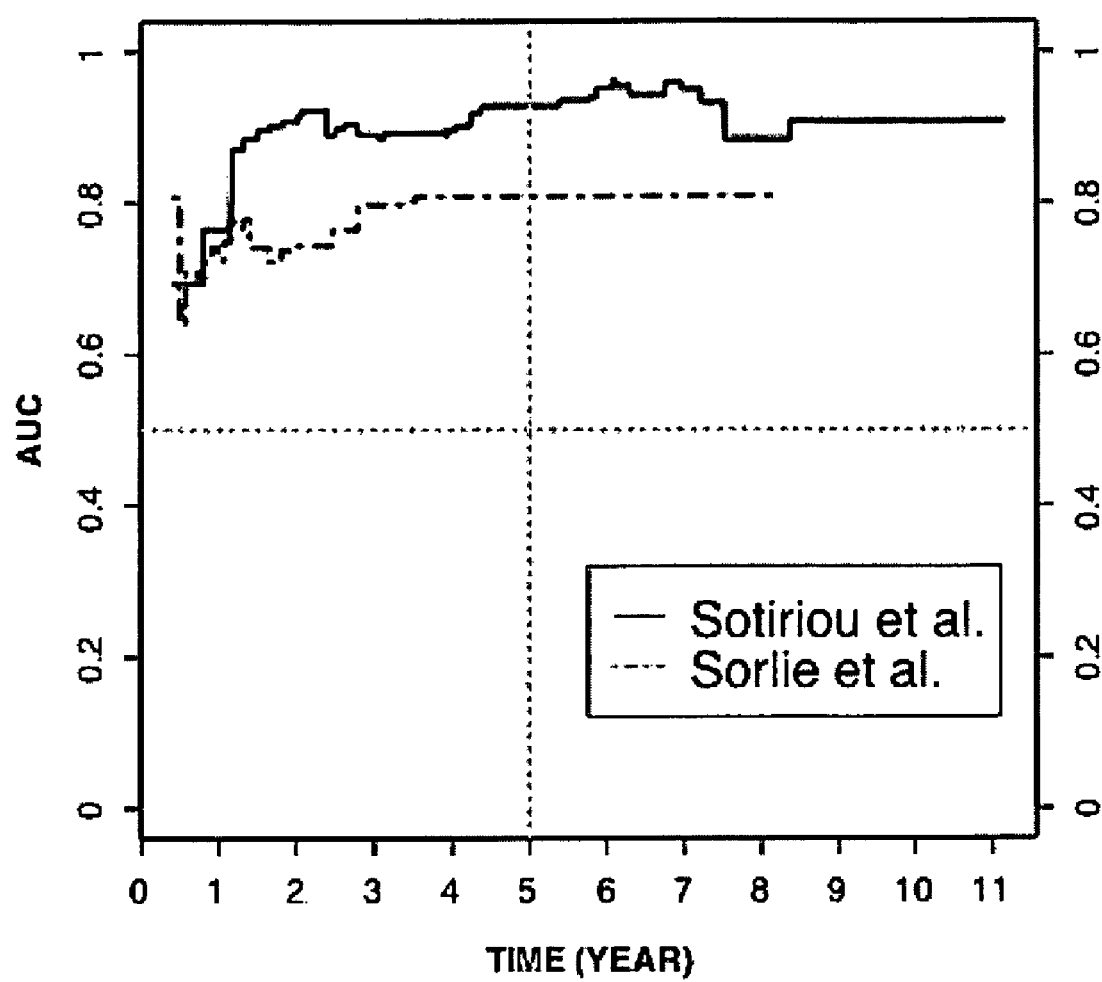
FIG. 6 is a Time-dependent ROC analyses of the 28-gene signature in overall survival prediction in there breast cancer patient cohorts.

Time dependent ROC analysis showed that the 28-gene signature was also predictive of overall survival (P<0.001; FIGS. 5 and 6). In the prediction of overall survival, the AUC (5-year) was 0.927 on data from Sotiriou et al. (Sotiriou C. et al., Breast Cancer classification and prognosis based on gene expression profiles from a population-based study, *Proc. Natl. Acad. Sci.*, USA 2003; 100:10393-8) and 0.808 on data from Sorlie et al. (Sorlie T. et al., Gene expression patterns of breast carcinomas distinguish tumor subclasses with clinical implications, *Proc. Natl. Acad. Sci.*, USA 2001; 98:10869-74).

Among the 28-gene signature, 11 genes had significant association with relapse-free survival in Cox modeling (Table 4).

TABLE 4

Genes that are significantly associated with breast cancer relapse.

| GENE | P-value |
|---|---|
| FGF2 | 0.0039 |
| SLC25A5 | 0.0051 |
| C18B11 | 0.0062 |
| SMARCD2 | 0.0087 |
| TOMM70A | 0.0250 |
| PBX2 | 0.0330 |
| SEC13L | 0.0350 |
| Clone ID: 501651 | 0.0350 |
| IRF5 | 0.0350 |
| DDOST | 0.0470 |
| Clone ID: 182930 | 0.0520 |

Figure 7:
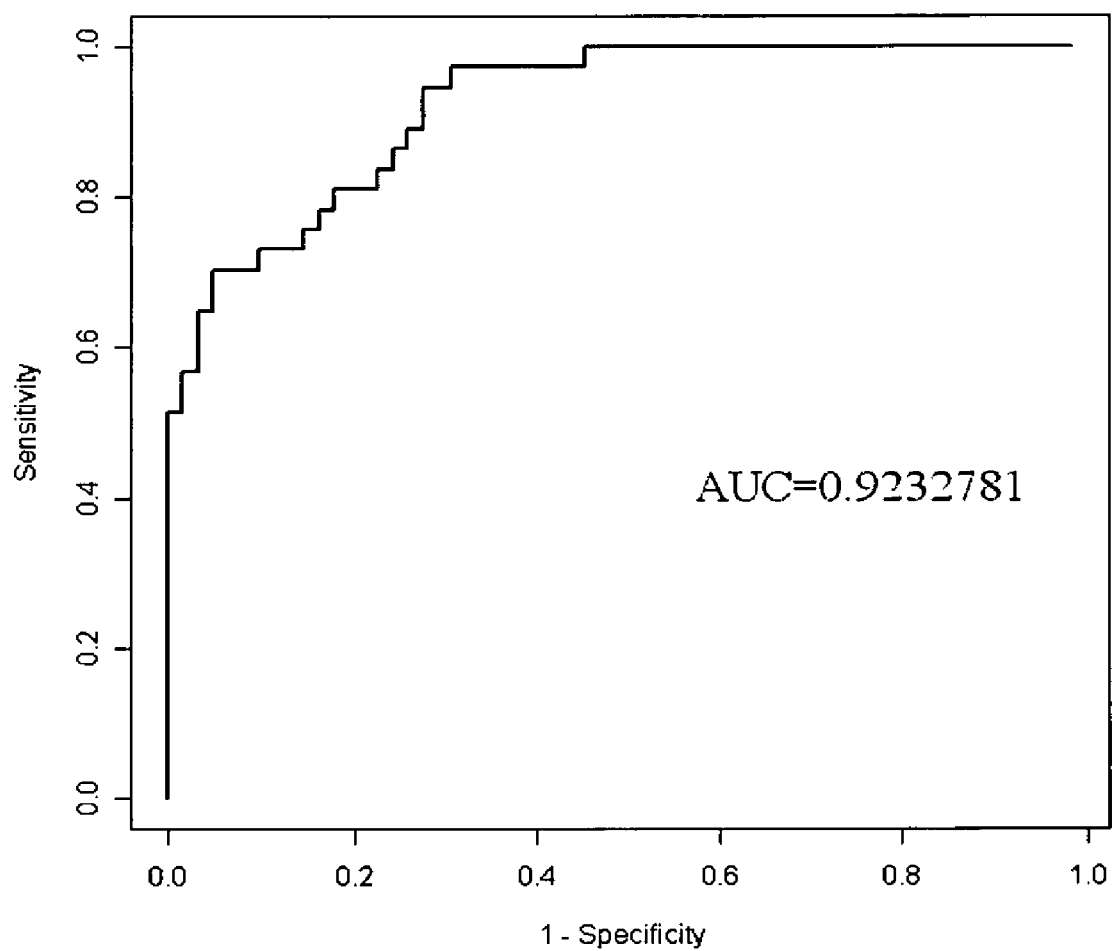
FIG. 7 is a Time-dependent ROC analyses of 15 genes within the 28-gene signature in relapse-free survival prediction in three breast cancer patient cohorts.
Figure 8:
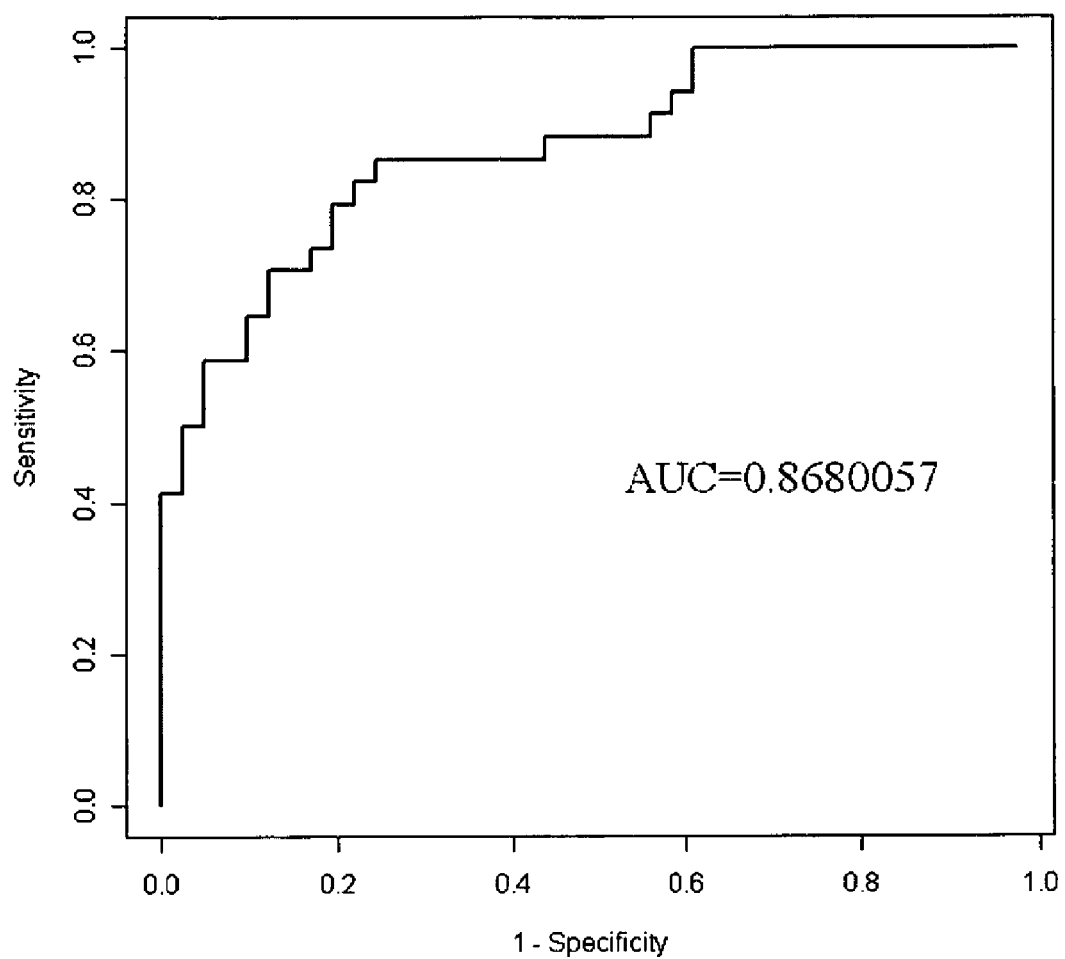
FIG. 8 is a Time-dependent ROC analyses of 15 genes within the 28-gene signature in relapse-free survival prediction in three breast cancer patient cohorts.
Figure 9:
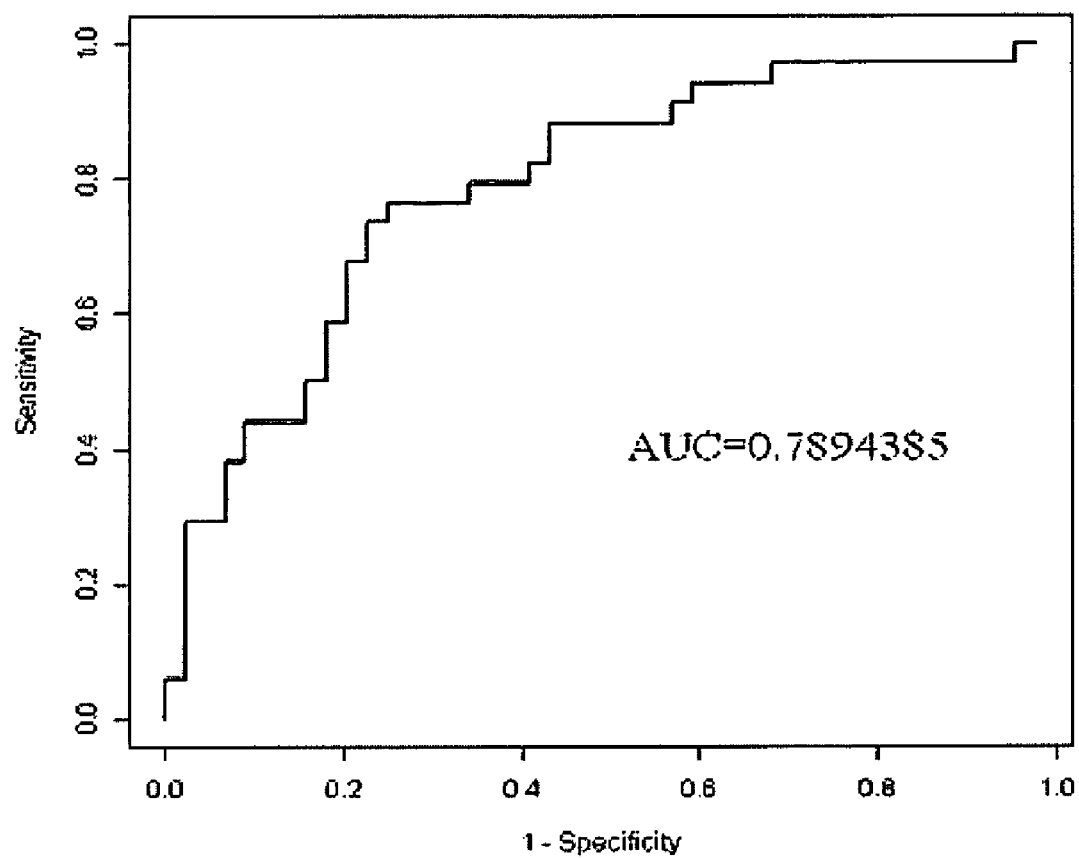
FIG. 9 is a Time-dependent ROC analyses of 15 genes within the 28-gene signature in relapse-free survival prediction in three breast cancer patient cohorts.

Among the 28-gene set, 15 genes (Table 5) predict disease-free survival with an accuracy ranging from 0.79 to 0.92 in three patient cohorts from Sotiriou et al. (8), van't Veer et al. (12), and Sorlie et al. (10) (FIGS. 7, 8, and 9). These 15 genes can be used as a 15-gene signature prognostic model for breast cancer. In addition, the 8 unique genes from Table 4 may be added to form a 23-gene signature prognostic model for breast cancer. The remaining 5 unique genes from Table 1 form a 28-gene signature prognostic model for both breast and ovarian cancer. Together, genes in Tables 4 and 5 can predict both breast cancer relapse and metastases.

TABLE 5

Genes that predicts breast cancer relapse.

| GENE | CLONE ID | Seq. ID No |
|---|---|---|
| MAP2K2 | 769579 | Seq. ID No 44 |
| SMARCD2 | 741067 | Seq. ID No 44-43 |
| S100P | 2060823 | Seq. ID No 31 |
| FAT | 591266 | Seq. ID No 32 |
| DDOST | 50666 | Seq. ID No 29 |
| SSBP1 | 125183 | Seq. ID No 26 |
| PDGFRA | 1643186 | Seq. ID No 27 |
| INPPL1 | 703964 | Seq. ID No 24 |
| RAD50 | 261828 | Seq. ID No 22-23 |
| PLSCR1 | 268736 | Seq. ID No 16 |
| RAD52 | 140004 | Seq. ID No 10 |
| C18B11 | 131988 | Seq. ID No 12 |
| MCM2 | 239799 | Seq. ID No 11 |
| MCF2L | 1781388 | Seq. ID No 8-9 |
| TXNRD1 | 630625 | Seq. ID No 17-21 |

To assess a breast cancer patient's relapse and metastatic potential, risk scores can be generated by using a Cox model of the 28-gene signature, independent of clinical-pathological parameters although any standard risk evaluation could be used. In this application large value of the risk scores indicates a high risk of relapse/metastases, while a small value indicates a lower risk of breast cancer relapse. The 28-gene signature obtained from the training set (8) was fitted into a Cox regression model as covariates. To avoid overfitting, the data set are randomly partitioned into two subsets—one was used to define risk groups by fitting the model and obtaining the risk score cutoffs; the other subset was used to validate the cutoffs for defining the risk groups. The distribution of the risk scores can be categorized into groups of two or more. If two groups, patients could be labeled as high risk at the $65^{th}$ percentile or above and low risk at $64^{th}$ percentile and below. Alternatively, the patients could be categorized into high, low, or intermediate risk group is 39%, 26%, and 35%, respectively in the training set. The cutoffs defined in the training subset can be used to separate the patients in the test subset into high, low and intermediate risk groups.

A further embodiment is the ability to evaluate clinco-pathogic variables for cancer patients. Clincopathogic variable includes, but is not limited to, average metastases-free days, ER and PR status, age, tumor size, and tumor grade. Table 6 displays the clinical characteristics of each risk group, including average relapse-free days, ER status, Her2/neu overexpression, nodal status, age, tumor size, and treatment received on the data from Sotiriou et al. (8). Risk scores were generated for patients in Cox modeling using the gene expression profiles, without including clinicopathologic parameters. The $39^{th}$ and $65^{th}$ percentile of the risk scores were used to partition patients into high, intermediate, and low risk groups. Same analysis is applied to the two validation sets. Table 7 summarizes the clinical characteristics of each risk group, including average metastases-free days, ER and PR status, age, tumor size, and tumor grade on the data from van't Veer et al. (13). Table 8 summarizes the clinical characteristics of each risk group, including average relapse-free days, ER status, age, and tumor grade on the data from Sorlie et al. (10).

TABLE 6

Clinical characteristics of each risk group on the patients from Sotiriou et al.(8)

| Risk Group | Average RFS (days) | % of Age ≧50 yrs | # of Her-2\neu positive cases | % of Tumor Size >2 cm | % of Positive Nodal Status | % of Chemo | % of Hormone | % of ER+ |
|---|---|---|---|---|---|---|---|---|
| High | 969 | 82% | 6 | 82% | 67% | 38% | 79% | 54% |
| Inter. | 2407 | 73% | 1 | 58% | 50% | 35% | 85% | 58% |
| Low | 2781 | 65% | 0 | 47% | 41% | 24% | 74% | 85% |

TABLE 7

Clinical characteristics of each risk group on the patients from van't Veer et al. (14)

| Risk Group | % of Patients | Average RFS (days) | % of Age ≧50 | % of ER+ | % of Tumor Grade 3 | % of T3/T4 Tumors |
|---|---|---|---|---|---|---|
| High | 28% | 553 | 50% | 69% | 81% | 94% |
| Intermediate | 32% | 801 | 84% | 89% | 26% | 89% |
| Low | 40% | 1376 | 70% | 73% | 32% | 77% |

TABLE 8

Clinical characteristics of each risk group (Sorlie et al. (10))

| Risk Group | % of Patients | Average RFS (days) | % of Age ≧50 | % of ER+ | % of Tumor Grade 3 | % of T3/T4 Tumors |
|---|---|---|---|---|---|---|
| High | 28% | 553 | 50% | 69% | 81% | 94% |
| Intermediate | 32% | 801 | 84% | 89% | 26% | 89% |
| Low | 40% | 1376 | 70% | 73% | 32% | 77% |

Clinical variables such as nodal status, tumor size, tumor grade, ER status and HER2/neu overexpression in breast cancer patients affect the disease outcomes. The clinical characteristics of each risk group in the studied cohorts are analyzed including average disease-free survival days, ER and PR status, HER2/neu overexpression, nodal status, age, tumor size, grade, and treatment received. The 28-gene signature is strongly associated with the clincopathogic variables, including tumor size, tumor grade, ER and PR status, and HER2/neu overexpression ($P<0.05$; Table 9).

TABLE 9

Association of gene expression-defined risk groups and clinicopathologic parameters

| | P-Values | | |
|---|---|---|---|
| Risk Groups vs. | Sotiriou et al.(8) | van't Veer et al.(15) | Sorlie et al.(10) |
| Age [1] (<50 yrs or ≧50 yrs) | 0.243 | 0.458 | 0.095 |
| Tumor size (<2 cm or >2 cm) | 0.006* | 0.047* | |
| Tumor grade (1/2 vs. 3) | 0.041* | 0.004* | 0.001* |
| ER status | 0.011* | 0.004* | 0.296 |
| PR status | | 0.001* | |
| Her2/neu | 0.020* | | |

[1] The percentage of patients who were at least 50 years old was 74%, 28%, and 69% in the cohorts from Sotiriou et al. (8), van't Veer et al. (16), and Sorlie et al. (10), respectively.

Figure 10:
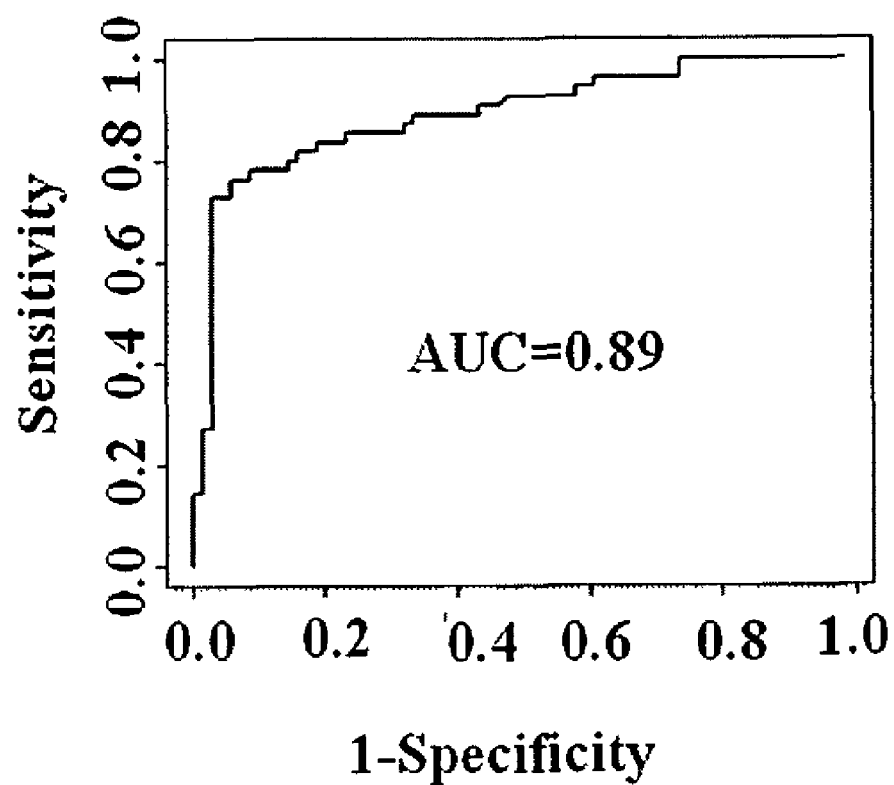
FIG. 10 is a Time-dependent ROC analyses of 24 genes within the 28-gene signature in relapse-free survival prediction in one ovarian cancer patient cohort from Bild et al. (29)

The 28-gene signature also predicts tumor recurrence in ovarian cancer with an accuracy of 0.89 (FIG. 10). Table 10 listed the genes that are predictive of ovarian cancer relapse.

TABLE 10

24 genes that quantifies relapse-free survival of breast cancer

| Gene | Clone_IMAGE | UniGene Cluster ID | Sequence ID |
|---|---|---|---|
| FAM134C | 198917 | Hs.463079 | NM_178126 |
| TOMM70A | 198312 | Hs.227253 | NM_014820 |
| MCF2 | 268412 | Hs.387262 | NM_001099855 |
| | | | NM_005369 |
| RAD52 Pseudogene | 1377154 | Hs.552577 | NM_134424 |
| MCM2 | 239799 | Hs.477481 | NM_004526 |
| C18B11 | 131988 | Hs.173311 | NM_152260 |
| SEC13L | 757210 | Hs.301048 | NM_031216 |
| | | | NM_001013437 |
| SLC25A5 | 291660 | Hs.522767 | NM_001152 |
| PLSCR1 | 268736 | Hs.130759 | NM_021105 |
| TXNRD1 | 789376 | Hs.434367 | NM_003330 |
| | | | NM_001093771 |
| | | | NM_182742 |
| | | | NM_182729 |
| | | | NM_182743 |
| RAD50 | 261828 | Hs.242635 | NM_005732 |
| | | | NM_133482 |
| INPPL1 | 703964 | Hs.523875 | NM_001567 |
| PBX2 | 80549 | Hs.509545 | NM_002586 |
| SSBP1 | 125183 | Hs.490394 | NM_003143 |
| PDGFRA | 376499 | Hs.74615 | NM_006206 |
| DDOST | 50666 | Hs.523145 | NM_005216 |
| IGHA1 | 182930 | Hs.497723 | AK128652 |
| S100P | 135221 | Hs.2962 | NM_005980 |
| FAT | 591266 | Hs.481371 | NM_005245 |
| FGF2 | 324383 | Hs.284244 | NM_002006 |
| INSM1 | 22895 | Hs.89584 | NM_002196 |
| IRF5 | 260035 | Hs.521181 | NM_001098629 |
| | | | NM_002200 |
| | | | NM_001098627 |
| | | | NM_001098630 |
| | | | NM_001098628 |
| | | | NM_032643 |
| | | | NM_001098631 |
| MAP2K2 | 769579 | Hs.465627 | NM_030662 |

In the present invention, target polynucleotide molecules are extracted from a sample taken from an individual afflicted with breast cancer or ovarian cancer. The sample may be collected in any clinically acceptable manner, but must be collected such that marker-derived polynucleotides (i.e., RNA) are preserved. mRNA or nucleic acids derived there from (i.e., cDNA or amplified DNA) can be labeled distinguishably from standard or control polynucleotide molecules, and both are simultaneously or independently hybridized to a detection mechanism. A detection mechanism can be any standard comparison mechanism such as a microarray or an assay of reverse transcription polymerase chain reaction (RT-PCR) comprising some or all of the markers or marker sets or subsets described above. This process identifies positive matches. Alternatively, mRNA or nucleic acids derived therefrom may be labeled with the same label as the standard or control polynucleotide molecules to identify positive matches, wherein the intensity of hybridization of each at a particular probe or primer is compared for such an identification. A sample may comprise any clinically relevant tissue sample, such as a tumor biopsy or fine needle aspiration, or a sample of bodily fluid, such as blood, plasma, serum, lymph, ascetic fluid, cystic fluid, urine, or nipple exudate. The sample may be taken from a human, or from non-human animals such as horses, mice, ruminants, swine or sheep. Patients' gene expression levels may be quantified by any means known in the art based on the marker sets defined above. Patients may be classified based on the quantitative expression profiles using any means known in the art. For example, the risk scores of a patient cohort may be generated using a Cox proportional hazard model. Patients with a risk score greater than the median is defined as high risk, whereas patients with a risk score less than the median is classified as low risk. Alternatively, a patient may be classified as high risk if this patient's gene expression profile is correlated with the high risk signature, or classified as low risk if this patient's gene expression profile is correlated with the low risk signature. A patient's prognostic categorization can also be determined by using a statistical model or a machine learning algorithm, which computes the probability of recurrence based on this patient's gene expression profiles. Cutoffs can be defined for patient stratification based on specific clinical setting. In addition, patients may be defined into three risk groups in the prognostic categorization based on the marker sets defined above.

Methods for preparing total and poly(A)+RNA are well known and are described in (17). RNA may be isolated from eukaryotic cells by procedures that involve cell lysis and denaturation of the proteins contained therein. Cells of interest include wide-type cells (i.e., no mutation), drug-treated wild-type cells, tumor- or tumor-derived cells, modified cells, normal or tumor cell lines cells, and drug-treated modified cells. Total RNA may also be extracted from samples using commercially available kits such as the RNeasy mini kit according the manufacturer's protocol (Qiagen, USA).

Additional steps may be performed to remove DNA (17). If desired, RNase inhibitors may be added to the lysis buffer. Likewise, a protein denaturation/digestion step may be added to the protocol. mRNA may be purified by means such as magnetic separation using Dynabeads (Dynal) or the Invitrogen FastTrack 2.0 kit (10).

For many applications, it is desirable to preferentially enrich mRNA with respect to other cellular RNAs, such as transfer RNA (tRNA) and ribosomal RNA (rRNA). Total RNA may also be linearly amplified using the original or modified Eberwine method (18) and be used as a reference for cDNA analysis (8).

The sample of RNA can comprise a plurality of different mRNA molecules, each different mRNA molecular having a different nucleotide sequence. In a specific embodiment, the RNA sample has not been functionally annotated.

The present invention provides a set of biomarkers for the identification of conditions of indications associated with breast cancer. Generally, the markers sets were identified by determining which of 25,000 human genes had expression patterns that correlated with the conditions or indications.

In one embodiment, the expression of all markers in a sample X is compared to the expression of all markers in the 28-gene signature or subsets as described above derived from tumor samples. The comparison may be accomplished by any means known in the art. The expression level may be determined by isolating and determining the level (i.e., the abundance) of nucleic acid transcribed from each marker gene. Alternatively, or additionally, the level of specific proteins translated from mRNA transcribed from a marker gene may be determined. For example, expression levels of various markers may be measured by separation of target nucleotide molecules (e.g., RNA or cDNA) derived from the markers in agarose or polyacrylamide gels, followed by hybridization with marker-specific oligonucleotide probes. Alternatively, the comparison may be accomplished by the labeling of target polynucleotide molecules followed by separation on a sequence gel. The comparison may also be accomplished by measuring the gene expression level using real-time reverse transcription polymerase chain reaction with marker-specific primers/probes. Patients may be classified based on the quantitative expression profiles using any means known in the art. For example, the risk scores of a patient cohort may be generated using a Cox proportional hazard model. Patients with a risk score greater than the median is defined as high risk, whereas patients with a risk score less than the median is classified as low risk. Alternatively, a patient may be classified as high risk if this patient's gene expression profile is correlated with the high risk signature, or classified as low risk if this patient's gene expression profile is correlated with the low risk signature. A patient's prognostic categorization can also be determined by using a statistical model or a machine learning algorithm, which computes the probability of recurrence based on this patient's gene expression profiles. Cutoffs can be defined for patient stratification based on specific clinical setting. In addition, patients may be defined into three risk groups in the prognostic categorization based on the marker sets defined above.

A marker is selected based on its predictive power of breast cancer recurrence, including local recurrence and distant metastasis. A combination of Random Forests (19) and Linear Discriminant Analysis (LDA) is used to identify gene signatures for predicting breast cancer recurrence/metastases. Random forests of software R is first used to identify a small subset of genes from the original microarray data. Linear Discriminant Analysis of software SAS is used to further refine the gene signature.

Random forests are a generalization of the standard tree algorithms (20). The basic step of random forests is to form diverse tree classifiers from a single training set. Each tree is built upon a bootstrap sample from the training set. The variables used for splitting the tree nodes are a random subset of the whole variables set. The classification decision of a new case is obtained by majority voting (unless the cutoff value is user defined) over all trees. In random forests, about one-third of the cases in the bootstrap sample are not used in growing the tree. These cases are called "out-of-bag" (OOB) cases and are used to evaluate the algorithm performance. A very important function of random forests is variable importance evaluation. The importance of a variable is defined in terms of its contribution to classification accuracy. Based on the variable importance measure, backward elimination was used to identify the gene subset with the smallest OOB error rate. Here, the OOB error rate was not used to assess the prediction accuracy of the identified gene subsets. Instead, it served as a stopping rule for feature selection. The varSelRF package of software R (21) was used according to the following steps:

1. Build a forest with N trees and obtain a ranking of variable importance
2. Remove 20% of the least important variables
3. Construct a new forest with K trees
4. Repeat steps 2 and 3 until two genes are left
5. Select the gene subset with the smallest OOB error rate In the experiments, N=3,000 and K=1,000 are chosen because the large number of trees in the initial forests are likely to produce stable importance measures (21). The "0-Standard Error (0-SE) rule" is used, which identifies the gene subset with the smallest OOB error rate. The "0-SE rule" usually selects more genes than the "1-SE rule" does. Since further gene filtering would be performed by using Linear Discriminant Analysis, the gene subsets are selected with the lowest prediction error using random forests.

Discriminant analysis is used to determine which variables discriminate two or more naturally occurring groups in prognosis. Given a number of variables as the data representation, each class is modeled as multivariate normal distribution with a covariance matrix and a mean vector. Instances are classified to the label of the nearest mean vector based on Mahalanobis distance. The decision surfaces between classes become linear if the classes have a common covariance matrix. When the distribution within each group is assumed to be multivariate normal, a parametric method can be used to develop a discriminant function. Such function is determined by a measure of generalized square distance which is based on the pooled covariance matrix as well as the prior probabilities of group membership. The generalized squared distance $D_i^2(x)$ from input x to class i is:

$$D_i^2(x)=d_i^2(x)+g(i)$$

where $d_i^2(x)=(x-m_i)'V^{-1}(x-m_i)$ is the squared distance from x to group I, $m_i$ is the p-dimensional mean vector for group I; V is the pooled covariance matrix and g(i) depends on the prior probability of class i. In practice, the prior probability can be assumed as equal for all groups (refer to SAS Users' Manual). In this study, we assumed equal prior probability and thus g(i)=0. x is classified into class I, if $D_i^2(x)$ is the smallest among all the distance measures. We selected the gene markers using backward selection of stepwise discriminant analysis with software SAS.

Linear Discriminant Analysis (LDA) is used to refine the gene signature obtained from random forests and assess the classification accuracy of models in predicting 5-year relapse-free survival based on the identified gene signatures. Leave-one-out cross-validation is used in the evaluation to identify the optimal marker subset (22).

Once a marker set is identified, validation of the marker set may be accomplished by a survival analysis. To evaluate the accuracy of survival prediction, time-dependent receiver operating characteristic (ROC) analysis for censored data (23;24) was performed with software R. Time-dependent ROC analysis extends the concepts of sensitivity, specificity, and ROC curves for time-dependent binary disease variables in censored data. In this embodiment, the binary disease variable $R_i(t)=1$, if patient i has recurrent or metastatic breast cancer prior to time t; otherwise, $R_i(t)=0$. For a diagnostic marker M, both sensitivity and specificity are defined as a function of time t:

$$\text{sensitivity}(c,t)=P\{M>c|R(t)=1\}$$

$$\text{specificity}(c,t)=P\{M\leq c|R(t)=0\}$$

A ROC(t) is a function of t at different cutoffs c. A time-dependent ROC curve is a plot of sensitivity(c, t) vs. 1−specificity(c, t). The area under the ROC curve (AUC) can be used as an accuracy measure of the ROC curve. A higher prediction accuracy is evidenced by a larger AUC(t) (23;24).

The prediction of patient outcome may be accomplished with any means known in the art. For example, to estimate a patient's recurrent and metastatic potential, risk scores are generated by fitting the identified gene predictors in a Cox proportional hazard model as covariates. A higher risk score represents a higher probability of tumor recurrence. The distribution of the risk scores can be used to classify the patients into three groups: high-risk, low-risk, and intermediate-risk. Alternatively, patients may be stratified into two groups: high- or low-risk. Kaplan-Meier analysis may be used to assess the disease-free survival probability of three risk groups in the studied patient cohorts (8;10;25). Similarly, a Cox proportional hazard model may be developed to estimate a patient's overall survival probability. A higher survival risk score represents a higher risk for death from breast cancer. Alternatively, a Linear Discriminant Analysis (LDA) function may be determined by a measure of generalized square distance which is based on the pooled covariance matrix based on the marker sets described above as well as the prior probabilities of group membership for prognostic categorization.

For prognostic predictions in clinic, the expression levels of the markers can be measured with any means known in the art such as cDNA microarrays (8; 10;26), various generations of Affymetrix gene chips (Affymetrix, Santa Clara, Calif.), and real-time reverse transcription polymerase chain reactions. The present invention further provides for kits comprising the marker sets above. The analytical methods described above can be implemented by use of following computer systems. For example, a computer system can be an Intel 8086-, 80386-, 80486-, or Pentium-based process with preferably 64 MB or more of main memory. The computer system can be linked to an external component, including mass storage. This mass storage can be one or more hard disks, preferably of 1 GB or more storage capacity. Other external components include regular accessories for a computer such as a monitor, a mouse, or a printer.

The software program described in above sections can be implemented with software packages R and SAS. The software to be included in the kit comprises the data analysis methods for this invention as disclosed herein. In particular, the software algorithms may include mathematical procedures for biomarker discovery, including the computation of the Mahalanobis distance between clinical categories (i.e., relapse status) and marker expression. The software may also include mathematical procedures for computing the regression coefficients between the marker expression and patient survival.

Alternative computer systems and software for implementing the analytical methods of this invention will be apparent to one of skill in the art and are intended to be comprehended within the accompanying claims.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

What is claimed is:

1. A breast cancer prognosticator comprising a detection mechanism which comprises nucleic acids, wherein the nucleic acids consist of SEQ ID NOs: 8-12, 16-24, 26-27, 29, 31-32, and 42-44.

2. The breast cancer prognosticator of claim 1 wherein said detection mechanism is a microarray.

* * * * *

SEQUENCE LISTING

<160> NUMBER OF SEQ ID NOS: 44

<210> SEQ ID NO 1
<211> LENGTH: 1145
<212> TYPE: DNA
<213> ORGANISM: Homo sapiens

<400> SEQUENCE: 1

```
gatgaacaga tatgctatgg gagtcttctg ctggaggttc cattcactgt gcgtgctgca      60
ccatggtgag cccatttggc aggggtacca aagtgatcct ccatcttaaa gaagatcaga    120
```

```
cagagtacct agaagagagg cgggtcaaag acagtagtga agaagcattc tcagttacat    180
agggcgtcat ccccatccac cacttcatat tggcagcaca ggcaacgcag cagcaaggca    240
cacatcccag tgcatgcatc gcaggccagc aggcaagcag cacacaggtg cagcacacag    300
cacagcaggc acagcataac agcatgcatt gcacagccac aacagcccca aagcatctgc    360
acagcatgct cgggtctcca gcatgcgagg cagggcatcg caccagccgg tcacagggca    420
tcacagcaca gcacagcaac accactcaag caagcatcaa caagcagcac aatcaccatc    480
tgcatcgcag gcacagcaca cttcacagac caaagcaacc acaagccgtc cattaggcgc    540
accgcagaag acacccattg cattgcacga tcccaccacg caaagcaagg cagtcattgg    600
ggaggaaatt ctcacaacag cagccctcca cattacatgg acattgggcg caaggaaccg    660
aatctgggcc tcggtccaaa cagacccagc gtactatcac acatgggtac gacacaggga    720
gtcacaggaa ctgggacacg atcacaagcc cggacacat  aaggacaaag ggtaattacc    780
ccgttccgga tcgggggagc tcccacatat agggaacgct cttcaggaag acaccacaag    840
gacagaccaa gaccgaagac acacactaca aaaacgatca tatgcgtcgc ggacacggaa    900
ggtggtacac acatacaatg gggaccaagg actcggtgac actgaacaca cgagacacgc    960
caagagagga catccacgaa acacctcatc accgggtagg ggcggccgga tcgaacatca   1020
taggaaacga cagcgtggcc gccgtcgcac accgttcaca ccaggacagc acaagtggac   1080
cacaagcggc acacgaccac acactctctc cgaagaagac aaaacggcag caacagcatg   1140
tgaca                                                                1145
```

<210> SEQ ID NO 2
<211> LENGTH: 3590
<212> TYPE: DNA
<213> ORGANISM: Homo sapiens

<400> SEQUENCE: 2

```
agctctggga caggagccca gcactagaag ttggcggtgt ttcccctcgg tgatcagcac     60
tgaagacaga ggactcacca tggagtttgg gctgagctgg gttttcctcg ttgctctttt    120
aagaggtgtc cagtgtcagg tgcagttggt ggagtctggg ggaggcgtgg tccggcctgg    180
ggcgtccctg agactctcct gtgcagcgtc tggattcaac ttcaaggact atgtcatgca    240
ttgggtccgc caggctccag gcaaggggct tgagtgggtg gccgttgcgt gggacgtagg    300
aattcccatt cattatgcag actccgtcaa gggccgattc accatctcga gagacaactc    360
caagaatacc ctctatttgc aaatggatag cctgaaagtc gaggacacgg ctgtctatta    420
ttgtgtgaga gattgggggg acgatgacta cagtagtaaa tactattact acactctgga    480 cgtctgggge cgagggacaa cggtcaccgt ctcctcaagt aagagtggcc atttagggc    540 ctttatttg tcttagtgcg tgcggcggtt cctgagcatt gcaagttggt cctcggggcg    600
tgttccgagg ggtcctgggc ggcctggcca ggaggggacg ggcactgggg tgccttgagg    660
ctctgggaga ctccgtggat tttccggtgg ctttgaaaaa tgggactctg atgcagagaa    720
tgagcccggg ggttggggag gcacatttgg acgagatgcc tgaagaaacc aggggtctca    780
gcgatggcta aggaatgtgt ctcaggagtg gtgtctgtcg gactgcagga tggctgcaat    840
cgtgaaagct tttctctaga cttgtgaggt gcgctgtggg tctacctgca tgttaaagta    900
tttattggct ggaaagagaa ttggcggagt gggtgaatcc agccagggggg gacgcgtagc    960 cccggcctcg atgacagcag ggtcggggge agggtagcc cagaaacagt ggctgccgtc   1020
ctgacagggg cttagggagg ctccaggacc tcagggcctt gaagctggtt tccatgagaa   1080
```

```
aaggattgtt tatcctagga ggcatgcata ttgttaaagg acaggatatg tttgaagtgg   1140
cttctgagaa aaagggttaa gaaaattctg acttaaaaat gtgagagact ttcaagtgta   1200 ttaattttt  taactgtcca agtatttgag attcttatca tttcattaac acccatgagt   1260
gatatgtgtc cggaattgag gccaaagcaa gctcagctaa gaaatactag cacagtgctg   1320
tcggccccga tgcgggactg cgttttgacc atcgtaaatc aactttctt  ttttaattaa   1380 ttgagcgaag ctggaagcag atgatgaatg agagtcaaga tggctgcatg ggggtctccg   1440
gcacccacag caggtggcag gaagcaggtc accgcgagag tctattttag gaagcaaaaa   1500
aacacaattg gtaaatttat cacttctggt tgtgaagagg tggttttgcc caggcccaga   1560
tctgaaagtg ctctactgag caaaacaaca cctggacaat ttgcgtttct aaaataaggc   1620
gaggctgacc gaaactgaaa aggctttttt taactatctg aatttcattt ccaatcttag   1680
cttatcaact gctagtttgt gcaaacagca tatcaacttc taaactgcat tcattttaa    1740 agtaagatgt ttaagaaatt aaacagtctt agggagagtt tatgactgta ttcaaaaagt   1800
tttttaaatt agcttgttat cccttcatgt gataactaat ctcaaatact ttttcgatac   1860
ctcagagcat tattttcata atgactgtgt tcacaatctt tttaggttaa ctcgttttct   1920
ctttgtgatt aaggagaaac actttgatat tctgatagag tggccttcat tttagtattt   1980
ttcaagacca cttttcaact actcacttta ggataagttt taggtaaaat gtgcatcact   2040
atcctgaatt atttcagtta agcatgttag ttggtggcat aagagaaaac tcaatcagat   2100
agtgctgaag acaggactgt ggagacacct tagaaggaca gattctgttc cgaatcaccg   2160
atgcggcgtc agcaggactg gcctagcgga ggctctggga gggtgactgc caggcccggc   2220
ctgggctttg ggtctccccg gactacccag agctgggacg cgtggcttct gctgccgggc   2280
cgactggctg ctccggcccc agcccttgtt aatggacttg gaggaatgat tccatgccaa   2340
agctttgcaa ggctcgcagt gaccaggcgc ccgacatgct ttcagaaatg gactcagatg   2400
ggcaaaactg acctaagctg acctagacta aacaaggctg aactgagctg acctgagctg   2460
agctgggcta agtggacca  gcatcccga  ccagccccaa ggtcttcccg ctgagcctct   2520
gcagcaccca gccagatggg aacgtggtca tcgcctgcct ggtccagggc ttcttccccc   2580
aggagccact cagtgtgacc tggagcgaaa gcggacaggg cgtgaccgcc agaaacttcc   2640
cacccagcca ggatgcctcc ggggacctgt acaccacgag cagccagctg accctgccgg   2700
ccacacagtg cctagccggc aagtccgtga catgccacgt gaagcactac acgaatccca   2760
gccaggatgt gactgtgccc tgcccagttc cctcaactcc acctacccca tctccctcaa   2820
ctccacctac cccatctccc tcatgctgcc accccgact  gtcactgcac cgaccggccc   2880
tcgaggacct gctcttaggt tcagaagcga acctcacgtg cacactgacc ggcctgagag   2940
atgcctcagg tgtcaccttc acctggacgc cctcaagtgg gaagagcgct gttcaaggac   3000
cacctgaccg tgacctctgt ggctgctaca gcgtgtccag tgtcctgccg ggctgtgccg   3060
agccatggaa ccatgggaag accttcactt gcactgctgc ctaccccgag tccaagaccc   3120
cgctaaccgc cacctctca  aaatccggaa acacattccg gccgaggtc  cacctgctgc   3180 cgccgccgtc ggaggagctg gccctgaacg agctggtgac gctgacgtgc ctggcacgtg   3240
gcttcagccc caaggatgtg ctggttcgct ggctgcaggg gtcacaggag ctgccccgcg   3300
agaagtacct gacttgggca tcccggcagg agcccagcca gggcaccacc accttcgctg   3360
tgaccagcat actgcgcgtg gcagccgagg actggaagaa gggggacacc ttctcctgca   3420
tggtgggcca cggggccctg ccgctggcct tcacacagaa gaccatcgac cgcttggcgg   3480
```

```
gtaaacccac ccatgtcaat gtgtctgttg tcatggcgga ggtggacggc acctgctact      3540
gagccgcccg cctgtcccca cccctgaata aactccatgc tcccccaagc                 3590

<210> SEQ ID NO 3
<211> LENGTH: 2324
<212> TYPE: DNA
<213> ORGANISM: Homo sapiens

<400> SEQUENCE: 3
tttaactctt tgttaagtac tcaagtacaa agtgatctct tctttcatga actttgctat        60
aactgttgaa aggattggtg tcaggctctc tcaaccctgg gagtttccaa aatttagcaa       120
atattacttg tgataagctt aaatgccaca tcgctaagta caattattac caggaatccg       180 tcaagggga gatagccccg ctcacaccct tagacccaaa caggtgctgg ttcatgcttt        240
ctccacaaat tggcagttgg gtacttcccc actgtcatca cagttgagct catttttaaca      300 tatattcaaa gaagcttttt agtttctact cctgaattgt agtgttcaag ttatttgcct      360
tcctgggtaa gaaaatttta acccaagtct gggattctct ggcacctgtc ttttcccatc      420
tttcaatgag ttggcaagat taggtcaaat ttcaatgcta aatttgattt tttgaatttt      480
aaatagttgc actttatttc atgctgacca ccaacttaat ttatacattt taaaataaaa      540
ttatcctaga agtgttgtaa acgtgggaaa attttaatta gtgttggagg tcattagatt      600
ggactcaggt ttaaatataa tgatctcttc acagcttatt tgatgtttaa gagcaacttg      660
tgtgatctta gctttgcagg ttttctgtaa tttatgtagc acaataaagg ataaccagtt      720
gactgtgtta ctggactctg agttctcaca gctagtttca tctaagcttg gtttattatc      780
atttctgctt tggattttttt tgtgcatcac atgaatactt agaaatccat tgttttcag      840 tgtagtacct agggtgaagt agatgctgca caagtaagtt taagggaata aaagtcccga      900
cactttatat acatgttgag gggcacgatt taagagactg aaacagttta cattaaactg      960 ttttttatttt ctgccagtag actctatctg cttaaaaaaa taaaaattgt tcaacccagt     1020
gttctccagc atcaggacat tacagttgta atctatgttg taatcttttc aaataagaaa     1080
agctactcct tattctctac agtgtaggct taattttaga accgataatt tactatatct     1140
gcattattga tattttaag tagtagtttt aaaaataatt atttctatgt ggagggtgtt      1200
ttaatttggg attttttttt tcttgtaaca ggtgctattt gtaaatatga aggggaaaag     1260
tcacttagtt aaaagtctag cttatgtcat aattaagata caattattca tttcatgttt     1320
gattctatta aactagtggc aaaacagaat tggtccctta gtttttaga ttacctttcc      1380 ccctatatca caaaaatatc tcttttccata tgatctcata attgaggcaa agaagctaag    1440
ggtttattta aaatgtgtat aagcttgaat ttggtcaaca ctgcataatt tgaaatcact     1500
ctgcatttgt cactgcagct tactgtatgc ttgaaaggcc ttgtgtgttt gtcttaattt     1560
tagtgaaaaa attagaattt ctgccattca tgtacaaaaa aattacaact acagcaaaca     1620
agataaaaat gctggtttgc attaatactg ttttagtctt aagagcaatt tatattatgt     1680
gaaatgctgt tacacatatt ttgttggcca tatttcattt tgagaaacag ttgttcaggt     1740
acaaacatga aaaacaactc tagctatgac tcttaatgtt caattgcaaa ataaagatgt     1800
gctttagtaa tctaaagtac agaagttttg aagattattt tatgggagtt tttcatgggc     1860
ttttctaaca gtggttatat ttagtaactg gttatcagga atggagagaa tgacaagtgt     1920
aaaatttatt tctggagtta ttgactcaca tagtggctgt atttgaggaa agggagtagg     1980
tgaggaacta aaagggattt agaagattaa atagtgtctg aagaggccgg gcgcggtggc     2040
```

-continued

| | |
|---|---|
| tcacgcctgt aatcccagca ttttggagg ctgaggcggg cagatcacaa ggtcaggaga | 2100 |
| tcgagatcat cctggccaac atggagaaac cccgtctcta ctaaaaatac aaaaattagc | 2160 |
| tgagggtggt ggcgcacgcc tgtagtccca gctacttagg aggctgaggc aggaggatca | 2220 |
| cttgaacctg ggaggtggag gttgcagtga gccgagattg attgcgccac tgcaccccag | 2280 |
| cctggtgaca aagtgaaact ccatctcaaa aaaaaaaaaa aaaa | 2324 |

<210> SEQ ID NO 4
<211> LENGTH: 561
<212> TYPE: DNA
<213> ORGANISM: Homo sapiens

<400> SEQUENCE: 4

| | |
|---|---|
| tttttttttt ttttaatgtt tttagagaca gggtcattct ctgacaccca agctggagtg | 60 |
| caacagcacc atcacagctc agtgcaacct tgaattcccg gacttaaacc atcctcccac | 120 |
| ctcagcttcc tagataggtt gggccacagg gatgcaccac catgcccagc tatttgtttg | 180 |
| tttcattgtt gttgttgttg ttgttgttgt tattgagaca aggtctcctt ctgtaaccct | 240 |
| tctggaatgc agtggtgtaa ccacagccca ctgcagcctc gaactcccag gaccaaatga | 300 |
| tcctcccacc tcaatctccc aagtagctgg gactacaggc atgagccacc atgtccggcc | 360 |
| caattttttt taattacttt ttgtagagac aatatcttgc tatgttgccc aggctgacct | 420 |
| caaactcctc gcctcaagtg attatcccac cttggcctcc caaatcacct gaaattacag | 480 |
| gagtaagcta ctgcacctgg tctaaaacaa ggacctttt aaaagtcaaa atgggccggg | 540 |
| catggtggct caggtctgta a | 561 |

<210> SEQ ID NO 5
<211> LENGTH: 479
<212> TYPE: DNA
<213> ORGANISM: Homo sapiens
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t

<400> SEQUENCE: 5

| | |
|---|---|
| ttttttttaa tgttttaga gacagggtca ttctctgaca cccaagctgg agtgcaacag | 60 |
| cccatcacag ctcagtgcaa ccttgaattc ccggacttaa accatcctcc cacctcagct | 120 |
| tcctagatag gttgggccac agggatgcac caccatgccc agctatttgt tgtttcatt | 180 |
| gttgttgttg ttgttgttgt tgttattgag acaaggtctc cttctgtaac ccttctggga | 240 |
| atgcagtggt gtaaccnagg cccactgcag cctcgaactc ccgggaccaa atgatcctcc | 300 |

```
cacctcaatc tcccaagtag gctggggact tacagggcat gaggccacca tgttccgggc    360 ccaattttt  ttaattactt tttgtaggag acaatatct  tggctatgtt ggcccnggt     420 tgacctcaaa ttcggggcnt caagtgatta tncccacntg gggcntccca aatcattgg     479
```

<210> SEQ ID NO 6
<211> LENGTH: 102
<212> TYPE: DNA
<213> ORGANISM: Homo sapiens

<400> SEQUENCE: 6

```
gcccagctga tttttgtatt tttggtggag acggggtttc actatggtgg ccgggctggt     60
cttgaactcc agcctgctca acaagagtga aactctgtct ca                       102
```

<210> SEQ ID NO 7
<211> LENGTH: 4376
<212> TYPE: DNA
<213> ORGANISM: Homo sapiens

<400> SEQUENCE: 7

```
cgctgtatac gcgcccctcc tcggcttcag taggcaagag ggccatctgc ccttctttcc     60
tgaaggtaga ggggacaaca ccagctacga cggggactcc agaagtccat ctcccgaaca    120
gcagcggggc gaaaagaaag aaaaagggtt tccgaagact cctactcaca cccacgcttt    180
cccttaaccc ggaagtgatt tccgcccctc ctctccctct tcggttgata ctggaggaga    240
aggacggcca ggtctggccc ggcatgccct gggcttccgg tgacctctgg ccctttctg     300 tcgtccgctc tctctgccta gcgtgctcgc tcgctcattg ctttccttcc ctccctcggt    360
cttccttcgc acgctgtttg gtgattgtgg cgctcgcgac agacagggag gcggtggcag    420
aggacacttg tcatggccgc ctctaaacct gtggaggcag cggtggtcgc agccgctgta    480
ccgagctccg ggagtggggt gggcggcggc gggactgcgg gcccgggcac ggggggggctg    540 ccgcgatggc agctggctct ggcggtcggg gcaccctgc  tgctgggcgc gggtgccata    600
tacctgtgga gtcggcagca acggcgccgg gaggccagag gccggggcga cgccagcggc    660
ctgaagcgca acagcgaacg gaagaccccg gagggcaggg ccagtccggc cccgggcagc    720
ggacaccctg aaggtccgg  tgctcacttg gacatgaact ctcttgatag agcccaagca    780
gccaagaata aaggcaataa atattttaaa gcaggaaaat atgaacaagc tattcagtgc    840
tatactgagg ctattagctt gtgccctaca gagaagaatg ttgacctttc tacatttat     900 caaaacagag ctgctgcctt tgaacagttg caaaaatgga agaagtggc  acaagactgt    960 acaaagctg  ttgaacttaa tcccaaatat gtgaaagctc tctttagacg tgcaaaagcc   1020
catgagaagc tagacaataa gaaggaatgt ttagaagatg tcactgctgt gtgtatatta   1080
gaagggttcc aaaatcaaca aagcatgctg ttagccgata aagttcttaa actccttgga   1140
aaagagaaag ccaagaaaaa atataagaat cgtgaacctc tgatgccatc tccacagttt   1200
atcaaatctt acttcagttc tttcacggat gatatcattt cccagcccat gcttaaagga   1260
gagaaatctg atgaagataa agacaaggaa ggggaggctt tagaagtgaa agaaaattct   1320
ggatacttaa aggccaaaca gtatatggaa gaagaaaact acgataaaat cataagtgaa   1380
tgctcaaaag aaaatagatgc tgaaggcaaa tacatgcag  aagcattgct actacgagct   1440
accttctacc tgcttattgg caatgccaat gcagccaaac cagatttaga taaagtcatc   1500
agtttgaaag aagctaatgt gaagcttcga gcaaatgctc tcatcaaaag aggcagcatg   1560
tacatgcaac agcagcagcc tttgctgtcc actcaagatt ttaacatggc tgctgacatc   1620
```

```
gatcctcaga atgcagatgt ttatcaccac cgaggacagc tgaaaatact ccttgatcaa    1680
gttgaagaag cagtggcaga ttttgatgaa tgtattaggt taagacctga gtctgctctg    1740
gcacaagcac agaaatgttt tgcattgtac cgccaggcat atacgggaaa caactcttca    1800
caaatccaag cagctatgaa aggttttgaa gaggtcataa agaaatttcc aaggtgtgcc    1860
gaaggctatg cactatacgc ccaggcatta acagatcaac aacagtttgg taaagctgat    1920
gaaatgtatg ataaatgtat tgatttggaa ccagataatg ctacaacata tgttcataaa    1980
ggtttacttc aacttcagtg gaagcaagat ctggatagag gtttggaact tatcagcaag    2040
gctattgaaa ttgacaataa atgtgatttt gcctatgaaa ccatgggaac tattgaagta    2100
caaagaggaa acatggagaa agccattgac atgttcaaca agctattaa cctggccaaa    2160 tcggaaatgg agatggccca tctgtattca ctttgcgatg ccgcccatgc ccagacagaa    2220
gttgcaaaga aatacggatt aaaaccacca acattataaa acaggggaa agcagactga    2280 ccctcttttt aaagtttac cccctcttca actgaaccct aaagacactg tcatgaactg    2340
tgttgaatgg tggaaatcag tatttctgtt tgtggtgttg ttatttgtta catctgtttc    2400
atgtctaggt gttgtgggtg tggctgttga aggaagtttg cagtcttgca gcttttattc    2460
cctgtgcaac aaaagattag aacatgttaa agggattttt aaataaagtt gcaaagagta    2520
caaatgataa ttggccatgc aaataaaaac tgatttgttg atttttttt taagggggt    2580 tggcagttga ttatgttctg gatgattccg tctatatatg tgtgaataat gtaagtattt    2640
tacagcatgt tgattttaa attaacgtag taaatgctgt aaaatagatt tatattcagt    2700
taaccgcttt cagttgattt tttgaaagaa acaaaggtta aatgggggat taaagtaaaa    2760
ttgagagacc ctttaaacca ttgtcagcat gcacaatgcc tctgattctg cagttttaga    2820
aacttggtgg cacttattaa tcctcttggc cccttttccac tctaatggat agtgtacatt    2880
cttcttaaag tccacaacag cagatttct tgcagtaaat tatgcagatg caaaatattc    2940
taattgatat atgtgttgga agactgagta ttgatggggg agtggaccag acaaagaggt    3000
aagatgaaac agtagtgtgt ttataattgt ctgtgactat tttctataat aattagtact    3060
atttaatggt gagcttttaa aaatgtagga tagagggtac agtggcactg tatatactat    3120
ttatagtctc agctactagg gaggctgagg caagaggctt gagaccagga gctcgaggct    3180
gtaatgtgcc atgatgattg cacctgcgaa tagccactgc actccagcct gggcaatata    3240
gcaagacccc atcctttaaa aaattttaga acttttttaa aatcaaagtg cagattgctt    3300
gtatgtaaaa cccaaataaa ggtagagtaa gtgtgatata tgggagtatt aaaatagctt    3360
aaaatttctc gtgaaggaca tgtggctaaa gggtcaaaaa ggatgtaaga cttggagcca    3420
gagcatagta tttcctgaaa taacaagttt agtgctttaa ctatggctac atgtgcttaa    3480
ggaattttga gccacttatt tttgaagatg ctgaggacat gtagagtgct ttttgtagtg    3540
agctaacctt gatctctaag gactaactac ccaggtccag gtcttcacta ggggtactga    3600
cagtgtttaa gctttactcc acctccttac ttagaaatca ctttacgatt tatttccatt    3660
ttccactttt atagaccatc cttttgctta tatgctagat ttttctggtg agggaagggt    3720
tgtgttcttc aggggtcttt tgttttgaaa tactcaggat ggggagaggt ttatttaaga    3780
acgaattata attatggttt acactgttgg gagtaaagga gcatttttac acccccttaag    3840 ggtgcttaat tctgttgaaa ccaaaaagat ttgtctacaa atgctatctt ttttagaaac    3900
tattagaaat gactcccttt caaagtcaat cctttggaaaa tattgaggag gtcactaatt    3960
agttggtgca gttaatataa ttcaagatga tttggatgat gggaagtttg agaccgctgc    4020
```

-continued

| | |
|---|---|
| attttgtttt taaattatgc accttctgat aaccccccaaa tacagaaatg ttctacatct | 4080 |
| ctgaatgacc tctgactta aaaaagtttt tatttgcatg gctgtattta cattaacact | 4140 |
| gacattttct tctactcttc tcccttcttt catcttgggg ttgggtagag aaacacaaag | 4200 |
| gaaactgaag catgtgccat tctatactgt cattccaaat tctcatggac tattgcctgt | 4260 |
| tgtgaaaatg tttgaaactg cactgaaagc tgcatctgtc tgtatctttc ttttgtaaat | 4320 |
| gacctcacat gtaaattcac caaataaata ttacattcaa aaaaaaaaaa aaaaaa | 4376 |

<210> SEQ ID NO 8
<211> LENGTH: 3819
<212> TYPE: DNA
<213> ORGANISM: Homo sapiens

<400> SEQUENCE: 8

| | |
|---|---|
| tttttcatg ttaagagcaa gaaggctttt gttcttggag caggcagaga gtattgtaca | 60 |
| ttcttttggc cgaggaaaca gaatgagctg cgacagtctt aaggacaaac atttgtgaaa | 120 |
| ccgatctgct cctccgtata aaggacatca gtcatttctt aatgcaagac atcgccttct | 180 |
| tgtctggtgg ccggggaaag gacaatgctt ggatcattac gtttccagaa aactgtaatt | 240 |
| ttagatgtat accagaggaa gtaatagcaa aagtacttac ttacctgaca tctattgcaa | 300 |
| ggcaaaatgg atcagactcc cggtttacca ttattctgga tcgaagattg gatacatggt | 360 |
| cttctctcaa aatctctctc caaaaaatct cggcttcctt ccctgggaac ttgcacttgg | 420 |
| ttttggtttt acgtcctacc agcttttcttc aacgaacgtt cacagacatt ggattttggt | 480 |
| ttagtcagga ggattttatg cttaaattac cagttgttat gctgagctca gttagtgatt | 540 |
| tgctgacata cattgatgac aagcaattaa cccctgagtt aggcggcacc ttgcagtact | 600 |
| gccacagtga atggatcatc ttcagaaatg ctatagaaaa ttttgccctc acagtgaaag | 660 |
| aaatggctca gatgttacag tccttttggaa ctgaactggc tgagacagaa ctaccagatg | 720 |
| atattccctc aatagaagaa attctggcaa ttcgtgctga aaggtatcat ctgttgaaga | 780 |
| atgatattac agctgtaacc aaagaaggaa aaattctgct aacaaatctg gaagtgcctg | 840 |
| acactgaagg agctgtcagt tcaagactag aatgtcatcg gcaaataagt ggtgactggc | 900 |
| aaactattaa taagttgctg actcaagtac atgatatgga aacagctttt gatggatttt | 960 |
| gggaaaaaca tcaattaaaa atggagcagt atctgcaact atggaagttt gagcaggatt | 1020 |
| ttcaacagct tgtgactgaa gttgaattc tattaaacca acaagcagaa ctggctgatg | 1080 |
| taacagggac tatagctcaa gtaaaacaaa aaataaaaaa attggaaaac ttagatgaaa | 1140 |
| attctcagga gctattatca aaggcccagt tgtgatatt acatggacac aagcttgcag | 1200 |
| caaatcacca ttatgcactt gatttaatct gccagaggtg caatgagcta cgttaccttt | 1260 |
| ctgatatttt ggttaatgag ataaaagcaa aacggataca actcagcagg accttcaaaa | 1320 |
| tgcataaact cctacagcag gctcgtcaat gctgtgatga aggggaatgt cttctagcta | 1380 |
| atcaggaaat agataagttt cagtctaaag aagatgctca gaaagctctc caagacattg | 1440 |
| aaaattttct tgaaatggct ctacccttta taaattatga acctgaaaca ctgcagtatg | 1500 |
| aatttgatgt aatattatct cctgagctta aggttcaaat gaagactata caactcaagc | 1560 |
| ttgaaaacat tcgaagtata tttgagaacc agcaggctgg tttcaggaac ctggcagata | 1620 |
| agcatgtgag gccaatccaa tttgtggtac ccacacctga aatttggtc acatctggga | 1680 |
| caccattttt ttcatctaaa caagggaaga agacttggag acaaaatcag agcaacttaa | 1740 |
| aaattgaagt ggtgcctgat tgtcaggaga agagaagttc tggtccatcc tccagtttgg | 1800 |

```
acaatggcaa tagcttggat gttttaaaga accacgtact aaatgaactg atacagactg    1860
agagagttta tgttcgagaa ctgtatactg ttttgttggg ttatagagcg gagatggata    1920
atccagagat gtttgatctt atgccacctc tcctgagaaa taaaaaggac attctctttg    1980
gaaacatggc agaaatatat gaattccata acgacatttt cttgagcagc ctggaaaatt    2040
gtgctcatgc tccagaaaga gtgggacctt gtttcctgga aaggaaggat gattttcaga    2100
tgtatgcaaa atattgtcag aataagccca gatcagaaac aatttggagg aagtattcag    2160
aatgcgcatt tttccaggaa tgtcaaagaa agttaaaaca cagacttaga ctggattcct    2220
atttactcaa accagtgcaa cgaatcacta aatatcagtt attgttgaag gagctattaa    2280
aatatagcaa agactgtgaa ggatctgctc tgttgaagaa ggcactcgat gcaatgctgg    2340
atttactgaa gtcagttaat gattctatgc atcagattgc aataaatggc tatattggaa    2400
acttaaatga actgggcaag atgataatgc aaggtggatt cagcgtttgg atagggcaca    2460
agaaaggtgc tacaaaaatg aaggatttgg ctagattcaa accaatgcag cgacacccttt    2520 tcttgtatga aaaagccatt gttttttgca aaaggcgtgt tgaaagtgga gaaggctctg    2580
acagataccc gtcatacagt tttaaacact gttggaaaat ggatgaagtt ggaatcactg    2640
aatatgtaaa aggtgataac cgcaagtttg aaatctggta tggtgaaaag gaagaagttt    2700
atattgtcca ggcttctaat gtagatgtga agatgacgtg gctaaaagaa ataagaaata    2760
ttttgttgaa gcagcaggaa cttttgacag ttaaaaaaag aaagcaacag gatcaattaa    2820
cagaacggga taagtttcag atttctcttc agcagaatga tgaaaagcaa cagggagctt    2880
ttataagtac tgaggaaact gaattggaac acaccagcac tgtggtggag gtctgtgagg    2940
caattgcgtc agttcaggca gaagcaaata cagtttggac tgaggcatca caatctgcag    3000
aaatctctga agaacctgcg gaatggtcaa gcaactattt ctaccctact tatgatgaaa    3060
atgaagaaga aaataggccc ctcatgagac ctgtgtcgga gatggctctc ctatattgat    3120
gaagctacta tgtcaaatgg caagtagctc tttcctgcct gcttctcagc tcatttggaa    3180
aaatactgcg caaaagacat tgagctcaaa tgatgcagat gttgttttca ggttaatgga    3240
cacgcaaaga aaccacagca catacttctt ttctttcatt taataaagct tttaattatg    3300
gtacgctgtc ttttttaaaat catgtattta atgtgtcaga tattgtgctt gaaagattct    3360
catctcagaa tacttttgga cttgaaaatt atttcttctc tactttgtaa ccaaatgcaa    3420
tcggtgtgcc ttggattatt tagtttatta atgaattaag tcaaaattac ggctgcaaaa    3480
tggctaaggt caagtaaagc acaacattat gatttaatat gcttttgttg aaaccacagc    3540
ttttgtgccc attgttttaa cttgtgtgaa acaatacaaa gcccagaaat tcttttcggg    3600
gcatgagtaa attttgttca gggctactgt ctgtatgtgc ccagataaaa ttttcatgag    3660
agtagtttac aaaagccgta tttaaaagtt aatattttca cacttttttt ctggatttct    3720
gcttataatt aatgtaactt aaattagttg tgctctgcta ttttctgtat atttcatgtt    3780
gtaattcttt ttttcaaata aaattaatt cttcaggtt                             3819

<210> SEQ ID NO 9
<211> LENGTH: 3772
<212> TYPE: DNA
<213> ORGANISM: Homo sapiens

<400> SEQUENCE: 9
agcacaagct aatccacaag gttcaatcag gctaagtaat tggaggaatg tgttaactct      60
gaattacaag gagcagaagg gaaggatctg tcagctgact aatcagggat agtggttttt    120
```

```
tttttttttt cctccccagc attgctgcca ctgtgctaat ggaagcagcc acggcagctt      180
tgtttgatag agattttggg ctgccgtttt taaatactac ccaagaagca gctcgtattt      240
catcaacgtt gcgttgacaa ttggaaaaga aaagtgtaat tgcgtacagg cgaaatggca      300
gaagcaaatc cccggagagg caagatgagg ttcagaagga atgcggcttc cttccctggg      360
aacttgcact tggttttggt tttacgtcct accagctttc ttcaacgaac gttcacagac      420
attggatttt ggtttagtca ggaggatttt atgcttaaat taccagttgt tatgctgagc      480
tcagttagtg atttgctgac atacattgat gacaagcaat taaccsctga gttaggcggc      540
accttgcagt actgccacag tgaatggatc atcttcagaa atgctataga aaattttgcc      600
ctcacagtga aagaaatggc tcagatgtta cagtcctttg gaactgaact ggctgagaca      660
gaactaccag atgatattcc ctcaatagaa gaaattctgg caattcgtgc tgaaaggtat      720
catctgttga agaatgatat tacagctgta accaaagaag gaaaaattct gctaacaaat      780
ctggaagtgc ctgacactga aggagctgtc agttcaagac tagaatgtca tcggcaaata      840
agtggtgact ggcaaaactat taataagttg ctgactcaag tacatgatat ggaaacagct      900
tttgatggat tttgggaaaa acatcaatta aaaatggagc agtatctgca actatggaag      960
tttgagcagg attttcaaca gcttgtgact gaagttgaat ttctattaaa ccaacaagca     1020
gaactggctg atgtaacagg gactatagct caagtaaaac aaaaaataaa aaaattggaa     1080
aacttagatg aaaattctca ggagctatta tcaaaggccc agtttgtgat attacatgga     1140
cacaagcttg cagcaaatca ccattatgca cttgatttaa tctgccagag gtgcaatgag     1200
ctacgttacc tttctgatat tttggttaat gagataaaag caaaacggat acaactcagc     1260
aggaccttca aaatgcataa actcctacag caggctcgtc aatgctgtga tgaaggggaa     1320
tgtcttctag ctaatcagga aatagataag tttcagtcta agaagatgc tcagaaagct     1380 ctccaagaca ttgaaaattt tcttgaaatg gctctaccct ttataaatta tgaacctgaa     1440
acactgcagt atgaatttga tgtaatatta tctcctgagc ttaaggttca aatgaagact     1500
atacaactca gcttgaaaaa cattcgaagt atatttgaga accagcaggc tggtttcagg     1560
aacctggcag ataagcatgt gaggccaatc caatttgtgg tacccacacc tgaaaatttg     1620
gtcacatctg gacaccatt ttttcatct aaacaaggga agaagacttg gagacaaaat     1680
cagagcaact taaaaattga agtggtgcct gattgtcagg agaagagaag ttctggtcca     1740
tcctccagtt tggacaatgg caatagcttg gatgttttaa agaaccacgt actaaatgaa     1800
ctgatacaga ctgagagagt ttatgttcga gaactgtata ctgttttgtt gggttataga     1860
gcggagatgg ataatccaga gatgtttgat cttatgccac ctctcctgag aaataaaaag     1920
gacattctct ttggaaacat ggcagaaata tatgaattcc ataacgacat tttcttgagc     1980
agcctggaaa attgtgctca tgctccagaa agagtgggac cttgtttcct ggaaaggaag     2040
gatgattttc agatgtatgc aaaatattgt cagaataagc ccagatcaga aacaatttgg     2100
aggaagtatt cagaatgcgc atttttccag gaatgtcaaa gaaagttaaa acacagactt     2160
agactggatt cctatttact caaaccagtg caacgaatca ctaaatatca gttattgttg     2220
aaggagctat taaatatag caaagactgt gaaggatctg ctctgttgaa gaaggcactc     2280
gatgcaatgc tggatttact gaagtcagtt aatgattcta tgcatcagat tgcaataaat     2340
ggctatattg gaaacttaaa tgaactgggc aagatgataa tgcaaggtgg attcagcgtt     2400
tggatagggc acaagaaagg tgctacaaaa atgaaggatt tggctagatt caaaccaatg     2460
cagcgacacc ttttcttgta tgaaaaagcc attgtttttt gcaaaaggcg tgttgaaagt     2520
```

| ggagaaggct ctgacagata cccgtcatac agtttttaaac actgttggaa aatggatgaa | 2580 |
| gttggaatca ctgaatatgt aaaaggtgat aaccgcaagt ttgaaatctg gtatggtgaa | 2640 |
| aaggaagaag tttatattgt ccaggcttct aatgtagatg tgaagatgac gtggctaaaa | 2700 |
| gaaataagaa atattttgtt gaagcagcag gaacttttga cagttaaaaa aagaaagcaa | 2760 |
| caggatcaat taacagaacg ggataagttt cagatttctc ttcagcagaa tgatgaaaag | 2820 |
| caacagggag cttttataag tactgaggaa actgaattgg aacacaccag cactgtggtg | 2880 |
| gaggtctgtg aggcaattgc gtcagttcag gcagaagcaa atacagtttg gactgaggca | 2940 |
| tcacaatctg cagaaatctc tgaagaacct gcggaatggt caagcaacta tttctaccct | 3000 |
| acttatgatg aaaatgaaga agaaaatagg cccctcatga gacctgtgtc ggagatggct | 3060 |
| ctcctatatt gatgaagcta ctatgtcaaa tggcaagtag ctctttcctg cctgcttctc | 3120 |
| agctcatttg gaaaaatact gcgcaaaaga cattgagctc aaatgatgca gatgttgttt | 3180 |
| tcaggttaat ggacacgcaa agaaaccaca gcacatactt ctttctttc atttaataaa | 3240 |
| gcttttaatt atggtacgct gtcttttttaa aatcatgtat ttaatgtgtc agatattgtg | 3300 |
| cttgaaagat tctcatctca gaatactttt ggacttgaaa attatttctt ctctactttg | 3360 |
| taaccaaatg caatcggtgt gccttggatt atttagttta ttaatgaatt aagtcaaaat | 3420 |
| tacggctgca aaatggctaa ggtcaagtaa agcacaacat tatgatttaa tatgcttttg | 3480 |
| ttgaaaccac agcttttgtg cccattgttt taacttgtgt gaaacaatac aaagcccaga | 3540 |
| aattcttttc ggggcatgag taaatttttgt tcagggctac tgtctgtatg tgcccagata | 3600 |
| aaattttcat gagagtagtt tacaaaagcc gtatttaaaa gttaatatttt tcacacttttt | 3660 |
| tttctggatt tctgcttata attaatgtaa cttaaattag ttgtgctctg ctattttctg | 3720 |
| tatatttcat gttgtaattc tttttttcaa ataaaaatta attcttcagg tt | 3772 |

```
<210> SEQ ID NO 10
<211> LENGTH: 2673
<212> TYPE: DNA
<213> ORGANISM: Homo sapiens

<400> SEQUENCE: 10
```

| cccattctcc tctgcgcggc ctccatctaa gatctcttcc ccttgtccat agcctagatc | 60 |
| gagctccctg tgtgcaccgc gcgctgcccg aggcgcaggt caaccagaat caagatgtct | 120 |
| gggactgagg aagcaattct tggaggacgt gacagccatc ctgctgctgg cggcggctca | 180 |
| gtgttatgct ttggacagtg ccagtacaca gcagaagagt accaggccat ccagaaggcc | 240 |
| ctgaggcaga ggctgggccc agaatacata agtagccgca tggctggcgg aggccagaag | 300 |
| gtgtgctaca ttgagggtca tcgggtaatt aatctggcca atgagatgtt tggttacaat | 360 |
| ggctgggcac actccatcac gcagcagaat gtggattttg ttgacctcaa caatggcaag | 420 |
| ttctacgtgg gagtctgtgc atttgtgagg gtccagctga aggatggttc atatcatgaa | 480 |
| gatgttggtt atggtgttag tgagggcctc aagtccaagg ctttatcttt ggagaaggca | 540 |
| aggaaggagg cggtgacaga cgggctgaag cgagccctca ggagttttgg gaatgcactt | 600 |
| ggaaactgta ttctggacaa agactacctg agatcactaa ataagcttcc acgccagttg | 660 |
| cctcttgaag tggatttaac taaagcgaag agacaagatc ttgaaccgtc tgtggaggag | 720 |
| gcaagataca acagctgccg accgaacatg gccctgggac acccacagct gcagcaggtg | 780 |
| acctcccctt ccagacccag ccatgctgtg ataccggcgg accaggactg cagctcccga | 840 |
| agcctgagct catccgccgt ggagagcgag gccacgcacc agcggaagct ccggcagaag | 900 |

| | |
|---|---|
| cagctgcagc agcagttccg ggagcggatg gagaagcagc aggttcgagt ctccacgccg | 960 |
| tcagctgaga agagtgaggc agcgcctccg gcccctcctg tgacgcacag cactcctgta | 1020 |
| actgtctcag aaccactcct ggagaaagac ttccttgcag gagtgactca agaattaatc | 1080 |
| aagactcttg aagacaactc tgaaaagtgg gctgtgactc ccgatgcagg ggatggtgtg | 1140 |
| gtcaagccct cgtctagagc agacccagcc cagacctctg acacattagc cttgaacaac | 1200 |
| cagatggtga cccagaacag gactccacac agcgtttgcc accagaaacc acaagcaaaa | 1260 |
| tctggatctt gggacctcca aacttatagc gctgaccaac gcaacagg aaactgggaa | 1320 |
| tctcatagga gagccagga catgaagaaa aggaaatatg atccatctta actgaggctc | 1380 |
| aggccacata attggactct gtcacaaagg gactttggaa aactactttt tggtcatgaa | 1440 |
| attgttcatc gctgctggag aatgaacgtc attgcgattt atcttgcttc attctgaacc | 1500 |
| ttatcaagag gatctgactg agagcccact gcagttagag ctgagcactt ttgaaaagct | 1560 |
| tgtccatcac tctagtaggg agaggctctg gacagatgaa tacctttcct tcggcttgtg | 1620 |
| aggcttccca ctatttatta ctgaactatt atgttaatga agatggacat tttaggaatc | 1680 |
| accaatggct ccttgccctc aagcaatata ggccagactt ggtcctaagc acctgcctca | 1740 |
| gcaattgtct acattcagtt gttttgcata acgtctgcct tctttccttt acggtccatg | 1800 |
| cctttaatgt tgcccacatt aagcactgtg gatcacgaca ggaaaaaggt tggagcagtg | 1860 |
| cttttcacta ctttgtatca atccaggcta caatcttcat ttaatataaa taatttatgg | 1920 |
| atttatgaca ttacaatcct gcattgtttc aagactgaca tttttttccta aggaaggaaa | 1980 |
| taatcatcta agaccacgaa aaaaggctgt tttttgtttt ttttttttttt tttttttttg | 2040 |
| agacggggtc tggctgtgtt gccctgactg gagttcagtg gtgcaaacac agctctctcc | 2100 |
| acaacctctt gggcccaagt gatactccca cctctgcctt acaaaataca gggattactg | 2160 |
| gtgtgagcca ctgtgtctgg ccagaaaagg cattttttgag aaagcaaatc gtataccta | 2220 |
| ttaacaaaat agaatatata tatattgctt atctgaaatg cttgaaacca gaattgtttt | 2280 |
| gcatttttg aatatttgta tacacataat gagaccttgg ggatgggacc caagtctgaa | 2340 |
| cgtggaattc acctgtgttt cgtgtatatg cctcatacac ataattttgt gcatgaaaca | 2400 |
| gagttttttgt ataagaagat acactgcagc tgaagagggc tgggtttttt tttctcttag | 2460 |
| ggtcgctgca taaactgttg tatgcctggt gctttgcgac ttgtcacacg aggtcacgtg | 2520 |
| tggaattttc cacttctggc atcacgtcag tgctcagaaa ttttctgatc tcagagcatt | 2580 |
| tcaattaggg atgctcaaac gcaactgttt ctacttcccc atttcaggtg tgagatgtaa | 2640 |
| cccaccttga ccataaattg gcttttcata gtg | 2673 |

<210> SEQ ID NO 11
<211> LENGTH: 3453
<212> TYPE: DNA
<213> ORGANISM: Homo sapiens

<400> SEQUENCE: 11

| | |
|---|---|
| acttttcgcg cgaaacctgg ttgttgctgt agtggcggag aggatcgtgg tactgctatg | 60 |
| gcggaatcat cggaatcctt caccatggca tccagcccgg cccagcgtcg gcgaggcaat | 120 |
| gatcctctca cctccagccc tggccgaagc tcccggcgta ctgatgccct cacctccagc | 180 |
| cctggccgtg accttccacc atttgaggat gagtccgagg ggctcctagg cacagagggg | 240 |
| cccctggagg aagaagagga tgagaggag ctcattggag atggcatgga aagggactac | 300 |
| cgcgccatcc cagagctgga cgcctatgag gccgagggac tggctctgga tgatgaggac | 360 |

```
gtagaggagc tgacggccag tcagagggag gcagcagagc gggccatgcg gcagcgtgac      420
cgggaggctg gccggggcct gggccgcatg cgccgtgggc tcctgtatga cagcgatgag      480
gaggacgagg agcgccctgc ccgcaagcgc cgccaggtgg agcgggccac ggaggacggc      540
gaggaggacg aggagatgat cgagagcatc gagaacctgg aggatctcaa aggccactct      600
gtgcgcgagt gggtgagcat ggcgggcccc cggctggaga tccaccaccg cttcaagaac      660
ttcctgcgca ctcacgtcga cagccacggc cacaacgtct tcaaggagcg catcagcgac      720
atgtgcaaag agaaccgtga gagcctggtg gtgaactatg gggacttggc agccagggag      780
cacgtgctgg cctacttcct gcctgaggca ccggcggagc tgctgcagat ctttgatgag      840
gctgccctgg aggtggtact ggccatgtac cccaagtacg accgcatcac caaccacatc      900
catgtccgca tctcccacct gcctctggtg gaggagctgc gctcgctgag gcagctgcat      960
ctgaaccagc tgatccgcac cagtggggtg gtgaccagct gcactggcgt cctgccccag     1020
ctcagcatgg tcaagtacaa ctgcaacaag tgcaatttcg tcctgggtcc tttctgccag     1080
tcccagaacc aggaggtgaa accaggctcc tgtcctgagt gccagtcggc cggccccttt     1140
gaggtcaaca tggaggagac catctatcag aactaccagc gtatccgaat ccaggagagt     1200
ccaggcaaag tggcggctgg ccggctgccc cgctccaagg acgccattct cctcgcagat     1260
ctggtggaca gctgcaagcc aggagacgag atagagctga ctggcatcta tcacaacaac     1320
tatgatggct ccctcaacac tgccaatggc ttccctgtct tgccactgt catcctagcc      1380 aaccacgtgg ccaagaagga caacaaggtt gctgtagggg aactgaccga tgaagatgtg     1440
aagatgatca ctagcctctc caaggatcag cagatcggag agaagatctt tgccagcatt     1500
gctccttcca tctatggtca tgaagacatc aagagaggcc tggctctggc cctgttcgga     1560
ggggagccca aaaacccagg tggcaagcac aaggtacgtg gtgatatcaa cgtgctcttg     1620
tgcggagacc ctggcacagc gaagtcgcag tttctcaagt atattgagaa agtgtccagc     1680
cgagccatct tcaccactgg ccaggggcg tcggctgtgg gcctcacggc gtatgtccag     1740
cggcaccctg tcagcaggga gtggaccttg gaggctgggg ccctggttct ggctgaccga     1800
ggagtgtgtc tcattgatga atttgacaag atgaatgacc aggacagaac cagcatccat     1860
gaggccatgg agcaacagag catctccatc tcgaaggctg gcatcgtcac ctccctgcag     1920
gctcgctgca cggtcattgc tgccgccaac cccataggag ggcgctacga cccctcgctg     1980
actttctctg agaacgtgga cctcacagag cccatcatct cacgctttga catcctgtgt     2040
gtggtgaggg acaccgtgga cccagtccag gacgagatgc tggcccgctt cgtggtgggc     2100
agccacgtca gacaccaccc cagcaacaag gaggaggagg ggctggccaa tggcagcgct     2160
gctgagcccg ccatgcccaa cacgtatggc gtggagcccc tgccccagga ggtcctgaag     2220
aagtacatca tctacgccaa ggagagggtc caccccgaag ctcaaccagat ggaccaggac     2280 aaggtggcca agatgtacag tgacctgagg aaagaatcta tggcgacagg cagcatcccc     2340
attacggtgc ggcacatcga gtccatgatc cgcatggcgg aggcccacgc gcgcatccat     2400
ctgcgggact atgtgatcga gacgacgtc aacatggcca tccgcgtgat gctggagagc     2460
ttcatagaca cacagaagtt cagcgtcatg cgcagcatgc gcaagacttt tgcccgctac     2520
cttttcattc cggcgtgaca acaatgagctg ttgctcttca tactgaagca gttagtggca     2580
gagcaggtga catatcagcg caaccgcttt ggggcccagc aggacactat tgaggtccct     2640
gagaaggact tggtggataa ggctcgtcag atcaacatcc acaacctctc tgcattttat     2700
gacagtgagc tcttcaggat gaacaagttc agccacgacc tgaaaaggaa aatgatcctg     2760
```

| | |
|---|---|
| cagcagttct gaggccctat gccatccata aggattcctt gggattctgg tttggggtgg | 2820 |
| tcagtgccct ctgtgctttta tggacacaaa accagagcac ttgatgaact cggggtacta | 2880 |
| gggtcagggc ttatagcagg atgtctggct gcacctggca tgactgtttg tttctccaag | 2940 |
| cctgctttgt gcttctcacc tttggtgggg atgccttgcc agtgtgtctt acttggttgc | 3000 |
| tgaacatctt gccacctccg agtgcttttgt ctccactcag taccttggat cagagctgct | 3060 |
| gagttcagga tgcctgcgtg tggtttaggt gttagccttc ttacatggat gtcaggagag | 3120 |
| ctgctgccct cttggcgtga gttgcgtatt caggctgctt ttgctgcctt tggccagaga | 3180 |
| gctggttgaa gatgtttgta atcgttttca gtctcctgca ggtttctgtg ccctgtggt | 3240 |
| ggaagagggc acgacagtgc cagcgcagcg ttctgggctc ctcagtcgca ggggtgggat | 3300 |
| gtgagtcatg cggattatcc actcgccaca gttatcagct gccattgctc cctgtctgtt | 3360 |
| tccccactct cttatttgtg cattcggttt ggtttctgta gttttaattt ttaataaagt | 3420 |
| tgaataaaat ataaaaaaaa aaaaaaaaaa aaa | 3453 |

<210> SEQ ID NO 12
<211> LENGTH: 1839
<212> TYPE: DNA
<213> ORGANISM: Homo sapiens

<400> SEQUENCE: 12

| | |
|---|---|
| atgtggctgg accgccgcgg atggctcagg gttcttggac attggcgcta cgaccttagg | 60 |
| cgccctagct ttaccaggac ttggagtggc gataagggcc caatggcaga aacagtgtct | 120 |
| acccaggttg ggacagaggg cgggctgagg gcttcgcatc agcaaaacgg tgacgctggt | 180 |
| ggcgacgcga aggttgagct gtcccccggg ccccgaagc cggctggccg ggaagtggag | 240 |
| ccggccccag taggcgggga gcatccctcg gctgcagccc caggcccggg caagcataag | 300 |
| aagcggcggg gcgcaaccag ggagcgtgtc gtgccgcccc cgaagaagcg gcggaccggg | 360 |
| gtgagcttcg gagatgagca cttttgcagaa accagttatt acttcgaggg cggcctgcgt | 420 |
| aaggtgcggc cctattactt tgacttccgg acctactgca aaggtcgctg ggtgggccac | 480 |
| agcttgctgc acgtcttcag taccgagttc cgagctcagc ccctggccta ctatgaggcc | 540 |
| gcggtccggg cgggccgcct gcaactcaac gagaagccgg tgcaggacct caacatcgtg | 600 |
| ctcaaggaca atgatttctt gcggaacaca gtgcacaggc atgagccacc agtcacagca | 660 |
| gagcccattc gcctgctagc tgagaacgaa gatgtggtgg ttgtagacaa gccttcctcc | 720 |
| attcccgttc accccgtgtgg ccgcttccga cacaaacacag tcatcttcat cctaggcaag | 780 |
| gagcaccaac tcaaggagct acacccccttg catcggcttg accgccttac ctcaggggtg | 840 |
| cttatgtttg ccaagacagc tgcagtctct gagagaattc acgagcaggt tcgggaccgg | 900 |
| cagctggaga aggagtacgt gtgccgggtg aagggagt tccccactga ggaagtgacc | 960 |
| tgtaaagaac ccatcttagt ggtgtcttac aaagtagggg tgtgccgtgt agatccccgg | 1020 |
| ggcaagccct gtgagacagt gttccagagg ctaagctaca atggccagtc cagtgtggta | 1080 |
| cggtgccggc cactcacagg ccgcacacac cagattcgag tccaccttca gttcttgggc | 1140 |
| catcccattc tcaacgaccc catctacaac tcagttgcct ggggtccttc tcgaggccgg | 1200 |
| ggcggctaca ttcccaagac aaacgaggag ttgctacggg acctggtagc agagcaccag | 1260 |
| gccaaacaga gcctggatgt gctagatctc tgtgagggtg acctgtcccc aggactcaca | 1320 |
| gactctacgg ccccctcctc agagtttgggc aaggacgacc tggaagagtt ggctgcagct | 1380 |
| gcccagaaga tggaggaagt agctgaggca gcccctcagg agttggacac aatagccttg | 1440 |

```
gcatcagaga aggcagttga aacagatgtc atgaatcaag agacagaccc actctgtgca    1500
gagtgccggc tggtgcgaca ggatcccttg ccccaagacc ttgtgatgtt cctacatgcc    1560
ctacgctata aagggccagg ctttgagtac ttttcaccaa tgcctgcctg ggcacaggat    1620
gactggcaaa aggactgagg gtgtggccaa tggagggatt gcttcttggg ttgtgacaag    1680
gatgggctat agggcaaggg ctgaccccat gggctagtac ttggggtttc ataggaatg     1740 aggacgggct tctaaagaga cctgctcata cttgctacct ccttccagtg ggaatttgga    1800
gacttttggg tttgtaaata tatccctttt tctaacatc                           1839

<210> SEQ ID NO 13
<211> LENGTH: 3513
<212> TYPE: DNA
<213> ORGANISM: Homo sapiens

<400> SEQUENCE: 13
aggcaggggc ggtgcggggg cgtgggcagc acaagccgtg cgctcccggg ctgcgaggtc      60
tggctaggct acgggccacg cgccgccgcc gctgccgccg ccactgtcct cttcggaggc     120
gcgggcccga cggaaaccat gtttgtggct cgcagcatcg cggcggacca caaggatctc     180
atccacgatg tctcttttcga cttccacggg cggcggatgg caacctgctc cagcgatcag    240
agcgttaagg tctgggataa aagtgaaagt ggtgattggc attgtactgc tagctggaag    300
acacatagtg gatctgtatg gcgtgtgaca tgggcccatc ctgaatttgg gcaggttttg    360
gcttcctgtt cttttgaccg aacagctgct gtatgggaag aaatagtagg agaatcaaat    420
gataaactgc gaggacagag ccactgggtt aaaaggacaa ctctggtgga tagcagaaca    480
tctgttactg atgtgaagtt tgctcccaag cacatgggtc ttatgttagc aacctgttcc    540
gcagatggta tagtaagaat ctatgaggca ccagatgtta tgaatctcag ccagtggtct    600
ttgcagcatg agatctcatg taagctaagc tgtagttgta tttcttggaa cccttcaagc    660
tctcgtgctc attcccccat gatcgccgta ggaagtgatg acagtagccc caacgcaatg    720
gccaaggttc agattttga atataatgaa acaccagga aatatgcaaa agctgaaact     780
cttatgacag tcactgatcc tgttcatgat attgcattcg ctccaaattt gggaagatct    840
ttccatattc tagcaatagc gaccaaagat gtgagaattt ttacattaaa gcctgtgagg    900
aaagaactga cttcctctgg tgggccaaca agtttgaaa tccatatagt ggctcagttc    960
gataatcata attctcaggt ctggcgagtg agttggaata taacaggaac ggtgctagca   1020
tcttcaggag atgatgggtg tgtaagattg tggaaagcta attatatgga caattggaag   1080
tgtactggta ttttgaaagg taatgggagc ccagtcaatg ggagttctca gcagggaacc   1140
tcaaatcctt ccctaggttc aactattcca agtcttcaga attcattaaa tggatcttct   1200
gctggcagaa agcacagctg agtacaagct aactggagta actttgctgt tttgctgctt   1260
gttgcatgca cacaggaatg gaaagcgagc tccttttccc cttccccagc gccgtttgac   1320
ctctcccaag atacaccagc agcctgctta ctactaaacg caatccaaaa ggcctttaaa   1380
aatacagtgt atatttttg tactagtcag tttattgaca ctatttgaaa cttttgaaat    1440
ataaacggag aggctttctg ttgagacatt gtcaccaaaa caattttttg aaatgttcct   1500
gaaactaatt tgggtttaaa gattaaaagg gttgttacca ttcttatctg agtagttggg   1560
aggaggggaa taccactttta gttcatttgg aaaatataga catatttctt ttgctttctt   1620
aaaacagctt aaaatgatga actttttataa ttttaatttg aagattgaat aaatattttt   1680
tataaagatt gttttgagtg ctgatttgtt tacttttttgt agatttgctt tatccatgat   1740
```

```
attcagtaca actctgtcat ttctttgtaa tatttaaaaa atattagtaa aggagtgaat      1800
taataaagta gtaatagtaa aatgaaagga acttgactgt acagtttgta gccaggttaa      1860
gcatttggta ttgtttcatt tacaatttgg gactaagatg gaaacacttt ttttataagt      1920
ttttaattca tagtcactaa agagataaat gtttcttata tacatttgtg tattttttatg     1980 gtgttattta ttccatggct tagcttcctt caaatcaaaa tttggacaca cactattaag      2040
agaagccatt aaaattttac taaaattgtg catgtaaatt aattgtcagc attccatgtc      2100
tcaagatttt cttaatttag ttcgctgttt aaattaattc atgtcctgta aagttctgac      2160
cttgataaca aagctataaa tatttaagtt tgctaatatg cgtaagtatt atcggtaagt      2220
tacaagatgg aagaagaata acagtagggc acagtcattc tgtgaatcct tttacttatc      2280
aaaatttggt agctattcta aggcttttgc agaaaaataa gtgttcaatg tttgtagttc      2340
ttcaaaagca tgttgcagta gccagccata ctatgtgtat tcccagtatc atgtacgcac      2400
taaaaaaaat gtgtgcttgc tgctgctgtg agtgaaccat tgcttaagat aaaaaactta      2460
actagatctg taaatgtaca gaatagcatc agatgtttct gagagattag aaaatgtttt      2520
gaatttataa aattaatgtt tttctttgta acatttatat atattttta acattttaag      2580 tttaacagat tgtattcctt tcaagtttct atacttgctt aagcaatctt gatttgagta      2640
agggtcttga tttgtgctat tatgttctgt tagttttggc atgaatatac taaagctttt      2700
tttttttttt ctagcatgtg ttttctcctc tttggttctc tttgtattta ctactttttct     2760 cttttcttg tgtttttttt ttcctgtttt tgttttgttt ggtgttttgt tcctgtcttc      2820
attgtttcag gtatttcttt acccctctgg attccccacg ggctggatcg agatggtcca      2880
gttatgccca gctccttcct cctcctcctc ctcctctggt agagcactct tgcgatgctg      2940
acactgccaa cctccagtat cctcacccct gcagacgata tctctctcgg cctcttaatc      3000
ccttacctga gaatgaaggg atttaaaaca ctgatttaac attgaaaggc cttattcaag      3060
tgcttgtaaa tgcttttcatt tctggctgct ttttgttttt catttttcttt cagaagattt      3120 ttctaactta gggtctgtct tgcatgtatt acaaccagaa tacagtgttt ggaacctaaa      3180
tctgtttgtg cgtctgcatc aaaggaacat ttgcttcact gggtgataac ctttgatgaa      3240
atgagatatg tccaagtaac gttaactgtg aagttacaca cagtagctga cttcaaagtg      3300
cctgttctgt aaatttttatt ttaaactgtt accatagtct taagttgttt atgctttatc      3360
agactggcta atgtgaaagc ataatattat gaagtttatt ctgccttatg agaccttaaa      3420
aaatggattt cattttacag gctaatgttg taactgacta gtatgtaaaa taaatcattc      3480
ctgtgtataa agcagcaaaa cctaaaaaaa aaa                                   3513
```

<210> SEQ ID NO 14
<211> LENGTH: 1891
<212> TYPE: DNA
<213> ORGANISM: Homo sapiens

<400> SEQUENCE: 14

```
aggcaggggc ggtgcggggg cgtgggcagc acaagccgtg cgctcccggg ctgcgaggtc        60
tggctaggct acgggccacg cgccgccgcc gctgccgccg ccactgtcct cttcggaggc       120
gcgggcccga cggaaaccat gtttgtggct cgcagcatcg cggcggacca caaggatctc       180
atccacgatg tctcttttcga cttccacggg cggcggatgg caacctgctc cagcgatcag       240
agcgttaagg tctgggataa aagtgaaagt ggtgattggc attgtactgc tagctggaag       300
acacatagtg gatctgtatg gcgtgtgaca tgggcccatc ctgaatttgg gcaggttttg       360
```

```
gcttcctgtt cttttgaccg aacagctgct gtatgggaag aaatagtagg agaatcaaat      420
gataaactgc gaggacagag ccactgggtt aaaaggacaa ctctggtgga tagcagaaca      480
tctgttactg atgtgaagtt tgctcccaag cacatgggtc ttatgttagc aacctgttcc      540
gcagatggta tagtaagaat ctatgaggca ccagatgtta tgaatctcag ccagtggtct      600
ttgcagcatg agatctcatg taagctaagc tgtagttgta tttcttggaa cccttcaagc      660
tctcgtgctc attcccccat gatcgccgta ggaagtgatg acagtagccc caacgcaatg      720
gccaaggttc agattttga atataatgaa acaccagga aatatgcaaa agctgaaact        780
cttatgacag tcactgatcc tgttcatgat attgcattcg ctccaaattt gggaagatct      840
ttccatattc tagcaatagc gaccaaagat gtgagaattt ttacattaaa gcctgtgagg      900
aaagaactga cttcctctgg tgggccaaca aagtttgaaa tccatatagt ggctcagttc      960
gataatcata attctcaggt ctggcgagtg agttggaata taacaggaac ggtgctagca     1020
tcttcaggag atgatgggtg tgtaagattg tggaaagcta attatatgga caattggaag     1080
tgtactggta ttttgaaagg taatgggagc ccagtcaatg ggagttctca gcagggaacc     1140
tcaaatcctt ccctaggttc aactattcca agtcttcaga attcattaaa tggatcttct     1200
gctggcaggt atttctttac ccctctggat tccccacggg ctggatcgag atggtccagt     1260
tatgcccagc tccttcctcc tcctcctcct cctctggtag agcactcttg cgatgctgac     1320
actgccaacc tccagtatcc tcaccctcgc agacgatatc tctctcggcc tcttaatccc     1380
ttacctgaga atgaagggat ttaaaacact gatttaacat tgaaaggcct tattcaagtg     1440
cttgtaaatg ctttcatttc tggctgcttt ttgttttca ttttctttca gaagattttt      1500
ctaacttagg gtctgtcttg catgtattac aaccagaata cagtgtttgg aacctaaatc     1560
tgtttgtgcg tctgcatcaa aggaacattt gcttcactgg gtgataacct ttgatgaaat     1620
gagatatgtc caagtaacgt taactgtgaa gttacacaca gtagctgact tcaaagtgcc     1680
tgttctgtaa attttatttt aaactgttac catagtctta agttgtttat gctttatcag     1740
actggctaat gtgaaagcat aatattatga agtttattct gccttatgag acctaaaaaa     1800
atggatttca ttttacaggc taatgttgta actgactagt atgtaaaata aatcattcct     1860
gtgtataaag cagcaaaacc taaaaaaaaa a                                    1891
```

<210> SEQ ID NO 15
<211> LENGTH: 1242
<212> TYPE: DNA
<213> ORGANISM: Homo sapiens

<400> SEQUENCE: 15

```
cgccccgcag cgccggagtc aaagccggtt cccggcccag tcccgtcctg cagcagtctg       60
cctcctcttt caacatgaca gatgccgctg tgtccttcgc caaggacttc ctggcaggtg      120
gagtggccgc agccatctcc aagacggcgg tagcgcccat cgagcgggtc aagctgctgc      180
tgcaggtgca gcatgccagc aagcagatca ctgcagataa gcaatacaaa ggcattatag      240
actgcgtggt ccgtattccc aaggagcagg gagttctgtc cttctggcgc ggtaacctgg      300
ccaatgtcat cagatacttc cccacccagg ctcttaactt cgccttcaaa gataaataca      360
agcagatctt cctgggtggt gtggacaaga gaacccagtt ttggctctac tttgcaggga      420
atctggcatc gggtggtgcc gcaggggcca catccctgtg ttttgtgtac cctcttgatt      480
ttgcccgtac ccgtctagca gctgatgtgg gtaaagctgg agctgaaagg gaattccgag      540
gcctcggtga ctgcctggtt aagatctaca atctgatgg gattaagggc ctgtaccaag       600
```

```
gctttaacgt gtctgtgcag ggtattatca tctaccgagc cgcctacttc ggtatctatg      660
acactgcaaa gggaatgctt ccggatccca agaacactca catcgtcatc agctggatga      720
tcgcacagac tgtcactgct gttgccgggt tgacttccta tccatttgac actgttcgcc      780
gccgcatgat gatgcagtca gggcgcaaag aactgacat catgtacaca ggcacgcttg       840
actgctggcg gaagattgct cgtgatgaag gaggcaaagc ttttttcaag ggtgcatggt      900
ccaatgttct cagaggcatg ggtggtgctt ttgtgcttgt cttgtatgat gaaatcaaga      960
agtacacata agttatttcc taggattttt cccctgtga acaggcatgt tgtattatat      1020
aacatatctt gagcattctt gacagactcc tggctgtcag tttctcagtg caactatt      1080 actggttgaa atgggaagc aataatattc atctgaccag ttttctctta aagccatttc      1140
catgatgatg atgatgggac tcaattgtat tttttatttc agtcactcct gataaataac      1200
aaatttggag aaataaaaat atctaaaata aattttgtct gc                         1242

<210> SEQ ID NO 16
<211> LENGTH: 2077
<212> TYPE: DNA
<213> ORGANISM: Homo sapiens

<400> SEQUENCE: 16
ccgagcgcca gcgcgggaa ccgggaaaag gaaaccgtgt tgtgtacgta agattcagga       60
aacgaaacca ggagccgcgg gtgttggcgc aaaggttact cccagaccct tttccggctg     120
acttctgaga aggttgcgca cagctgtgcc cggcagtcta gaggcgcaga agaggaagcc     180
atcgcctggc cccggctctc tggaccttgt ctcgctcggg agcggaaaca gcggcagcca     240
gagaactgtt ttaatcatgg acaaacaaaa ctcacagatg aatgcttctc acccggaaac     300
aaacttgcca gttgggtatc ctcctcagta tccaccgaca gcattccaag gacctccagg     360
atatagtggc taccctgggc cccaggtcag ctacccaccc ccaccagccg gccattcagg     420
tcctggccca gctggctttc ctgtcccaaa tcagccagtg tataatcagc cagtatataa     480
tcagccagtt ggagctgcag gggtaccatg gatgccagcg ccacagcctc cattaaactg     540
tccacctgga ttagaatatt taagtcagat agatcagata ctgattcatc agcaaattga     600
acttctggaa gttttaacag ttttgaaac taataacaaa tatgaaatta agaacagctt     660
tggacagagg gtttacttg cagcggaaga tactgattgc tgtacccgaa attgctgtgg      720
gccatctaga cctttacct tgaggattat tgataatatg ggtcaagaag tcataactct      780
ggagagacca ctaagatgta gcagctgttg ttgtccctgc tgccttcagg agatagaaat     840
ccaagctcct cctggtgtac caataggtta tgttattcag acttggcacc catgtctacc     900
aaagtttaca attcaaaatg agaaaagaga ggatgtacta aaaataagtg gtccatgtgt     960
tgtgtgcagc tgttgtggag atgttgattt tgagattaaa tctcttgatg aacagtgtgt    1020
ggttggcaaa atttccaagc actggactgg aattttgaga gaggcattta cagacgctga    1080
taacttggga atccagttcc ctttagacct tgatgttaaa atgaaagctg taatgattgg    1140
tgcctgtttc ctcattgact tcatgttttt tgaaagcact ggcagccagg aacaaaaatc    1200
aggagtgtgg tagtggatta tgaaagtct cctcaggaaa tctgaagtct gtatattgat    1260
tgagactatc taaactcata cctgtatgaa ttaagctgta aggcctgtag ctctggttga    1320
atacttttgc ttttcaaatt atagtttatc ttctgtataa ctgatttata aaggttttg    1380 tacatttttt aatactcatt gtcaatttga gaaaaggac atatgagttt ttgcatttat    1440
taatgaaact tcctttgaaa aactgctttg aattatgatc tctgattcat tgtccatttt    1500
```

-continued

```
actaccaaat attaactaag gccttattaa ttttatata aattatatct tgtcctatta      1560
aatctagtta caatttattt catgcataag agctaatgtt attttgcaaa tgccatatat      1620
tcaaaaaagc tcaaagataa ttttctttac tattatgttc aaataatatt caatatgcat      1680
attatcttta aaaagttaaa tgttttttta atcttcaaga aatcatgcta cacttaactt      1740
ctcctagaag ctaatctata ccataatatt ttcatattca caagatatta aattaccaat      1800
tttcaaatta ttgttagtaa agaacaaaat gattctctcc caaagaaaga cacattttaa      1860
atactcctcc actctaaaac tctggtatta taacttttga aagttaatat ttctacatga      1920
aatgtttagc tcttacactc tatccttcct agaaaatggt aattgagatt actcagatat      1980
taattaaata caatatcata tatatattca cagagtataa acctaaataa tgatctatta      2040
gattcaaata tttgaaataa aaacttgatt tttttgt                               2077
```

<210> SEQ ID NO 17
<211> LENGTH: 3923
<212> TYPE: DNA
<213> ORGANISM: Homo sapiens

<400> SEQUENCE: 17

```
ggcagttagc ccgcccgctc ggcgcagggc gtggcttctc gtagccatta ggaaacagca       60 acccttcac ctcagttttc ttcactccgg catttgcagc agagcgaaag gtggtcgagt       120
cctgaaggag ggcctgatgt cttcatcatt ctcaaattct tgtaagctct gcgtcgggtg      180
aaaccagaca aagccgcgag cccagggatg ggagcacgcg gggacggcc tgccggcggg        240 gacgacagca ttgcgcctgg gtgcagcagt gtgcgtctcg gggaagggaa gatattttaa      300
ggcgtgtctg agcagacggg gaggcttttc caaacccagg cagcttcgtg gcgtgtgcgg      360
tttcgacccg gtcacacaaa gcttcagcat gtcatgtgag gacggtcggg ccctggaagg      420
aacgctctcg gaattggccg cggaaaccga tctgcccgtt gtgtttgtga acagagaaa      480 gataggcggc catggtccaa ccttgaaggc ttatcaggag ggcagacttc aaaagctact      540
aaaaatgaac ggccctgaag atcttcccaa gtcctatgac tatgacctta tcatcattgg      600
aggtggctca ggaggtctgg cagctgctaa ggaggcagcc caatatggca agaaggtgat      660
ggtcctggac tttgtcactc ccacccctct tggaactaga tggggtctcg gaggaacatg      720
tgtgaatgtg ggttgcatac ctaaaaaact gatgcatcaa gcagctttgt taggacaagc      780
cctgcaagac tctcgaaatt atggatggaa agtcgaggag acagttaagc atgattggga      840
cagaatgata gaagctgtac agaatcacat tggctctttg aattggggct accgagtagc      900
tctgcgggag aaaaagtcg tctatgaaa tgcttatggg caatttattg gtcctcacag       960
gattaaggca acaaataata aaggcaaaga aaaaattat tcagcagaga gatttctcat      1020
tgccactggt gaaagaccac gttacttggg catccctggt gacaaagaat actgcatcag      1080
cagtgatgat cttttctcct tgccttactg cccgggtaag accctggttg ttggagcatc      1140
ctatgtcgct ttggagtgcg ctggattct tgctggtatt ggttagacg tcactgttat      1200 ggttaggtcc attcttctta gaggatttga ccaggacatg ccaacaaaa ttggtgaaca      1260 catgaagaa catggcatca agtttataag acagttcgta ccaattaaag ttgaacaaat      1320
tgaagcaggg acaccaggcc gactcagagt agtagctcag tccaccaata gtgaggaaat      1380
cattgaagga gaatataata cggtgatgct ggcaatagga agagatgctt gcacaagaaa      1440
aattggctta gaaaccgtag gggtgaagat aaatgaaaag actggaaaaa tacctgtcac      1500
agatgaagaa cagaccaatg tgccttacat ctatgccatt ggcgatatat tggaggataa      1560
```

```
ggtggagctc acccccagttg caatccaggc aggaagattg ctggctcaga ggctctatgc    1620
aggttccact gtcaagtgtg actatgaaaa tgttccaacc actgtattta ctccctttgga   1680 atatggtgct tgtggccttt ctgaggagaa agctgtggag aagtttgggg aagaaaatat    1740
tgaggtttac catagttact tttggccatt ggaatggacg attccgtcaa gagataacaa    1800
caaatgttat gcaaaaataa tctgtaatac taaagacaat gaacgtgttg tgggcttttca   1860 cgtactgggt ccaaatgctg gagaagttac acaaggcttt gcagctgcgc tcaaatgtgg    1920
actgaccaaa aagcagctgg acagcacaat tggaatccac cctgtctgtg cagaggtatt    1980
cacaacattg tctgtgacca agcgctctgg ggcaagcatc ctccaggctg ctgctgagg     2040 ttaagcccca gtgtggatgc tgttgccaag actgcaaacc actggctcgt ttccgtgccc    2100
aaatccaagg cgaagttttc tagagggttc ttgggctctt ggcacctgcg tgtcctgtgc    2160
ttaccaccgc ccaaggcccc cttggatctc ttggatagga gttggtgaat agaaggcagg    2220
cagcatcaca ctggggtcac tgacagactt gaagctgaca tttggcaggg catcgaaggg   2280
atgcatccat gaagtcacca gtctcaagcc catgtggtag gcggtgatgg aacaactgtc    2340
aaatcagttt tagcatgacc tttccttgtg gattttctta ttctcgttgt caagttttct    2400
agggttgaat tttttttcttt tttctccatg gtgttaatga tattagagat gaaaaacgtt    2460
agcagttgat ttttgtccaa aagcaagtca tggctagagt atccatgcaa ggtgtcttgt    2520
tgcatggaag ggatagtttg gctcccttgg aggctatgta ggcttgtccc gggaaagaga    2580
actgtcctgc agctgaaatg gactgttctt tactgacctg ctcagcagtt tcttctctca    2640
tatattccca aaacaagtac atctgcgatc aactctagcc aaatttgccc ctgtgtgcta    2700
catgatggat gattattatt ttaaggtctg tttaggaagg gaaatggcta cttggccagc    2760
cattgcctgg catttggtag tatagtatga ttctcaccat tatttgtcat ggaggcagac    2820
atacaccaga aatgggggag aaacagtaca tatctttctg tctttagttt attgtgtgct    2880
ggtctaagca agctgagatc atttgcaatg gaaaacacgt aacttgttta aaagttttttc   2940 tggtagcttt agctttatgc taaaaaaaat aatgacattg ggtatctatt tcttttctaag   3000 actacattag taggaaaata agtcttttca tgcttatgat ttagctgttt tgtggtaatt    3060 gcttttttaaa ggaagttatt aatatcataa gttattatta atattttgaa cacaggtgga   3120
tgtgaaggat tttcatttaa aaaccaagtg gttttgactt tttctgttga atgaacaact    3180
gtgccttgtg gaattttttgc agaagtgttt atgctttgtt agcatttcaa cttgcattat    3240
tataaagagg tattaatgcc tcagttatgt gtttgtcaat gtactggctg aggattctat    3300
ctcagctgtc ttttctaact gtgtaggttg agttttgaac acgtgcttgt ggacatcagg    3360
cctcctgcca gcagttcttg aagcttcttt ttcattcctg ctactctacc tgtatttctc    3420
agttgcagca ctgagtggtc aaaatacatt tctgggccac ctcagggaac ccatgcatct    3480
gcctggcatt taggcagcag agcccctgac cgtcccccac agggctctgc ctcacgtcct    3540
catctcattt ggctgtgtaa agaaatggga aagggaaaa ggagagagca attgaggcag     3600
ttgaccatat tcagttttat ttatttattt ttaatttgtt tttttctcca agtccaccag    3660
tctctgaaat tagaacagta ggcggtatga gataatcagg cctaatcatg ttgtgattct    3720
cttttcttag tggagtggaa tgttctatcc ccacaagaag gattatatct tatagacttg    3780
tcttgttcag attctgtatt tacccatttt attgaaacat atactaagtt ccatgtatttt   3840 ttgttacaaa tcttctgaaa aaaacaaaa caatgtgaaa cattaaaatt aaaaggcatt     3900
aataataaaa aaaaaaaaaa aaa                                            3923
```

<210> SEQ ID NO 18
<211> LENGTH: 3859
<212> TYPE: DNA
<213> ORGANISM: Homo sapiens

<400> SEQUENCE: 18

| | | | | | |
|---|---|---|---|---|---|
| ttcccacagg | gccttgtgcg | acatgggctg | cgccgagggc | aaggcagtgg | cggcggccgc | 60 |
| cccaacggag | ctgcagacga | aaggcaagaa | cggcgatggc | cgccgtaggt | cagctaaaga | 120 |
| tcatcaccct | ggtaaaactt | tgccagagaa | cccagcagga | ttcaccagca | cggccactgc | 180 |
| agactccaga | gccctgcttc | aggcctatat | agatggtcac | tctgtggtca | tcttcagtag | 240 |
| gtccacatgc | acacgctgta | ctgaggtaaa | gaagttattt | aaatctctgt | gtgttcctta | 300 |
| ttttgtgctt | gaacttgatc | aaacagagga | cggtcgggcc | ctggaaggaa | cgctctcgga | 360 |
| attggccgcg | gaaaccgatc | tgcccgttgt | gtttgtgaaa | cagagaaaga | taggcggcca | 420 |
| tggtccaacc | ttgaaggctt | atcaggaggg | cagacttcaa | aagctactaa | aaatgaacgg | 480 |
| ccctgaagat | cttcccaagt | cctatgacta | tgaccttatc | atcattggag | gtggctcagg | 540 |
| aggtctggca | gctgctaagg | aggcagccca | atatggcaag | aaggtgatgg | tcctggactt | 600 |
| tgtcactccc | accccctctt | gaactagatg | gggtctcgga | ggaacatgtg | tgaatgtggg | 660 |
| ttgcatacct | aaaaaactga | tgcatcaagc | agctttgtta | ggacaagccc | tgcaagactc | 720 |
| tcgaaattat | ggatggaaag | tcgaggagac | agttaagcat | gattgggaca | gaatgataga | 780 |
| agctgtacag | aatcacattg | gctctttgaa | ttggggctac | cgagtagctc | tgcgggagaa | 840 |
| aaaagtcgtc | tatgagaatg | cttatgggca | atttattggt | cctcacagga | ttaaggcaac | 900 |
| aaataataaa | ggcaaagaaa | aaatttattc | agcagagaga | tttctcattg | ccactggtga | 960 |
| aagaccacgt | tacttgggca | tccctggtga | caaagaatac | tgcatcagca | gtgatgatct | 1020 |
| tttctccttg | ccttactgcc | cgggtaagac | cctggttgtt | ggagcatcct | atgtcgcttt | 1080 |
| ggagtgcgct | ggatttcttg | ctggtattgg | tttagacgtc | actgttatgg | ttaggtccat | 1140 |
| tcttcttaga | ggatttgacc | aggacatggc | caacaaaatt | ggtgaacaca | tggaagaaca | 1200 |
| tggcatcaag | tttataagac | agttcgtacc | aattaaagtt | gaacaaattg | aagcagggac | 1260 |
| accaggccga | ctcagagtag | tagctcagtc | caccaatagt | gaggaaatca | ttgaaggaga | 1320 |
| atataatacg | gtgatgctgg | caataggaag | agatgcttgc | acaagaaaaa | ttggcttaga | 1380 |
| aaccgtaggg | gtgaagataa | atgaaaagac | tggaaaaata | cctgtcacag | atgaagaaca | 1440 |
| gaccaatgtg | ccttacatct | atgccattgg | cgatatattg | gaggataagg | tggagctcac | 1500 |
| cccagttgca | atccaggcag | gaagattgct | ggctcagagg | ctctatgcag | gttccactgt | 1560 |
| caagtgtgac | tatgaaaatg | ttccaaccac | tgtatttact | cctttggaat | atggtgcttg | 1620 |
| tggcctttct | gaggagaaag | ctgtggaaag | gtttgggaa | gaaaatattg | aggtttacca | 1680 |
| tagttacttt | tggccattgg | aatggacgat | tccgtcaaga | gataacaaca | aatgttatgc | 1740 |
| aaaaataatc | tgtaatacta | aagacaatga | acgtgttgtg | ggctttcacg | tactgggtcc | 1800 |
| aaatgctgga | gaagttacac | aaggctttgc | agctgcgctc | aaatgtggac | tgaccaaaaa | 1860 |
| gcagctggac | agcacaattg | gaatccaccc | tgtctgtgca | gaggtattca | acacattgtc | 1920 |
| tgtgaccaag | cgctctgggg | caagcatcct | ccaggctggc | tgctgaggtt | aagccccagt | 1980 |
| gtggatgctg | ttgccaagac | tgcaaaccac | tggctcgttt | ccgtgcccaa | atccaaggcg | 2040 |
| aagttttcta | gagggttctt | gggctcttgg | cacctgcgtg | tcctgtgctt | accaccgccc | 2100 |
| aaggccccct | tggatctctt | ggataggagt | tggtgaatag | aaggcaggca | gcatcacact | 2160 |

```
ggggtcactg acagacttga agctgacatt tggcagggca tcgaagggat gcatccatga      2220
agtcaccagt ctcaagccca tgtggtaggc ggtgatggaa caactgtcaa atcagtttta      2280
gcatgacctt tccttgtgga ttttcttatt ctcgttgtca agttttctag ggttgaattt      2340
ttttcttttt tctccatggt gttaatgata ttagagatga aaaacgttag cagttgattt      2400
ttgtccaaaa gcaagtcatg gctagagtat ccatgcaagg tgtcttgttg catggaaggg      2460
atagtttggc tcccttggag gctatgtagg cttgtcccgg gaaagagaac tgtcctgcag      2520
ctgaaatgga ctgttcttta ctgacctgct cagcagtttc ttctctcata tattcccaaa      2580
acaagtacat ctgcgatcaa ctctagccaa atttgcccct gtgtgctaca tgatggatga      2640
ttattatttt aaggtctgtt taggaaggga aatggctact tggccagcca ttgcctggca      2700
tttggtagta tagtatgatt ctcaccatta tttgtcatgg aggcagacat acaccagaaa      2760
tgggggagaa acagtacata tctttctgtc tttagtttat tgtgtgctgg tctaagcaag      2820
ctgagatcat ttgcaatgga aaacacgtaa cttgtttaaa agttttctg gtagctttag        2880 ctttatgcta aaaaaaataa tgacattggg tatctatttc tttctaagac tacattagta      2940 ggaaataag tcttttcatg cttatgattt agctgttttg tggtaattgc ttttaaagg         3000 aagttattaa tatcataagt tattattaat attttgaaca caggtggatg tgaaggattt      3060
tcatttaaaa accaagtggt tttgactttt tctgttgaat gaacaactgt gccttgtgga      3120
atttttgcag aagtgtttat gctttgttag catttcaact tgcattatta taagaggta       3180 ttaatgcctc agttatgtgt ttgtcaatgt actggctgag gattctatct cagctgtctt      3240
ttctaactgt gtaggttgag ttttgaacac gtgcttgtgg acatcaggcc tcctgccagc      3300
agttcttgaa gcttcttttt cattcctgct actctacctg tatttctcag ttgcagcact      3360
gagtggtcaa aatacatttc tgggccacct cagggaaccc atgcatctgc ctggcattta     3420
ggcagcagag cccctgaccg tcccccacag ggctctgcct cacgtcctca tctcatttgg      3480
ctgtgtaaag aaatgggaaa agggaaaagg agagagcaat tgaggcagtt gaccatattc      3540 agttttatt tatttattttt aatttgtttt tttctccaag tccaccagtc tctgaaatta      3600
gaacagtagg cggtatgaga taatcaggcc taatcatgtt gtgattctct tttcttagtg      3660
gagtggaatt ttctatcccc acaagaagga ttatatctta tagacttgtc ttgttcagat      3720
tctgtattta cccattttat tgaaacatat actaagttcc atgtattttt gttacaaatc      3780
ttctgaaaaa aaacaaaaca atgtgaaaca ttaaaattaa aaggcattaa taataaaaaa      3840
aaaaaaaaaa aaaaaaaa                                                    3859
```

<210> SEQ ID NO 19
<211> LENGTH: 3813
<212> TYPE: DNA
<213> ORGANISM: Homo sapiens

<400> SEQUENCE: 19

```
ggcagttagc ccgcccgctc ggcgcagggc gtggcttctc gtagccatta ggaaacagca        60 acccttcac ctcagttttc ttcactccgg catttgcagc agagcgaaag gtggtcgagt        120
cctgaaggag ggcctgatgt cttcatcatt ctcaaattct tgtaagctct gcgtcgggtg       180
aaaccagaca aagccgcgag cccagggatg ggagcacgcg gggacggcc tgccggcggg        240 gacgacagca ttgcgcctgg gtgcagcagt gtgcgtctcg gggaagggaa gatattttaa       300
ggcgtgtctg agcagacggg gaggcttttc caaacccagg cagcttcgtg gcgtgtgcgg       360
tttcgacccg gtcacacaaa gcttcagcat gtcatgtggc ttatcaggag ggcagacttc       420
```

```
aaaagctact aaaaatgaac ggccctgaag atcttcccaa gtcctatgac tatgacctta    480
tcatcattgg aggtggctca ggaggtctgg cagctgctaa ggaggcagcc caatatggca    540
agaaggtgat ggtcctggac tttgtcactc ccaccctct tggaactaga tggggtctcg    600
gaggaacatg tgtgaatgtg ggttgcatac ctaaaaaact gatgcatcaa gcagctttgt    660
taggacaagc cctgcaagac tctcgaaatt atggatggaa agtcgaggag acagttaagc    720
atgattggga cagaatgata aagctgtac agaatcacat tggctctttg aattggggct    780
accgagtagc tctgcgggag aaaaaagtcg tctatgagaa tgcttatggg caatttattg    840
gtcctcacag gattaaggca acaaataata aaggcaaaga aaaaatttat tcagcagaga    900
gatttctcat tgccactggt gaaagaccac gttacttggg catccctggt gacaaagaat    960
actgcatcag cagtgatgat cttttctcct tgccttactg cccgggtaag accctggttg   1020
ttggagcatc ctatgtcgct ttggagtgcg ctggatttct tgctggtatt ggtttagacg   1080
tcactgttat ggttaggtcc attcttctta gaggatttga ccaggacatg gccaacaaaa   1140
ttggtgaaca catggaagaa catggcatca agtttataag acagttcgta ccaattaaag   1200
ttgaacaaat tgaagcaggg acaccaggcc gactcagagt agtagctcag tccaccaata   1260
gtgaggaaat cattgaagga gaatataata cggtgatgct ggcaatagga agagatgctt   1320
gcacaagaaa aattggctta gaaaccgtag gggtgaagat aaatgaaaag actgaaaaaa   1380
tacctgtcac agatgaagaa cagaccaatg tgccttacat ctatgccatt ggcgatatat   1440
tggaggataa ggtggagctc accccagttg caatccaggc aggaagattg ctggctcaga   1500
ggctctatgc aggttccact gtcaagtgtg actatgaaaa tgttccaacc actgtattta   1560
ctcctttgga atatggtgct tgtggccttt ctgaggagaa agctgtggag aagtttgggg   1620
aagaaaatat tgaggtttac catagttact tttggccatt ggaatggacg attccgtcaa   1680
gagataacaa caaatgttat gcaaaaataa tctgtaatac taaagacaat gaacgtgttg   1740
tgggctttca cgtactgggt ccaaatgctg agaagttac acaaggcttt gcagctgcgc   1800
tcaaatgtgg actgaccaaa aagcagctgg acagcacaat tggaatccac cctgtctgtg   1860
cagaggtatt cacaacattg tctgtgacca gcgctctgg ggcaagcatc ctccaggctg   1920
gctgctgagt taagcccca gtgtggatgc tgttgccaag actgcaaacc actggctcgt   1980
ttccgtgccc aaatccaagg cgaagttttc tagagggttc ttgggctctt ggcacctgcg   2040
tgtcctgtgc ttaccaccgc ccaaggcccc cttggatctc ttggatagga ttggtgaat   2100 agaaggcagg cagcatcaca ctggggtcac tgacagactt gaagctgaca tttggcaggg   2160
catcgaaggg atgcatccat gaagtcacca gtctcaagcc catgtggtag gcggtgatgg   2220
aacaactgtc aaatcagttt tagcatgacc tttccttgtg gattttctta ttctcgttgt   2280
caagttttct agggttgaat ttttttcttt tttctccatg gtgttaatga tattagagat   2340
gaaaaacgtt agcagttgat ttttgtccaa aagcaagtca tggctagagt atccatgcaa   2400
ggtgtcttgt tgcatggaag ggatagtttg gctcccttgg aggctatgta ggcttgtccc   2460
gggaaagaga actgtcctgc agctgaaatg gactgttctt tactgacctg ctcagcagtt   2520
tcttctctca tatattccca aaacaagtac atctgcgatc aactctagcc aaatttgccc   2580
ctgtgtgcta catgatggat gattattatt ttaaggtctg tttaggaagg gaaatggcta   2640
cttggccagc cattgcctgg catttggtag tatagtatga ttctcaccat tatttgtcat   2700
ggaggcagac atacaccaga aatggggag aaacagtaca tatctttctg tctttagttt   2760
attgtgtgct ggtctaagca agctgagatc atttgcaatg gaaaacacgt aacttgttta   2820
```

| | |
|---|---:|
| aaagttttc tggtagcttt agctttatgc taaaaaaaat aatgacattg ggtatctatt | 2880 |
| tctttctaag actacattag taggaaaata agtcttttca tgcttatgat ttagctgttt | 2940 |
| tgtggtaatt gcttttaaa ggaagttatt aatatcataa gttattatta atattttgaa | 3000 |
| cacaggtgga tgtgaaggat tttcatttaa aaaccaagtg gttttgactt tttctgttga | 3060 |
| atgaacaact gtgccttgtg gaattttgc agaagtgttt atgctttgtt agcatttcaa | 3120 |
| cttgcattat tataaagagg tattaatgcc tcagttatgt gtttgtcaat gtactggctg | 3180 |
| aggattctat ctcagctgtc ttttctaact gtgtaggttg agttttgaac acgtgcttgt | 3240 |
| ggacatcagg cctcctgcca gcagttcttg aagcttcttt ttcattcctg ctactctacc | 3300 |
| tgtatttctc agttgcagca ctgagtggtc aaaatacatt tctgggccac ctcaggaac | 3360 |
| ccatgcatct gcctggcatt taggcagcag agccctgac cgtccccac agggctctgc | 3420 |
| ctcacgtcct catctcattt ggctgtgtaa agaaatggga aaagggaaaa ggagagagca | 3480 |
| attgaggcag ttgaccatat tcagtttat ttatttattt ttaatttgtt ttttctcca | 3540 |
| agtccaccag tctctgaaat tagaacagta ggcggtatga dataatcagg cctaatcatg | 3600 |
| ttgtgattct cttttcttag tggagtggaa tgttctatcc ccacaagaag gattatatct | 3660 |
| tatagacttg tcttgttcag attctgtatt tacccatttt attgaaacat atactaagtt | 3720 |
| ccatgtattt ttgttacaaa tcttctgaaa aaaaacaaaa caatgtgaaa cattaaaatt | 3780 |
| aaaaggcatt aataataaaa aaaaaaaaaa aaa | 3813 |

```
<210> SEQ ID NO 20
<211> LENGTH: 3694
<212> TYPE: DNA
<213> ORGANISM: Homo sapiens

<400> SEQUENCE: 20
```

| | |
|---|---:|
| ggcagttagc ccgcccgctc ggcgcagggc gtggcttctc gtagccatta ggaaacagca | 60 |
| acccttcac ctcagttttc ttcactccgg catttgcagc agagcgaaag gtggtcgagt | 120 |
| cctgaaggag ggcctgatgt cttcatcatt ctcaaattct taggacggtc gggccctgga | 180 |
| aggaacgctc tcggaattgg ccgcggaaac cgatctgccc gttgtgtttg tgaaacagag | 240 |
| aaagataggc ggccatggtc caaccttgaa ggcttatcag gagggcagac ttcaaaagct | 300 |
| actaaaaatg aacggccctg aagatcttcc caagtcctat gactatgacc ttatcatcat | 360 |
| tgaggtggc tcaggaggtc tggcagctgc taaggaggca gcccaatatg gcaagaaggt | 420 |
| gatggtcctg gactttgtca ctcccacccc tcttggaact agatgggtc tcggaggaac | 480 |
| atgtgtgaat gtgggttgca tacctaaaaa actgatgcat caagcagctt tgttaggaca | 540 |
| agccctgcaa gactctcgaa attatggatg gaaagtcgag gagacagtta agcatgattg | 600 |
| ggacagaatg atagaagctg tacagaatca cattggctct ttgaattggg gctaccgagt | 660 |
| agctctgcgg gagaaaaaag tcgtctatga gaatgcttat gggcaattta ttggtcctca | 720 |
| caggattaag gcaacaaata ataaaggcaa agaaaaaatt tattcagcag agagatttct | 780 |
| cattgccact ggtgaaagac cacgttactt gggcatccct ggtgacaaag aatactgcat | 840 |
| cagcagtgat gatctttct ccttgcctta ctgcccgggt aagaccctgg ttgttggagc | 900 |
| atcctatgtc gctttggagt gcgctggatt tcttgctggt attggtttag acgtcactgt | 960 |
| tatggttagg tccattcttc ttagaggatt tgaccaggac atggccaaca aaattggtga | 1020 |
| acacatggaa gaacatggca tcaagtttat aagcacagttc gtaccaatta aagttgaaca | 1080 |
| aattgaagca gggacaccag gccgactcag agtagtagct cagtccacca atagtgagga | 1140 |

```
aatcattgaa ggagaatata atacggtgat gctggcaata ggaagagatg cttgcacaag    1200
aaaaattggc ttagaaaccg tagggtgaa gataaatgaa aagactggaa aaatacctgt    1260
```
*(correcting)*
```
aatcattgaa ggagaatata atacggtgat gctggcaata ggaagagatg cttgcacaag    1200
aaaaattggc ttagaaaccg tagggggtgaa gataaatgaa aagactggaa aaatacctgt    1260
cacagatgaa gaacagacca atgtgcctta catctatgcc attggcgata tattggagga    1320
taaggtggag ctcaccccag ttgcaatcca ggcaggaaga ttgctggctc agaggctcta    1380
tgcaggttcc actgtcaagt gtgactatga aaatgttcca accactgtat ttactccttt    1440
ggaatatggt gcttgtggcc tttctgagga gaaagctgtg gagaagtttg gggaagaaaa    1500
tattgaggtt taccatagtt acttttggcc attggaatgg acgattccgt caagagataa    1560
caacaaatgt tatgcaaaaa taatctgtaa tactaaagac aatgaacgtg ttgtgggctt    1620
tcacgtactg ggtccaaatg ctggagaagt tacacaaggc tttgcagctg cgctcaaatg    1680
tggactgacc aaaaagcagc tggacagcac aattggaatc caccctgtct gtgcagaggt    1740
attcacaaca ttgtctgtga ccaagcgctc tggggcaagc atcctccagg ctggctgctg    1800
aggttaagcc ccagtgtgga tgctgttgcc aagactgcaa accactggct cgtttccgtg    1860
cccaaatcca aggcgaagtt ttctagaggg ttcttgggct cttggcacct gcgtgtcctg    1920
tgcttaccac cgcccaaggc ccccttggat ctcttggata ggagttggtg aatagaaggc    1980
aggcagcatc acactggggt cactgacaga cttgaagctg acatttggca gggcatcgaa    2040
gggatgcatc catgaagtca ccagtctcaa gcccatgtgg taggcggtga tggaacaact    2100
gtcaaatcag ttttagcatg acctttcctt gtggattttc ttattctcgt tgtcaagttt    2160
tctagggttg aattttttc tttttctcc atggtgttaa tgatattaga gatgaaaaac    2220
gttagcagtt gattttgtc caaaagcaag tcatggctag agtatccatg caaggtgtct    2280
tgttgcatgg aagggatagt ttggctccct tggaggctat gtaggcttgt cccgggaaag    2340
agaactgtcc tgcagctgaa atggactgtt ctttactgac ctgctcagca gtttcttctc    2400
tcatatattc ccaaaacaag tacatctgcg atcaactcta gccaaatttg ccctgtgtg    2460 ctacatgatg gatgattatt attttaaggt ctgtttagga agggaaatgg ctacttggcc    2520
agccattgcc tggcatttgg tagtatagta tgattctcac cattatttgt catggaggca    2580
gacatacacc agaaatgggg gagaaacagt acatatcttt ctgtctttag tttattgtgt    2640
gctggtctaa gcaagctgag atcatttgca atggaaaaca cgtaacttgt ttaaaagttt    2700
ttctggtagc tttagcttta tgctaaaaaa aataatgaca ttgggtatct atttctttct    2760
aagactacat tagtaggaaa ataagtcttt tcatgcttat gatttagctg ttttgtggta    2820
attgcttttt aaaggaagtt attaatatca taagttatta ttaatatttt gaacacaggt    2880
ggatgtgaag gattttcatt taaaaaccaa gtggttttga cttttctgt tgaatgaaca    2940 actgtgcctt gtggaatttt tgcagaagtg tttatgcttt gttagcattt caacttgcat    3000
tattataaag aggtattaat gcctcagtta tgtgtttgtc aatgtactgg ctgaggattc    3060
tatctcagct gtcttttcta actgtgtagg ttgagttttg aacacgtgct tgtggacatc    3120
aggcctcctg ccagcagttc ttgaagcttc ttttcattc ctgctactct acctgtattt    3180
ctcagttgca gcactgagtg gtcaaaatac atttctgggc cacctcaggg aacccatgca    3240
tctgcctggc atttaggcag cagagcccct gaccgtcccc cacagggctc tgcctcacgt    3300
cctcatctca tttggctgtg taagaaatg ggaaaaggga aaggagaga gcaattgagg    3360 cagttgacca tattcagttt tatttattta tttttaattt gttttttct ccaagtccac    3420 cagtctctga aattagaaca gtaggcggta tgagataatc aggcctaatc atgttgtgat    3480 tctctttct tagtggagtg gaatgttcta tccccacaag aaggattata tcttatagac    3540
```

```
ttgtcttgtt cagattctgt atttacccat tttattgaaa catatactaa gttccatgta    3600
tttttgttac aaatcttctg aaaaaaaaca aaacaatgtg aaacattaaa attaaaaggc    3660
attaataata aaaaaaaaaa aaaaaaaaaa aaaa                                3694

<210> SEQ ID NO 21
<211> LENGTH: 3576
<212> TYPE: DNA
<213> ORGANISM: Homo sapiens

<400> SEQUENCE: 21
ggcagttagc ccgcccgctc ggcgcagggc gtggcttctc gtagccatta ggaaacagca      60 acccttttcac ctcagttttc ttcactccgg catttgcagc agagcgaaag gtggtcgagt    120
cctgaaggag ggcctgatgt cttcatcatt ctcaaattct tgcttatcag gagggcagac    180
ttcaaaagct actaaaaatg aacggccctg aagatcttcc caagtcctat gactatgacc    240
ttatcatcat tggaggtggc tcaggaggtc tggcagctgc taaggaggca gcccaatatg    300
gcaagaaggt gatggtcctg gactttgtca ctcccacccc tcttggaact agatggggtc    360
tcggaggaac atgtgtgaat gtgggttgca tacctaaaaa actgatgcat caagcagctt    420
tgttaggaca agccctgcaa gactctcgaa attatggatg gaaagtcgag gagacagtta    480
agcatgattg ggacagaatg atagaagctg tacagaatca cattggctct ttgaattggg    540
gctaccgagt agctctgcgg gagaaaaaag tcgtctatga aatgcttat gggcaattta    600 ttggtcctca caggattaag gcaacaaata taaaggcaa agaaaaatt tattcagcag    660 agagatttct cattgccact ggtgaaagac cacgttactt gggcatccct ggtgacaaag    720
aatactgcat cagcagtgat gatcttttct ccttgcctta ctgcccgggt aagaccctgg    780
ttgttggagc atcctatgtc gctttggagt gcgctggatt tcttgctggt attggtttag    840
acgtcactgt tatggttagg tccattcttc ttagaggatt tgaccaggac atggccaaca    900
aaattggtga acacatggaa gaacatggca tcaagtttat aagacagttc gtaccaatta    960
aagttgaaca aattgaagca gggacaccag gccgactcag agtagtagct cagtccacca   1020
atagtgagga aatcattgaa ggagaatata atacggtgat gctggcaata ggaagagatg   1080
cttgcacaag aaaaattggc ttagaaaccg taggggtgaa gataaatgaa aagactggaa   1140
aaatacctgt cacagatgaa gaacagacca atgtgcctta catctatgcc attggcgata   1200
tattggagga taaggtggag ctcaccccag ttgcaatcca ggcaggaaga ttgctggctc   1260
agaggctcta tgcaggttcc actgtcaagt gtgactatga aaatgttcca accactgtat   1320
ttactccttt ggaatatggt gcttgtggcc tttctgagga aaagctgtg gagaagtttg   1380 gggaagaaaa tattgaggtt taccatagtt acttttggcc attggaatgg acgattccgt   1440
caagagataa caacaaatgt tatgcaaaaa taatctgtaa tactaaagac aatgaacgtg   1500
ttgtgggctt tcacgtactg ggtccaaatg ctggagaagt tacacaaggc tttgcagctg   1560
cgctcaaatg tggactgacc aaaaagcagc tggacagcac aattggaatc caccctgtct   1620
gtgcagaggt attcacaaca ttgtctgtga ccaagcgctc tggggcaagc atcctccagg   1680
ctggctgctg aggttaagcc ccagtgtgga tgctgttgcc aagactgcaa accactggct   1740
cgtttccgtg cccaaatcca aggcgaagtt ttctagaggg ttcttgggct cttggcacct   1800
gcgtgtcctg tgcttaccac cgcccaaggc ccccttggat ctcttggata ggagttggtg   1860
aatagaaggc aggcagcatc acactgggt cactgacaga cttgaagctg acatttggca   1920
gggcatcgaa gggatgcatc catgaagtca ccagtctcaa gcccatgtgg taggcggtga   1980
```

-continued

```
tggaacaact gtcaaatcag ttttagcatg acctttcctt gtggattttc ttattctcgt    2040
tgtcaagttt tctagggttg aatttttttc ttttttctcc atggtgttaa tgatattaga    2100
gatgaaaaac gttagcagtt gattttttgtc caaaagcaag tcatggctag agtatccatg   2160
caaggtgtct tgttgcatgg aagggatagt ttggctccct tggaggctat gtaggcttgt    2220
cccgggaaag agaactgtcc tgcagctgaa atggactgtt ctttactgac ctgctcagca    2280
gtttcttctc tcatatattc ccaaaacaag tacatctgcg atcaactcta gccaaatttg    2340
cccctgtgtg ctacatgatg gatgattatt attttaaggt ctgtttagga agggaaatgg    2400
ctacttggcc agccattgcc tggcatttgg tagtatagta tgattctcac cattatttgt    2460
catggaggca gacatacacc agaaatgggg gagaaacagt acatatcttt ctgtctttag    2520
tttattgtgt gctggtctaa gcaagctgag atcatttgca atggaaaaca cgtaacttgt    2580
ttaaagtttt ttctggtagc tttagcttta tgctaaaaaa aataatgaca ttgggtatct    2640
atttcttcct aagactacat tagtaggaaa ataagtcttt tcatgcttat gatttagctg    2700
ttttgtggta attgcttttt aaaggaagtt attaatatca taagttatta ttaatatttt    2760
gaacacaggt ggatgtgaag gattttcatt taaaaaccaa gtggttttga cttttctgt    2820 tgaatgaaca actgtgcctt gtggaattttt tgcagaagtg tttatgcttt gttagcattt    2880
caacttgcat tattataaag aggtattaat gcctcagtta tgtgtttgtc aatgtactgg    2940
ctgaggattc tatctcagct gtcttttcta actgtgtagg ttgagttttg aacacgtgct    3000
tgtggacatc aggcctcctg ccagcagttc ttgaagcttc tttttcattc ctgctactct    3060 acctgtatttt ctcagttgca gcactgagtg gtcaaaatac atttctgggc cacctcaggg   3120
aacccatgca tctgcctggc atttaggcag cagagcccct gaccgtcccc cacagggctc    3180
tgcctcacgt cctcatctca tttggctgtg taaagaaatg ggaaagggaa aaggagaga    3240 gcaattgagg cagttgacca tattcagttt tatttattta ttttttaattt gttttttctt   3300 ccaagtccac cagtctctga aattagaaca gtaggcggta tgagataatc aggcctaatc    3360
atgttgtgat tctcttttct tagtggagtg gaatgttcta tccccacaag aaggattata    3420
tcttatagac ttgtcttgtt cagattctgt atttacccat tttattgaaa catatactaa    3480
gttccatgta ttttttgttac aaatcttctg aaaaaaaaca aaacaatgtg aaacattaaa   3540
attaaaaggc attaataata aaaaaaaaaa aaaaaa                              3576
```

<210> SEQ ID NO 22
<211> LENGTH: 5891
<212> TYPE: DNA
<213> ORGANISM: Homo sapiens

<400> SEQUENCE: 22

```
ccaggagagc ggcgtggacg cgtgcgggcc tagaggccca cgtgatccgc agggcggccg     60
aggcaggaag ctgtgagtgc gcggttgcgg ggtcgcattg tggctacggc tttgcgtccc    120
cggcgggcag ccccaggctg gtccccgcct ccgctctccc caccggcggg gaaagcagct    180
ggtgtgggag gaaaggctcc atccccgcc ccctctctcc cgctgttggc tggcaggatc     240
ttttggcagt cctgtggcct cgctccccgc ccggatcctc ctgaccctga gattcgcggg    300
tctcacgtcc cgtgcacgcc ttgcttcggc ctcagttaag cctttgtgga ctccaggtcc    360
ctggtgagat tagaaacgtt tgcaaacatg tcccggatcg aaaagatgag cattctgggc    420
gtgcggagtt ttggaataga ggacaaagat aagcaaatta tcactttctt cagccccctt    480 acaatttttgg ttggacccaa tggggcggga aagacgacca tcattgaatg tctaaaatat    540
```

```
atttgtactg gagatttccc tcctggaacc aaaggaaata catttgtaca cgatcccaag    600
gttgctcaag aaacagatgt gagagcccag attcgtctgc aatttcgtga tgtcaatgga    660
gaacttatag ctgtgcaaag atctatggtg tgtactcaga aaagcaaaaa gacagaattt    720
aaaactctgg aaggagtcat tactagaaca aagcatggtg aaaaggtcag tctgagctct    780
aagtgtgcag aaattgaccg agaaatgatc agttctcttg gggtttccaa ggctgtgcta    840
aataatgtca ttttctgtca tcaagaagat tctaattggc ctttaagtga aggaaaggct    900
ttgaagcaaa agtttgatga gattttttca gcaacaagat acattaaagc cttagaaaca    960
cttcggcagg tacgtcagac acaaggtcag aaagtaaaag aatatcaaat ggaactaaaa   1020
tatctgaagc aatataagga aaaagcttgt gagattcgtg atcagattac aagtaaggaa   1080
gcccagttaa catcttcaaa ggaaattgtc aaatcctatg agaatgaact tgatccattg   1140
aagaatcgtc taaagaaat tgaacataat ctctctaaaa taatgaaact tgacaatgaa   1200
attaaagcct tggatagccg aaagaagcaa atggagaaag ataatagtga actggaagag   1260
aaaatggaaa aggttttca agggactgat gagcaactaa atgacttata tcacaatcac   1320
cagagaacag taagggagaa agaaaggaaa ttggtagact gtcatcgtga actggaaaaa   1380
ctaaataaag aatctaggct tctcaatcag gaaaaatcag aactgcttgt tgaacagggt   1440
cgtctacagc tgcaagcaga tcgccatcaa gaacatatcc gagctagaga ttcattaatt   1500
cagtctttgg caacacagct agaattggat ggctttgagc gtggaccatt cagtgaaaga   1560
cagattaaaa atttcacaa acttgtgaga gagagacaag aaggggaagc aaaaactgcc   1620
aaccaactga tgaatgactt tgcagaaaaa gagactctga acaaaaaca gatagatgag   1680 ataagagata agaaaactgg actgggaaga ataattgagt taaaatcaga atcctaagt   1740 aagaagcaga atgagctgaa aaatgtgaag tatgaattac agcagttgga aggatcttca   1800
gacaggattc ttgaactgga ccaggagctc ataaaagctg aacgtgagtt aagcaaggct   1860
gagaaaaaca gcaatgtaga aaccttaaaa atggaagtaa taagtctcca aaatgaaaaa   1920
gcagacttag acaggaccct gcgtaaactt gaccaggaga tggagcagtt aaaccatcat   1980
acaacaacac gtacccaaat ggagatgctg accaaagaca aagctgacaa agatgaacaa   2040
atcagaaaaa taaatctag gcacagtgat gaattaacct cactgttggg atattttccc   2100 aacaaaaac agcttgaaga ctggctacat agtaaatcaa aagaaattaa tcagaccagg   2160
gacagacttg ccaaattgaa caaggaacta gcttcatctg agcagaataa aaatcatata   2220
aataatgaac taaaagaaa ggaagagcag ttgtccagtt acgaagacaa gctgtttgat   2280
gtttgtggta gccaggattt tgaaagtgat ttagacaggc ttaaagagga aattgaaaaa   2340
tcatcaaaac agcgagccat gctggctgga gccacagcag tttactccca gttcattact   2400
cagctaacag acgaaaacca gtcatgttgc ccgtttgtc agagagtttt tcagacagag   2460
gctgagttac aagaagtcat cagtgatttg cagtctaaac tgcgacttgc tccagataaa   2520
ctcaagtcaa cagaatcaga gctaaaaaaa aaggaaaagc ggcgtgatga atgctggga   2580 cttgtgccca tgaggcaaag cataattgat ttgaaggaga aggaaatacc agaattaaga   2640
aacaaactgc agaatgtcaa tagagacata cagcgcctaa agaacgacat agaagaacaa   2700
gaaacactct tgggtacaat aatgcctgaa gaagaaagtg ccaaagtatg cctgacagat   2760
gttacaatta tggagaggtt ccagatggaa cttaaagatg ttgaaagaaa aattgcacaa   2820
caagcagcta agctacaagg aatagactta gatcgaactg tccaacaagt caaccaggag   2880
aaacaagaga acagcacaa gttagacaca gtttctagta agattgaatt gaatcgtaag   2940
```

```
cttatacagg accagcagga acagattcaa catctaaaaa gtacaacaaa tgagctaaaa    3000
tctgagaaac ttcagatatc cactaatttg caacgtcgtc agcaactgga ggagcagact    3060
gtggaattat ccactgaagt tcagtctttg tacagagaga taaggatgc taaagagcag     3120 gtaagccctt tggaaacaac attggaaaag ttccagcaag aaaaagaaga attaatcaac    3180
aaaaaaaata caagcaacaa atagcacag gataaactga atgatattaa agagaaggtt    3240
aaaaatattc atggctatat gaaagacatt gagaattata ttcaagatgg gaaagacgac    3300
tataagaagc aaaaagaaac tgaacttaat aaagtaatag ctcaactaag tgaatgcgag    3360
aaacacaaag aaaagataaa tgaagatatg agactcatga gacaagatat tgatacacag    3420
aagatacaag aaaggtggct acaagataac cttactttaa gaaaaagaaa tgaggaacta    3480
aaagaagttg aagaagaaag aaaacaacat ttgaaggaaa tgggtcaaat gcaggttttg    3540
caaatgaaaa gtgaacatca gaagttggaa gagaacatag acaatataaa aagaaatcat    3600
aatttggcat tagggcgaca gaaaggttat gaagaagaaa ttattcattt taagaaagaa    3660
cttcgagaac cacaatttcg ggatgctgag gaaaagtata gagaaatgat gattgttatg    3720
aggacaacag aacttgtgaa caaggatctg gatatttatt ataagactct tgaccaagca    3780
ataatgaaat ttcacagtat gaaaatggaa gaaatcaata aaattatacg tgacctgtgg    3840
cgaagtacct atcgtggaca agatattgaa tacatagaaa tacggtctga tgccgatgaa    3900
aatgtatcag cttctgataa aaggcggaat tataactacc gagtggtgat gctgaaggga    3960
gacacagcct tggatatgcg aggacgatgc agtgctggac aaaaggtatt agcctcactc    4020
atcattcgcc tggccctggc tgaaacgttc tgcctcaact gtggcatcat tgccttggat    4080
gagccaacaa caaatcttga ccgagaaaac attgaatctc ttgcacatgc tctggttgag    4140
ataataaaaa gtcgctcaca gcagcgtaac ttccagcttc tggtaatcac tcatgatgaa    4200
gattttgtgg agcttttagg acgttctgaa tatgtggaga aattctacag gattaaaaag    4260
aacatcgatc agtgctcaga gattgtgaaa tgcagtgtta gctccctggg attcaatgtt    4320
cattaaaaat atccaagatt taaatgccat agaaatgtag gtcctcagaa agtgtataat    4380
aagaaactta tttctcatat caacttagtc aataagaaaa tatattcttt caaaggaaca    4440
ttgtgtctag gattttggat gttgagaggt tctaaaatca tgaaacttgt ttcactgaaa    4500
attggacaga ttgcctgttt ctgatttgct gctcttcatc ccattccagg cagcctctgt    4560
caggccttca gggttcagca gtacagccga gactcgactc tgtgcctccc tccccagtgc    4620
aaatgcatgc ttcttctcaa agcactgttg agaaggagat aattactgcc ttgaaaattt    4680
atggttttgg tatttttta aatcatagtt aaatgttacc tctgaattta cttccttgca    4740
tgtggtttga aaaactgagt attaatatct gaggatgacc agaaatggtg agatgtatgt    4800
ttggctctgc ttttaacttt ataaatccag tgacctctct ctctgggact tggtttcccc    4860
aactaaaatt tgaagtagtt gaatggggtc tcaaagtttg acaggaacct taagtaatca    4920
tctaagtcag tacccaccac cttcttctcc tacatatccc ttccagatgg tcatccagac    4980
tcagagctct ctctacagag aggaaattct ccactgtgca cacccacctt tggaaagctc    5040
tgaccacttg aggcctgatc tgcccatcgt gaagaagcct gtaacactcc tctgcgtcta    5100
tcctgtgtag catactggct tcaccatcaa tcctgattcc tctctaagtg ggcattgcca    5160
tgtggaaggc aagccaggct cactcacaga gtcaaggcct gctccctgta gggtccaacc    5220
agacctggaa gaacaggcct ctccatttgc tcttcagatg ccacttctaa gaaaagccta    5280
atcacagttt ttcctggaat tgccagctga catcttgaat ccttccattc cacacagaat    5340
```

```
gcaaccaagt cacacgcttt tgaattatgc tttgtagagt tttgtcattc agagtcagcc    5400
aggaccatac cgggtcttga ttcagtcaca tggcatggtt ttgtgccatc tgtagctata    5460
atgagcatgt ttgcctagac agcttttctc aactgggtcc agaagagaat taagccctaa    5520
ggtcctaagg catctatctg tgctaggtta aatggttggc ccccaaagat agacaggtcc    5580
tgatttctag aacccgtgac tgttacttta tacagcaaag gaaactttgc agatgtgatt    5640
aaagctaagg accttaagac agagtatcct gggggtggtg gtggggtggg gggggtcct     5700 aaatgtaatc acgagtaaga ttaagagcaa atcaattcta gtcatatatt aaacatccac    5760
aataaccaag atattttat cccaagaatg caagatttca gaaaatgaaa aatctgttga     5820
taaatccatc actataataa aaccgaaggt gaaaaaaatt ctgaaaaaaa aaaaaaaaa     5880 aaaaaaaaaa a                                                         5891

<210> SEQ ID NO 23
<211> LENGTH: 5826
<212> TYPE: DNA
<213> ORGANISM: Homo sapiens

<400> SEQUENCE: 23
ccaggagagc ggcgtggacg cgtgcgggcc tagaggccca cgtgatccgc agggcggccg     60
aggcaggaag ctgtgagtgc gcggttgcgg ggtcgcattg tggctacggc tttgcgtccc    120
cggcgggcag ccccaggctg gtccccgcct ccgctctccc caccggcggg gaaagcagct    180
ggtgtgggag gaaaggctcc atccccgcc ccctctctcc cgctgttggc tggcaggatc     240
ttttggcagt cctgtggcct cgctccccgc ccggatcctc ctgaccctga gattcgcggg    300
tctcacgtcc cgtgcacgcc ttgcttcggc ctcagttaag cctttgtgga ctccaggtcc    360
ctggtgagat tagaaacgtt tgcaaacatg tcccggatcg aaaagatgag cattctgggc    420
gtgcggagtt ttggaataga ggacaaagat aagcaaatta tcactttctt cagcccccct    480
acaattttgg ttggacccaa tggggcggga agacgaccca tcattgaatg tctaaaatat    540
atttgtactg gagatttccc tcctggaacc aaaggaaata catttgtaca cgatcccaag    600
gttgctcaag aaacagatgt gagagcccag attcgtctgc aatttcgtga tgtcaatgga    660
gaacttatag ctgtgcaaag atctatggca tggtgaaaag gtcagtctga gctctaagtg    720
tgcagaaatt gaccgagaaa tgatcagttc tcttgggggtt tccaaggctg tgctaaataa    780
tgtcattttc tgtcatcaag aagattctaa ttggcctttta agtgaaggaa aggctttgaa    840
gcaaaagttt gatgagattt tttcagcaac aagatacatt aaagccttag aaacacttcg    900
gcaggtacgt cagacacaag gtcagaaagt aaaagaatat caaatggaac taaaatatct    960
gaagcaatat aaggaaaaag cttgtgagat tcgtgatcag attacaagta aggaagccca    1020
gttaacatct tcaaaggaaa ttgtcaaatc ctatgagaat gaacttgatc cattgaagaa    1080
tcgtctaaaa gaaattgaac ataatctctc taaaataatg aaacttgaca atgaaattaa    1140
agccttggat agccgaaaga agcaaatgga gaaagataat agtgaactgg aagagaaaat    1200
ggaaaaggtt tttcaaggga ctgatgagca actaaatgac ttatatcaca atcaccagag    1260
aacagtaagg gagaaagaaa ggaaattggt agactgtcat cgtgaactgg aaaaactaaa    1320 taagaatct aggcttctca atcaggaaaa atcagaactg cttgttgaac agggtcgtct    1380
acagctgcaa gcagatcgcc atcaagaaca tatccgagct agagattcat taattcagtc    1440
tttggcaaca cagctagaat tggatggctt tgagcgtgga ccattcagtg aaagacagat    1500
taaaaatttt cacaaacttg tgagagagag acaagaaggg gaagcaaaaa ctgccaacca    1560
```

```
actgatgaat gactttgcag aaaaagagac tctgaaacaa aaacagatag atgagataag    1620
agataagaaa actggactgg gaagaataat tgagttaaaa tcagaaatcc taagtaagaa    1680
gcagaatgag ctgaaaaatg tgaagtatga attacagcag ttggaaggat cttcagacag    1740
gattcttgaa ctggaccagg agctcataaa agctgaacgt gagttaagca aggctgagaa    1800
aaacagcaat gtagaaacct taaaaatgga agtaataagt ctccaaaatg aaaaagcaga    1860
cttagacagg accctgcgta aacttgacca ggagatggag cagttaaacc atcatacaac    1920
aacacgtacc caaatggaga tgctgaccaa agacaaagct gacaaagatg aacaaatcag    1980
aaaaataaaa tctaggcaca gtgatgaatt aacctcactg ttgggatatt ttcccaacaa    2040
aaaacagctt gaagactggc tacatagtaa atcaaaagaa attaatcaga ccagggacag    2100
acttgccaaa ttgaacaagg aactagcttc atctgagcag aataaaaatc atataaataa    2160
tgaactaaaa agaaaggaag agcagttgtc cagttacgaa gacaagctgt ttgatgtttg    2220
tggtagccag gattttgaaa gtgatttaga caggcttaaa gaggaaattg aaaaatcatc    2280
aaaacagcga gccatgctgg ctggagccac agcagtttac tcccagttca ttactcagct    2340
aacagacgaa aaccagtcat gttgccccgt ttgtcagaga gttttttcaga cagaggctga    2400 gttacaagaa gtcatcagtg atttgcagtc taaactgcga cttgctccag ataaactcaa    2460
gtcaacagaa tcagagctaa aaaaaaagga aaagcggcgt gatgaaatgc tgggacttgt    2520
gcccatgagg caaagcataa ttgatttgaa ggagaaggaa ataccagaat taagaaacaa    2580
actgcagaat gtcaatagag acatacgcg cctaaagaac gacatagaag aacagaaac     2640 actcttgggt acaataatgc ctgaagaaga aagtgccaaa gtatgcctga cagatgttac    2700
aattatggag aggttccaga tggaacttaa agatgttgaa agaaaaattg cacaacaagc    2760
agctaagcta caaggaatag acttagatcg aactgtccaa caagtcaacc aggagaaaca    2820
agagaaacag cacaagttag acacagtttc tagtaagatt gaattgaatc gtaagcttat    2880
acaggaccag caggaacaga ttcaacatct aaaaagtaca acaaatgagc taaaatctga    2940
gaaacttcag atatccacta atttgcaacg tcgtcagcaa ctggaggagc agactgtgga    3000
attatccact gaagttcagt cttttgtacag agagataaag gatgctaaag agcaggtaag    3060
ccctttggaa acaacattgg aaaagttcca gcaagaaaaa gaagaattaa tcaacaaaaa    3120
aaatacaagc aacaaaatag cacaggataa actgaatgat attaaagaga aggttaaaaa    3180
tattcatggc tatatgaaag acattgaaaa ttatattcaa gatgggaaag acgactataa    3240
gaagcaaaaa gaaactgaac ttaataaagt aatagctcaa ctaagtgaat gcgagaaaca    3300
caaagaaaag ataaatgaag atatgagact catgagacaa gatattgata cacagaagat    3360
acaagaaagg tggctacaag ataaccttac tttaagaaaa agaaatgagg aactaaaaga    3420
agttgaagaa gaaagaaaac aacatttgaa ggaaatgggt caaatgcagg ttttgcaaat    3480
gaaaagtgaa catcagaagt tggaagagaa catagacaat ataaaagaa atcataattt     3540 ggcattaggg cgacagaaag gttatgaaga agaaattatt cattttaaga aagaacttcg    3600
agaaccacaa tttcgggatg ctgaggaaaa gtatagagaa atgatgattg ttatgaggac    3660
aacagaactt gtgaacaagg atctggatat ttattataag actcttgacc aagcaataat    3720
gaaatttcac agtatgaaaa tggaagaaat caataaaatt atacgtgacc tgtggcgaag    3780
tacctatcgt ggacaagata ttgaatacat agaaatacgg tctgatgccg atgaaaatgt    3840
atcagcttct gataaaaggc ggaattataa ctaccgagtg gtgatgctga agggagacac    3900
agccttggat atgcgaggac gatgcagtgc tggacaaaag gtattagcct cactcatcat    3960
```

```
tcgcctggcc ctggctgaaa cgttctgcct caactgtggc atcattgcct tggatgagcc    4020
aacaacaaat cttgaccgag aaaacattga atctcttgca catgctctgg ttgagataat    4080
aaaaagtcgc tcacagcagc gtaacttcca gcttctggta atcactcatg atgaagattt    4140
tgtggagctt ttaggacgtt ctgaatatgt ggagaaattc tacaggatta aaagaacat     4200 cgatcagtgc tcagagattg tgaaatgcag tgttagctcc ctgggattca atgttcatta    4260
aaaatatcca agatttaaat gccatagaaa tgtaggtcct cagaaagtgt ataataagaa    4320
acttatttct catatcaact tagtcaataa gaaaatatat tctttcaaag gaacattgtg    4380
tctaggattt tggatgttga gaggttctaa aatcatgaaa cttgtttcac tgaaaattgg    4440
acagattgcc tgtttctgat ttgctgctct tcatcccatt ccaggcagcc tctgtcaggc    4500
cttcagggtt cagcagtaca gccgagactc gactctgtgc ctccctcccc agtgcaaatg    4560
catgcttctt ctcaaagcac tgttgagaag gagataatta ctgccttgaa aatttatggt    4620 tttggtatt ttttaaatca tagttaaatg ttacctctga atttacttcc ttgcatgtgg     4680
tttgaaaaac tgagtattaa tatctgagga tgaccagaaa tggtgagatg tatgtttggc    4740 tctgcttta actttataaa tccagtgacc tctctctctg ggacttggtt tccccaacta     4800
aaatttgaag tagttgaatg gggtctcaaa gtttgacagg aaccttaagt aatcatctaa    4860
gtcagtaccc accacttct tctcctacat atcccttcca gatggtcatc cagactcaga     4920
gctctctcta cagagaggaa attctccact gtgcacaccc acctttggaa agctctgacc    4980
acttgaggcc tgatctgccc atcgtgaaga agcctgtaac actcctctgc gtctatcctg    5040
tgtagcatac tggcttcacc atcaatcctg attcctctct aagtgggcat tgccatgtgg    5100
aaggcaagcc aggctcactc acagagtcaa ggcctgctcc ctgtagggtc caaccagacc    5160
tggaagaaca ggcctctcca tttgctcttc agatgccact tctaagaaaa gcctaatcac    5220 agttttcct ggaattgcca gctgacatct tgaatccttc cattccacac agaatgcaac    5280
caagtcacac gcttttgaat tatgctttgt agagttttgt cattcagagt cagccaggac    5340
cataccgggt cttgattcag tcacatggca tggttttgtg ccatctgtag ctataatgag    5400
catgtttgcc tagacagctt ttctcaactg ggtccagaag agaattaagc cctaaggtcc    5460
taaggcatct atctgtgcta ggttaaatgg ttggcccca aagatagaca ggtcctgatt     5520
tctagaaccc gtgactgtta cttttatacag caaaggaaac tttgcagatg tgattaaagc    5580
taaggacctt aagacagagt atcctggggg tggtggtggg gtggggggg gtcctaaatg      5640 taatcacgag taagattaag agcaaatcaa ttctagtcat atattaaaca tccacaataa    5700
ccaagatatt tttatcccaa gaatgcaaga tttcagaaaa tgaaaatct gttgataaat      5760 ccatcactat aataaaaccg aaggtgaaaa aaattctgaa aaaaaaaaa aaaaaaaaa       5820 aaaaaa                                                                5826
```

<210> SEQ ID NO 24
<211> LENGTH: 4737
<212> TYPE: DNA
<213> ORGANISM: Homo sapiens

<400> SEQUENCE: 24

```
ctgaggccgg cgctgcaggc agcggcggct gcgcggtgaa cgaggcggcc tgcgcggcgg      60
agtgctgagt cccgatcccc ggctctgtcc ggcccacgga tcctcaagcc cgggccccgg    120
gcccggcccc agcctcagcc ctgagcgtct cggggcggat ggcgcggggc ggcggggcg     180 ggcggtgctg agccctgcgc gggccatggc ctcggcctgc ggggcgccgg gcccgggggg    240
```

```
cgccctgggc agccaggccc cctcctggta ccaccgcgac ctgagccggg cggccgcgga    300
ggagctgctg gcccgggcgg gccgcgatgg cagcttcctg gtccgagaca gcgagagcgt    360
ggcgggggcc ttcgcgctct gcgtcctgta tcagaagcat gtgcacacgt atcgcattct    420
gcctgatgga gaagatttct tggctgtgca gacctcgcag ggtgtgcctg tgcgccgctt    480
ccagaccctg ggtgagctca tcggcctgta cgcccagccc aaccagggcc ttgtgtgcgc    540
cctgcttctt cctgtagagg gtgagcgaga gccggaccca ccggatgacc gggatgcctc    600
agatggggag gatgagaagc ccccgctgcc ccgcgctct ggctccacca gcatttctgc     660
ccccactggg cccagcagtc cctgccagc tcctgagact cccacagctc cagctgctga     720
gagtgctccc aatgggctga gcaccgtctc gcacgactac ctgaaaggca gctatgggct    780
ggacctggaa gctgtgaggg gtggagccag ccacctgccc cacctcaccc gtaccctcgc    840
tacctcatgc cggaggctgc acagtgaggt ggacaaggtc ctgtcaggcc tggagatcct    900
gtccaaggtg tttgaccagc agagctcgcc catggtgacc cgccttttgc agcagcagaa    960
cctgccacag acaggggagc aggaactaga gagcctggtg ctgaagctgt cagtgctaaa   1020
ggacttcctg tcaggcatcc agaagaaggc cctgaaggcc ctacaggaca tgagctccac   1080
agcaccccca gctccgcagc catccacacg taaggccaag accatccccg tgcaggcctt   1140
tgaggtgaag ctagatgtga ccctgggtga cctgaccaag attgggaagt cacagaagtt   1200
cacgctgagc gtggatgtgg agggtgggcg gctggtgctg ctgcggagac agcgggactc   1260
ccaggaggac tggaccacct tcacgcacga ccgcatccgc cagctcatta gtcccagcg    1320 tgtccagaac aagctgggtg ttgtgtttga aggagaagg accggactc agcgcaagga     1380 cttcatcttt gtcagtgccc ggaagcggga ggccttctgc cagctgttgc agctcatgaa   1440
gaacaagcac tccaagcagg acgagcccga catgatctca gtcttcatag gcacctggaa   1500
catgggaagt gtaccacctc caaaaaacgt gacatcctgg ttcacatcga agggtctggg   1560
gaagaccctg gacgaggtca cagtgaccat accccatgac atctatgtct ttgggaccca   1620
ggagaactca gtgggcgacc gcgagtggct ggacctactg cgcggggggcc tcaaggagct   1680 tacggatctg gattaccgcc cgattgccat gcaatcactg tggaatatca aggtggcagt   1740
gctggtcaag ccagagcacg agaaccgtat cagccatgtc agtacgtcca gtgtgaagac   1800
tggcatcgcc aacaccctgg ggaacaaggg ggctgtgggc gtctccttca tgtttaatgg   1860
cacctcattt ggctttgtga attgtcacct cacctcggga aatgagaaga cggctcggag   1920
gaaccaaaac tacttggaca tcctgcggct gctctcgctg ggcgaccggc agctcaatgc   1980
cttggacatc tctctgcgtt tcacacacct cttctggttt ggggacctca actaccgcct   2040
ggacatggat atccaggaga tcctgaacta catcagcagg aaagagtttg agcccctcct   2100
cagggtggac cagctcaacc tggagcggga aagcacaag gtcttccttc gattcagtga    2160
ggaggagatc tccttcccac ccacctaccg ctatgagcgg ggttcccggg acacatatgc   2220
ctggcacaag cagaagccaa ctggggtccg gaccaatgtg ccctcatggt gtgaccggat   2280 tctgtgggaaa tcctaccctg aaactcacat catctgcaat tcttatggtt gcactgatga   2340
catcgtcacc agcgaccatt cccccgtgtt tgggacattt gaggttggag ttacctccca   2400
gttcatctcc aagaaagggc tctcaaagac ttcagaccag gcctacattg agtttgagag   2460
catcgaggcc attgtgaaga cagccagccg caccaagttc ttcatcgagt ctactctac    2520 ctgcctggag gaatacaaga agagctttga gaatgatgcc cagagcagtg acaacatcaa   2580
cttcctcaaa gtgcagtggt cttcacgcca gctgcccacg ctcaaaccaa ttctggctga   2640
```

```
tatcgagtac ctgcaggacc agcacctcct gctcacagtc aagtccatgg atggctatga    2700
atcctatggg gagtgtgtgg ttgcactcaa atccatgatc ggcagcacgg cccaacagtt    2760
cctgaccttc ctatcccacc gtggcgagga acaggcaat atcagaggct ccatgaaggt     2820
gcgggtgccc acggagcgcc tgggcacccg tgagcggctc tacgagtgga tcagcattga    2880
taaggatgag gcaggagcaa agagcaaagc cccctctgtg tcccgaggga gccaggagcc    2940
caggtcaggg agccgcaagc cagccttcac agaggcctcc tgcccgctct ccaggttatt    3000
tgaagaacca gagaaaccgc caccaacggg gaggccccca gccccacccc gagcagctcc    3060
ccgggaggag cccttgaccc ccaggttgaa gccagaggga gctcctgaac cagaaggggt    3120
ggcggccccc ccacccaaga acagcttcaa taaccctgcc tactacgtcc ttgaaggggt    3180
cccgcaccag ctgctgcccc cggagccacc ctcgcctgcc agggcccctg tcccatctgc    3240
caccaagaac aaagtggcca ttacagtgcc tgctccacag cttgggcacc accggcaccc    3300
tcgtgtggga gaggggagtt cttcagatga ggagtctgga ggcacactgc cccctccaga    3360 cttttccacct ccaccactgc cggactcagc catcttcctg ccccccagcc tggatccttt    3420
accagggcca gtggtccggg gccgtggtgg ggctgaggcc cgtggcccac cacctcccaa    3480
ggcccatcca aggcctccac tgccccccagg cccctcacca gccagcactt tcctggggga   3540
agtgggcagt ggggatgacc ggtcctgctc ggtgctgcag atggccaaga cgctgagcga    3600
ggtggactat gcccctgctg ggcctgcacg ctcagcgctc ctcccaggcc cctggagct    3660 gcagcccccc cggggactgc cctcggacta tggccggccc ctcagcttcc ctccaccccg    3720
catccgggag agcatccagg aagacctggc agaggaggct ccgtgcctgc agggcgggcg    3780
ggccagcggg ctgggcgagg caggcatgag tgcctggctg cgggccatcg gcttggagcg    3840
ctatgaggag ggcctggtgc ataatggctg ggacgacctg gagtttctca gtgacatcac    3900
cgaggaggac ttggaggagg ctggggtgca ggacccggct cacaagcgcc tccttctgga    3960
caccctgcag ctcagcaagt gatagcggag gcaccacgaa gctgtgaact cagagcccct    4020
ccctgctacc aaggcccagc tatgcccca gggttgaaaa gttatgaggg tcagggcagt     4080
atctctctgc ctatttattg gggtgcctat ttattgggga tctgcattcc ccgctgccca    4140
atcatttgca atgccctaat tagggcatcc tgccctcgc ttttaggct caggacggaa      4200 ggtcagttgc catggttacc gaggaccctg gttactctgg tgctgtcctg ttttactgga    4260
ccccgcctcc cagccccagg ggtgcctgtg ggggtccatt gggtacgtc tgggccccca     4320 cttttcaccag tttctgcggc cttccaccgg gcctgaacca cagcggagga gctccgctaa    4380
gacctcccca ccccgctgg gggtggggc gggtgtccgt ccggaaatga aggaatagcc      4440
cgaggaccgg gctggggttt atttaaactg ttctgtgtgg gtctggggag ggagagcacc    4500
ttaatattat tgggggttggt tgggggtggg caggatctca gccataaagt gccagtttgc   4560
ttagttctca ctgtctcctg gtctgtgctg ccctgctctg gggatgcacg gcggcagggt    4620
gggggaggga ggttcctcgc aggtctcagc ccgggacagg gtcttgcaag cagcctcctg    4680
ggcagtcgta agggttgcgg cgtgatgtct tcaataaatt aagtttttatt tggaaaaa     4737
```

<210> SEQ ID NO 25
<211> LENGTH: 3231
<212> TYPE: DNA
<213> ORGANISM: Homo sapiens

<400> SEQUENCE: 25

```
ctctctcaca cacaccccg cttgggcctc ctctctctct ccggctccat ttctccgcc       60
```

```
gccggggggcc ggggtctcct gtgggggggcc cagccggtat cccaggtctc ccttcagtgc    120
cggggtgaac ccccggggga gccgggagcc ggggcagac gggcgggggt tggggcggag      180
ggagcagcgg ccccagcgag tttggggga aagtaacca ggcgggggga ggggcggagc       240
agggaggggg cctcagggcc ccccccagc tatggacgaa cggctactgg ggccgccccc     300
tccaggcggg ggccgggggg gcctgggatt ggtgagtggg gagcctgggg gccctggcga     360
gcctcccggt ggcggagacc ccggtggggg tagcggggg gtcccgggag gccgagggaa     420
gcaagacatc ggggacattc tgcagcagat aatgaccatc accgaccaga gcctggacga    480
ggcccaggcc aagaaacacg ccctaaactg ccaccgaatg aagcctgctc tctttagcgt   540
cctgtgtgaa atcaaggaga aaactggcct cagcattcgg agctcccagg aggaggagcc   600
ggtggaccca cagctgatgc gcttggacaa catgcttctg gcagagggtg tggctgggcc   660
cgagaaaggg ggcggctcag cagcagcagc tgcagccgct gcagcctctg gtggtggtgt   720
gtcccctgac aactccatcg aacactcgga ctatcgcagc aaacttgccc agatccgtca   780
catataccac tcggagctgg agaagtatga gcaggcatgt aatgagttca cgacccatgt   840
catgaacctg ctgagggagc agagccgcac caggcccgtg gccccaaag agatggaacg    900 catggtgagc atcatccatc gaaagttcag cgccatccag atgcagctga agcagagcac  960
ctgcgaggct gtgatgatcc tgcgctcccg tttcctggat gccagacgaa agcgccgtaa 1020
cttcagcaaa caggccactg aggtcctaaa tgagtatttc tactcccacc tgagtaaccc 1080
atatcctagt gaggaggcca aggaggagct tgccaagaag tgtggcatca ccgtgtctca 1140
ggtctccaac tggtttggca caagaggat tcgctataag aaaaacatcg aaagttcca   1200 agaggaggca aacatctatg ctgtcaagac cgccgtgtca gtcacccagg ggggccacag 1260
ccgcaccagc tccccgacac ccccttcctc tgcaggctct ggcggctctt tcaatctctc 1320
aggatctgga gacatgtttc tggggatgcc tgggctcaac ggagattcct attctgcttc 1380
ccaggtggaa tcactccgac actcgatggg gccaggggc tatggggata acctcggggg   1440
aggccagatg tacagcccac gggaaatgag ggcaaatggc agctggcaag aggctgtgac 1500
cccctcttca gtgacatccc caacggaggg accaggagt gttcactctg atacctccaa  1560
ctgatcttgc ccctcagggt cacaggggtg ggggctctca caaggcgact tgaagaggac 1620
gcaggcttcc agaggacaaa ccccaataca ggagaagcac aagacagaga agggccaatg 1680
gggtcatccc ctccctaacg agactctctg tgctggggt gctaattaca tggcaggaag  1740
aatggggcct ctaaggggag tgtggggtct gtctctccct ttttccatc tttttcctct   1800 ctcgctttct ttcttacaca aaacataca cataccgaga aacctatttc tcagacccct   1860
ttttctcctc tgtctttctc tctccctctc ccacacctca cacacacata ctcccacttg  1920
caactattct gtttctctcc tgggctcccc cactttccct tccccacccc acttgtatgc  1980
tctggaatct gtgagacgc cagccctgcc caatcagaga tgccaaaaat ggggacatga  2040
cttctggaca gaggacatgg gccacgcccc catgcatccc cacccccgcc cctccggacg  2100
gcttacttac ctcatacgca gctcatctta aaccaataga atcgctcggt ggacgagagt  2160
gtctgactca gatatctacc tcggaggag tttctgctac tttagggaat tattgactgg  2220
gctttggggt tgaactttt tttttttaaa gaaagaaaaa gaaaccctgg gatccatctg  2280
ttttttttgt tgttgttgtt gtttttgttg ttgttggtgg tggtggtggt ggtggttctt  2340
aatttttaat ttagtttggg gaagtagctt gtttttttt ttataaatat gttgatttct   2400
tgtctttttt tttttttatt tcttactttc ccatattagg ggtgatagcc aaagggttc    2460
```

```
tggtaagaga aagggggaca aacagaactg gtaaagaggc cccctggct ccaggcctgt    2520 ccatcaggaa gtaaatttta cagggcacca agctttgccc cctaaaatcc cttaggtgtt    2580
ctttgttcat gcaggcaggt ttctgccgca tttgatgtgg aggcagtgaa gggcttgccc    2640
tgctggcctc tcatccccct tcttcccaca acccttgggc agggctggac tcagtaattt    2700
tgaggaaatt gaagatgcca tcttcccctg tgagtgacat gtctttaatt ttttaaaaaa    2760
ctactatttg aaaattggag ggggaagaat gggaagggag ttattgccaa atatgttaaa    2820
tatgggttgg ggtgcttgta tatgtatctt cctcaatttc cccataaatg aggtatcttt    2880
ttgtcacacc aaaatcaagg ggtagggaga gggaggaggt tgcaaaaagc cagatgtggg    2940
ggaaaagtaa catcaacact gtcccatcct cagccctgaa ctagctacca tctgatcccc    3000
tcagacattc tcaggatttt acaagactgt cagagtgggg aaccctccc attaaagatc    3060 cgggcaggac tggggacagg ttggaagtgt gatgggtggg gggtgggag gcatgggccg    3120 ggggcagttc tctcctcact tgtaaacttg tgtagtttca cagaaaaaaa acaaaatgca    3180
gttttaaata aagaaatttc ttttttccct gggaaaaaaa aaaaaaaaaa a             3231

<210> SEQ ID NO 26
<211> LENGTH: 628
<212> TYPE: DNA
<213> ORGANISM: Homo sapiens

<400> SEQUENCE: 26
cctgcgtggc tgggctgctc gggttagatc gtcaggaaaa gcctaaagat tagactgtaa      60
gaaaagaaaa tagaagccat gtttcgaaga cctgtattac aggtacttcg tcagtttgta     120
agacatgagt ccgaaacaac taccagtttg gttcttgaaa gatccctgaa tcgtgtgcac     180
ttacttgggc gagtgggtca ggaccctgtc ttgagacagg tggaaggaaa aaatccagtc     240
acaatatttt ctctagcaac taatgagatg tggcgatcag gggatagtga agtttaccaa     300
ctgggtgatg tcagtcaaaa gacaacatgg cacagaatat cagtattccg gccaggcctc     360
agagacgtgg catatcaata tgtgaaaaag gggtctcgaa tttatttgga agggaaaata     420
gactatggtg aatacatgga taaaaataat gtgaggcgac aagcaacaac aatcatagct     480
gataatatta tatttctgag tgaccagacg aaagagaagg agtagaaagg atgattcttc     540
tttggccatc atttggtaca gtctcatttc caagtcatgt ataatcttta tggcttccaa     600
ggacaagaat taaaatactc ttttacgt                                         628

<210> SEQ ID NO 27
<211> LENGTH: 6405
<212> TYPE: DNA
<213> ORGANISM: Homo sapiens

<400> SEQUENCE: 27
ggtttttgag cccattactg ttggagctac agggagagaa acagaggagg agactgcaag      60
agatcattgg aggccgtggg cacgctcttt actccatgtg tgggacattc attgcggaat     120
aacatcggag gagaagtttc ccagagctat ggggacttcc catccggcgt tcctggtctt     180
aggctgtctt ctcacagggc tgagcctaat cctctgccag cttttcattac cctctatcct     240 tccaaatgaa aatgaaaagg ttgtgcagct gaattcatcc ttttctctga gatgctttgg     300
ggagagtgaa gtgagctggc agtaccccat gtctgaagaa gagagctccg atgtggaaat     360
cagaaatgaa gaaaacaaca gcggcctttt tgtgacggtc ttggaagtga gcagtgcctc     420
ggcggcccac acagggttgt acacttgcta ttacaaccac actcagacag aagagaatga     480
```

```
gcttgaaggc aggcacattt acatctatgt gccagaccca gatgtagcct ttgtacctct   540
aggaatgacg gattatttag tcatcgtgga ggatgatgat tctgccatta taccttgtcg   600
cacaactgat cccgagactc ctgtaacctt acacaacagt gagggggtgg tacctgcctc   660
ctacgacagc agacagggct ttaatgggac cttcactgta gggccctata tctgtgaggc   720
caccgtcaaa ggaagaagt tccagaccat cccatttaat gtttatgctt aaaaagcaac   780
atcagagctg gatctagaaa tggaagctct aaaaccgtg tataagtcag gggaaacgat   840
tgtggtcacc tgtgctgttt ttaacaatga ggtggttgac cttcaatgga cttaccctgg   900
agaagtgaaa ggcaaaggca tcacaatgct ggaagaaatc aaagtcccat ccatcaaatt   960
ggtgtacact ttgacggtcc ccgaggccac ggtgaaagac agtggagatt acgaatgtgc  1020
tgcccgccag gctaccaggg aggtcaaaga aatgaagaaa gtcactattt ctgtccatga  1080
gaaaggtttc attgaaatca acccaccctt cagccagttg gaagctgtca acctgcatga  1140
agtcaaacat tttgttgtag aggtgcgggc ctacccacct cccaggatat cctggctgaa  1200
aaacaatctg actctgattg aaaatctcac tgagatcacc actgatgtgg aaaagattca  1260
ggaaataagg tatcgaagca aattaaagct gatccgtgct aaggaagaag acagtggcca  1320
ttatactatt gtagctcaaa atgaagatgc tgtgaagagc tatacttttg aactgttaac  1380
tcaagttcct tcatccattc tggacttggt cgatgatcac catggctcaa ctggggcaca  1440
gacggtgagg tgcacagctg aaggcacgcc gcttcctgat attgagtgga tgatatgcaa  1500
agatattaag aaatgtaata atgaaacttc ctggactatt ttggccaaca atgtctcaaa  1560
catcatcacg gagatccact cccgagacag gagtaccgtg gagggccgtg tgactttcgc  1620
caaagtggag gagaccatcg ccgtgcgatg cctggctaag aatctccttg gagctgagaa  1680
ccgagagctg aagctggtgg ctcccaccct gcgttctgaa ctcacggtgg ctgctgcagt  1740
cctggtgctg ttggtgattg tgatcatctc acttattgtc ctggttgtca tttggaaaca  1800
gaaaccgagg tatgaaattc gctggagggt cattgaatca atcagcccag atggacatga  1860
atatatttat gtggacccga tgcagctgcc ttatgactca agatgggagt ttccaagaga  1920
tggactagtg cttggtcggg tcttggggtc tggagcgttt gggaaggtgg ttgaaggaac  1980
agcctatgga ttaagccggt cccaacctgt catgaaagtt gcagtgaaga tgctaaaacc  2040
cacggccaga tccagtgaaa aacaagctct catgtctgaa ctgaagataa tgactcacct  2100
ggggccacat ttgaacattg taaacttgct gggagcctgc accaagtcag gccccattta  2160
catcatcaca gagtattgct tctatggaga tttggtcaac tatttgcata gaataggga   2220 tagcttcctg agccaccacc cagaagaagcc aaagaaagag ctggatatct ttggattgaa  2280
ccctgctgat gaaagcacac ggagctatgt tattttatct tttgaaaaca atggtgacta  2340
catggacatg aagcaggctg atactacaca gtatgtcccc atgctagaaa ggaaagaggt  2400
ttctaaatat tccgacatcc agagatcact ctatgatcgt ccagcctcat ataagaagaa  2460
atctatgtta gactcagaag tcaaaaaacct cctttcagat gataactcag aaggccttac  2520
tttattggat ttgttgagct tcacctatca agttgcccga ggaatggagt ttttggcttc  2580
aaaaaattgt gtccaccgtg atctggctgc tcgcaacgtc ctcctggcac aaggaaaaat  2640
tgtgaagatc tgtgactttg gcctggccag agacatcatg catgattcga actatgtgtc  2700
gaaaggcagt accttttctgc ccgtgaagtg gatggctcct gagagcatct ttgacaacct  2760
ctacaccaca ctgagtgatg tctggtctta tggcattctg ctctgggaga tcttttccct  2820
tggtggcacc ccttaccccg gcatgatggt ggattctact ttctacaata agatcaagag  2880
```

-continued

```
tgggtaccgg atggccaagc ctgaccacgc taccagtgaa gtctacgaga tcatggtgaa    2940
atgctggaac agtgagccgg agaagagacc ctccttttac cacctgagtg agattgtgga    3000
gaatctgctg cctggacaat ataaaaagag ttatgaaaaa attcacctgg acttcctgaa    3060
gagtgaccat cctgctgtgg cacgcatgcg tgtggactca gacaatgcat acattggtgt    3120
cacctacaaa aacgaggaag acaagctgaa ggactgggag ggtggtctgg atgagcagag    3180
actgagcgct gacagtggct acatcattcc tctgcctgac attgaccctg tccctgagga    3240
ggaggacctg ggcaagagga acagacacag ctcgcagacc tctgaagaga gtgccattga    3300
gacgggttcc agcagttcca ccttcatcaa gagagaggac gagaccattg aagacatcga    3360
catgatggac gacatcggca tagactcttc agacctggtg gaagacagct tcctgtaact    3420
ggcggattcg aggggttcct tccacttctg gggccacctc tggatcccgt tcagaaaacc    3480
actttattgc aatgcggagg ttgagaggag gacttggttg atgtttaaag agaagttccc    3540
agccaagggc ctcgggagc gttctaaata tgaatgaatg ggatattttg aaatgaactt    3600
tgtcagtgtt gcctcttgca atgcctcagt agcatctcag tggtgtgtga agtttggaga    3660
tagatggata agggaataat aggccacaga aggtgaactt tgtgcttcaa ggacattggt    3720
gagagtccaa cagacacaat ttatactgcg acagaacttc agcattgtaa ttatgtaaat    3780
aactctaacc aaggctgtgt ttagattgta ttaactatct tctttggact tctgaagaga    3840
ccactcaatc catccatgta cttccctctt gaaacctgat gtcagctgct gttgaacttt    3900
ttaaagaagt gcatgaaaaa ccattttttga accttaaaag gtactggtac tatagcattt    3960
tgctatcttt tttagtgtta aagagataaa gaataataat taaccaacct tgtttaatag    4020
atttgggtca tttagaagcc tgacaactca ttttcatatt gtaatctatg tttataatac    4080
tactactgtt atcagtaatg ctaaatgtgt aataatgtaa catgatttcc ctccagagaa    4140
agcacaattt aaaacaatcc ttactaagta ggtgatgagt ttgacagttt ttgacattta    4200
tattaaataa catgtttctc tataaagtat ggtaatagct ttagtgaatt aaatttagtt    4260
gagcatagag aacaaagtaa aagtagtgtt gtccaggaag tcagaatttt taactgtact    4320
gaataggttc cccaatccat cgtattaaaa aacaattaac tgccctctga ataatgggga    4380
ttagaaacaa acaaaactct taagtcctaa aagttctcaa tgtagaggca taaacctgtg    4440
ctgaacataa cttctcatgt atattaccca atggaaaata taatgatcag caaaaagact    4500
ggatttgcag aagttttttt tttttttttc ttcatgcctg atgaaagctt ggcgacccc    4560 aatatatgta ttttttgaat ctatgaacct gaaagggtc agaaggatgc ccagacatca    4620
gcctccttct ttcacccctt accccaaaga gaaagagttt gaaactcgag accataaaga    4680
tattctttag tggaggctgg atgtgcatta gcctggatcc tcagttctca aatgtgtgtg    4740
gcagccagga tgactagatc ctgggttttcc atccttgaga ttctgaagta tgaagtctga    4800
gggaaaccag agtctgtatt tttctaaact ccctggctgt tctgatcggc cagttttcgg    4860
aaacactgac ttaggtttca ggaagttgcc atgggaaaca aataatttga actttggaac    4920
agggttggaa ttcaaccacg caggaagcct actatttaaa tccttggctt caggttagtg    4980
acatttaatg ccatctagct agcaattgcg accttaattt aactttccag tcttagctga    5040
ggctgagaaa gctaaagttt ggttttgaca ggttttccaa aagtaaagat gctacttccc    5100
actgtatggg ggagattgaa ctttcccccgt ctcccgtctt ctgcctccca ctccataccc    5160
cgccaaggaa aggcatgtac aaaaattatg caattcagtg ttccaagtct ctgtgtaacc    5220
agctcagtgt tttggtggaa aaaacatttt aagttttact gataatttga ggttagatgg    5280
```

```
gaggatgaat tgtcacatct atccacactg tcaaacaggt tggtgtgggt tcattggcat    5340
tctttgcaat actgcttaat tgctgatacc atatgaatga acatgggct gtgattactg     5400 caatcactgt gctatcggca gatgatgctt tggaagatgc agaagcaata ataaagtact    5460
tgactaccta ctggtgtaat ctcaatgcaa gccccaactt tcttatccaa cttttttcata  5520 gtaagtgcga agactgagcc agattggcca attaaaaacg aaaacctgac taggttctgt    5580
agagccaatt agacttgaaa tacgtttgtg tttctagaat cacagctcaa gcattctgtt    5640
tatcgctcac tctcccttgt acagccttat tttgttggtg ctttgcattt tgatattgct    5700
gtgagccttg catgacatca tgaggccgga tgaaacttct cagtccagca gtttccagtc    5760
ctaacaaatg ctcccacctg aatttgtata tgactgcatt tgtgtgtgtg tgtgtgtttt    5820
cagcaaattc cagatttgtt tccttttggc ctcctgcaaa gtctccagaa gaaaatttgc    5880 caatcttttcc tactttctat ttttatgatg acaatcaaag ccggcctgag aaacactatt    5940
tgtgactttt taaacgatta gtgatgtcct taaaatgtgg tctgccaatc tgtacaaaat    6000
ggtcctattt ttgtgaagag ggacataaga taaaatgatg ttatacatca atatgtatat    6060
atgtatttct atatagactt ggagaatact gccaaaacat ttatgacaag ctgtatcact    6120
gccttcgttt atattttttt aactgtgata atccccacag gcacattaac tgttgcactt    6180
ttgaatgtcc aaaatttata ttttagaaat aataaaaaga aagatactta catgttccca    6240
aaacaatggt gtggtgaatg tgtgagaaaa actaacttga tagggtctac caatacaaaa    6300
tgtattacga atgcccctgt tcatgttttt gttttaaaac gtgtaaatga agatctttat    6360
atttcaataa atgatatata atttaaagtt aaaaaaaaaa aaaaa                    6405

<210> SEQ ID NO 28
<211> LENGTH: 1703
<212> TYPE: DNA
<213> ORGANISM: Homo sapiens

<400> SEQUENCE: 28
ttgggcgcca caccttgcgc gccccggggc ccaaggagac gaccctgaag aggagcctgg      60
ctacttttgc ctcagacgag tccggagcgc cgggttaacc ggtctgaagt cccaggggct    120
ttctgggact gctcagccac cggcagcttc cggcaccagg ggacgccgga cgccgtccgg    180
acattcggcg cgcttgccac gatcttggac gggtctcggg cctcgacctt tgaattcccc    240
gctccggctc caagatgtca gcaacgctga tcctggagcc cccaggccgc tgctgctgga    300
acgagccggt gcgcattgcc gtgcgcggcc tggccccgga gcagcgggtt acgctgcgcg    360
cgtccctgcg cgacgagaag ggcgcgctct ccgggcccca cgcgcgctac tgcgccgacg    420
cctgcggcga gctggacctg agcgcgcac ccgcgctggg cggcagcttc gcgggactcg     480
agcccatggg gctgctctgg gccctggaac ccgagaagcc tttttggcgc ttcctgaagc    540
gggacgtaca gattcctttt gtcgtggagt tggaggtgct ggacggccac gaccccgagc    600
ctggacggct gctgtgccag gcgcagcacg agcgccactt cctcccgcca ggggtgcggc    660
gccagtcggt gcgagcgggc cgggtgcgcg ccacgctctt cctgccgcca ggacctggac    720
ccttcccagg gatcattgac atctttggta ttggagggggg cctcttggaa tatcgagcca    780
gcctccttgc tggccatggc tttgccacgt ggctctagc ttattataac tttgaagatc    840
tccccaataa catggacaac atatccctgg agtacttcga agaagccgta tgctacatgc    900
ttcaacatcc ccaggtaaaa ggcccaggca ttgggctttt gggcatttct ctaggagctg    960
atatttgtct ctcaatggcc tcattcttga agaatgtctc agccacagtt ccatcaatg    1020
```

```
gatctgggat cagtgggaac acagccatca actataagca cagtagcatt ccaccattgg   1080
gctatgacct gaggagaatc aaggtagctt tctcaggcct cgtggacatc gtggatataa   1140
ggaatgctct cgtaggaggg tacaagaacc ccagcatgat tccaatagag aaggcccagg   1200
ggcccatcct gctcattgtt ggtcaggatg accataactg gagaagtgag ttgtatgccc   1260
aaacagtctc tgaacggtta caggcccatg gaaaggaaaa accccagatc atctgttacc   1320
ctgggactgg gcattacatc gagcctcctt acttccccct gtgcccagct tcccttcaca   1380
gattactgaa caaacatgtt atatggggtg gggagcccag ggctcattct aaggcccagg   1440
aagatgcctg gaagcaaatt ctagccttct tctgcaaaca cctgggaggt acccagaaaa   1500
cagctgtccc taaattgtaa tgcatttgtc tgttgttgac atgagagatt caagatcaga   1560
ttctagtgtt cagtaaccct atgtgaatca gatgtctcct ggataacatt aaagccatgt   1620
ctttgtcatt aaaaaaaaaa aaaaaaaaaa aaaaaaaaaa aaaaaaaaaa aaaaaaaaaa   1680
aaaaaaaaaa aaaaaaaaaa aaa                                          1703

<210> SEQ ID NO 29
<211> LENGTH: 2144
<212> TYPE: DNA
<213> ORGANISM: Homo sapiens

<400> SEQUENCE: 29
aatccacctc ccaccagggc acttccggcg gcgctctccg cgccttatcg ccaaagctgc     60
ggctctggac gcccagccgc ggcgtatccc gatcacttcc gggtagtgct ccacgggcac    120
gagccgcgat tgggctaccg tagatggggt acttccggtg tgcaggtgct gggtccttcg    180
gcaggaggag gaagatggag cccagcaccg cggcccgggc ttgggccctc ttttggttgc    240
tgctgccctt gcttggcgcg gtttgcgcca gcggaccccg caccttagtg ctgctggaca    300
acctcaacgt gcgggagact cattcgcttt tcttccggag cctgaaggac cggggctttg    360
agctcacatt caagaccgct gatgaccca gcctgtctct cataaagtat ggggaattcc    420
tctatgacaa tctcatcatt ttctccccctt cggtagaaga ttttggaggc aacatcaacg    480
tggagaccat cagtgccttt attgacggcg gaggcagtgt gctggtagct gccagctccg    540
acattggtga ccctcttcga gagctgggca gtgagtgcgg gattgagttt gacgaggaga    600
aaacggctgt cattgaccat cacaactatg acatctcaga ccttggccag catacgctca    660
tcgtggctga cactgagaac ctgctgaagg ccccaaccat cgttgggaaa tcatctctaa    720
atcccatcct ctttcgaggt gttgggatgg tggccgatcc tgataaccct ttggtgctgg    780
acatcctgac gggctcttcc acctcttact ccttcttccc ggacaagcct atcacccagt    840
atccacatgc ggtggggaag aacaccctcc tcattgctgg gctccaggcc aggaacaatg    900
cccgcgtcat cttcagcggc tccctcgact tcttcagcga ctccttcttc aactcagcag    960
tgcagaaggc ggcgcccggc tcccagaggt attcccagac aggcaactat gaactagctg   1020
tggccctctc ccgctgggtg ttcaaggagg agggtgtcct ccgtgtgggg cctgtgtccc   1080
atcatcgggt gggcgagaca gccccacccca atgcctacac tgtcactgac ctagtggagt   1140
atagcatcgt gatccagcag ctctcaaatg gcaaatgggt cccctttgat ggcgatgaca   1200
ttcagctgga gtttgtccgc attgatcctt tgtgaggac cttcctgaag aagaaaggtg   1260
gcaaatacag tgttcagttc aagttgcccg acgtgtatgg tgtattccag tttaaagtgg   1320
attacaaccg gctaggctac acacacctgt actcttccac tcaggtatcc gtgcggccac   1380
tccagcacac gcagtatgag cgcttcatcc cctcggccta ccctactac gccagcgcct   1440
```

```
tctccatgat gctggggctc ttcatcttca gcatcgtctt cttgcacatg aaggagaagg   1500
agaagtccga ctgaggggct agagccctct ccgcacagcg tggagacggg gcaaggaggg   1560
gggttattag gattggtggt tttgttttgc tttgtttaaa gccgtgggaa aatggcacaa   1620
ctttacctct gtgggagatg caacactgag agccaagggg tgggagttgg gataattttt   1680
atataaaaga agttttttcca ctttgaattg ctaaaagtgg cattttttcct atgtgcagtc   1740 actcctctca tttctaaaat agggacgtgg ccaggcacgg tggctcatgc ctgtaatccc   1800
agcactttgg gaggccgagg caggcggctc acgaggtcag gagatcgaga ctatcctggc   1860
taacacggta aaaccctgtc tctactaaaa gtacaaaaaa ttagctgggc gtggtggtgg   1920
gcacctgtag tcccagctac tcgggaggct gaggcaggag aaaggcatga atccaagagg   1980
cagagcttgc agtgagctga gatcacgcca ttgcactcca gcctgggcaa cagtgttaag   2040
actctgtctc aaatataaat aaataaataa ataaataaat aaataaataa aaataaagcg   2100
agatgttgcc ctcaaacttc acctggaaaa aaaaaaaaaa aaaa   2144

<210> SEQ ID NO 30
<211> LENGTH: 3590
<212> TYPE: DNA
<213> ORGANISM: Homo sapiens

<400> SEQUENCE: 30
agctctggga caggagccca gcactagaag ttggcggtgt ttcccctcgg tgatcagcac     60
tgaagacaga ggactcacca tggagtttgg gctgagctgg gttttcctcg ttgctctttt    120
aagaggtgtc cagtgtcagg tgcagttggt ggagtctggg ggaggcgtgg tccggcctgg    180
ggcgtccctg agactctcct gtgcagcgtc tggattcaac ttcaaggact atgtcatgca    240
ttgggtccgc caggctccag gcaaggggct tgagtgggtg gccgttgcgt gggacgtagg    300
aattcccatt cattatgcag actccgtcaa gggccgattc accatctcga gagacaactc    360
caagaatacc ctctatttgc aaatggatag cctgaaagtc gaggacacgg ctgtctatta    420
ttgtgtgaga gattggggggg acgatgacta cagtagtaaa tactattact acactctgga    480 cgtctgggggc cgagggacaa cggtcaccgt ctcctcaagt aagagtggcc attttagggc    540
ctttattttg tcttagtgcg tgcggcggtt cctgagcatt gcaagttggt cctcggggcg    600
tgttccgagg ggtcctgggc ggcctggcca ggaggggacg ggcactgggg tgccttgagg    660
ctctgggaga ctccgtggat tttccggtgg cttttgaaaaa tgggactctg atgcagagaa    720
tgagcccggg ggttggggag gcacatttgg acgagatgcc tgaagaaacc aggggtctca    780
gcgatggcta aggaatgtgt ctcaggagtg gtgtctgtcg gactgcagga tggctgcaat    840
cgtgaaagct tttctctaga cttgtgaggt gcgctgtggg tctacctgca tgttaaagta    900
tttattggct ggaaagagaa ttggcggagt gggtgaatcc agccaggggg gacgcgtagc    960
cccggcctcg atgacagcag ggtcggggggc agggtagcc cagaaacagt ggctgccgtc   1020
ctgacagggg cttagggagg ctccaggacc tcagggcctt gaagctggtt tccatgagaa   1080
aaggattgtt tatcctagga ggcatgcata ttgttaaagg acaggatatg tttgaagtgg   1140
cttctgagaa aaagggttaa gaaaattctg acttaaaaat gtgagagact ttcaagtgta   1200
ttaatttttt taactgtcca agtatttgag attcttatca tttcattaac acccatgagt   1260
gatatgtgtc cggaattgag gccaaagcaa gctcagctaa gaaatactag cacagtgctg   1320
tcggccccga tgcgggactg cgttttgacc atcgtaaatc aactttcttt ttttaattaa   1380
ttgagcgaag ctggaagcag atgatgaatg agagtcaaga tggctgcatg ggggtctccg   1440
```

```
gcacccacag caggtggcag gaagcaggtc accgcgagag tctatttag gaagcaaaaa      1500 aacacaattg gtaaatttat cacttctggt tgtgaagagg tggttttgcc caggcccaga      1560
tctgaaagtg ctctactgag caaaacaaca cctggacaat ttgcgtttct aaaataaggc      1620
gaggctgacc gaaactgaaa aggctttttt taactatctg aatttcattt ccaatcttag      1680
cttatcaact gctagtttgt gcaaacagca tatcaacttc taaactgcat tcattttaa       1740 agtaagatgt ttaagaaatt aaacagtctt agggagagtt tatgactgta ttcaaaaagt      1800
tttttaaatt agcttgttat ccccttcatgt gataactaat ctcaaatact ttttcgatac     1860
ctcagagcat tattttcata atgactgtgt tcacaatctt tttaggttaa ctcgttttct      1920
ctttgtgatt aaggagaaac actttgtatat tctgatagag tggccttcat tttagtattt    1980
ttcaagacca cttttcaact actcacttta ggataagttt taggtaaaat gtgcatcact      2040
atcctgaatt atttcagtta agcatgttag ttggtggcat aagagaaaac tcaatcagat      2100
agtgctgaag acaggactgt ggagacacct tagaaggaca gattctgttc cgaatcaccg      2160
atgcggcgtc agcaggactg gcctagcgga ggctctggga gggtgactgc caggcccggc      2220
ctgggctttg ggtctccccg gactaccag agctgggacg cgtggcttct gctgccgggc      2280
cgactggctg ctccggcccc agcccttgtt aatggacttg gaggaatgat tccatgccaa      2340
agctttgcaa ggctcgcagt gaccaggcgc ccgacatgct ttcagaaatg gactcagatg     2400
ggcaaaactg acctaagctg acctagacta acaaggctg aactgagctg acctgagctg      2460
agctgggcta agttggacca gcatcccga ccagccccaa ggtcttcccg ctgagcctct      2520
gcagcaccca gccagatggg aacgtggtca tcgcctgcct ggtccagggc ttcttccccc     2580
aggagccact cagtgtgacc tggagcgaaa gcggacaggg cgtgaccgcc agaaacttcc      2640
cacccagcca ggatgcctcc ggggacctgt acaccacgag cagccagctg accctgccgg     2700
ccacacagtg cctagccggc aagtccgtga catgccacgt gaagcactac acgaatccca      2760
gccaggatgt gactgtgccc tgcccagttc cctcaactcc acctaccccca tctccctcaa     2820 ctccacctac cccatctccc tcatgctgcc accccgact gtcactgcac cgaccggccc      2880
tcgaggacct gctcttaggt tcagaagcga acctcacgtg cacactgacc ggcctgagag      2940
atgcctcagg tgtcaccttc acctggacgc cctcaagtgg gaagagcgct gttcaaggac      3000
cacctgaccg tgacctctgt ggctgctaca gcgtgtccag tgtcctgccg ggctgtgccg     3060
agccatggaa ccatgggaag accttcactt gcactgctgc ctaccccgag tccaagaccc     3120
cgctaaccgc caccctctca aaatccggaa acacattccg gcccgaggtc cacctgctgc     3180
cgccgccgtc ggaggagctg gccctgaacg agctggtgac gctgacgtgc ctggcacgtg     3240
gcttcagccc caaggatgtg ctggttcgct ggctgcaggg gtcacaggag ctgccccgcg     3300
agaagtacct gacttgggca tcccggcagg agcccagcca gggcaccacc accttcgctg     3360
tgaccagcat actgcgcgtg gcagccgagg actggaagaa ggggacacc ttctcctgca       3420 tggtgggcca cggggccctg ccgctggcct tcacacagaa gaccatcgac cgcttggcgg     3480
gtaaacccac ccatgtcaat gtgtctgttg tcatggcgga ggtggacggc acctgctact     3540
gagccgcccg cctgtcccca cccctgaata aactccatgc tcccccaagc                3590
```

<210> SEQ ID NO 31
<211> LENGTH: 510
<212> TYPE: DNA
<213> ORGANISM: Homo sapiens

<400> SEQUENCE: 31

```
tgaggctgcc ttataaagca ccaagaggct gccagtggga cattttctcg gccctgccag        60
cccccaggag gaaggtgggt ctgaatctag caccatgacg gaactagaga cagccatggg       120
catgatcata gacgtctttt cccgatattc gggcagcgag ggcagcacgc agaccctgac       180 caaggggggag ctcaaggtgc tgatggagaa ggagctacca ggcttcctgc agagtggaaa      240
agacaaggat gccgtggata aattgctcaa ggacctggac gccaatggag atgcccaggt       300
ggacttcagt gagttcatcg tgttcgtggc tgcaatcacg tctgcctgtc acaagtactt       360
tgagaaggca ggactcaaat gatgccctgg agatgtcaca gattcctggc agagccatgg       420
tcccaggctt cccaaaagtg tttgttggca attattcccc taggctgagc ctgctcatgt       480
acctctgatt aataaatgct tatgaaatga                                        510

<210> SEQ ID NO 32
<211> LENGTH: 14773
<212> TYPE: DNA
<213> ORGANISM: Homo sapiens

<400> SEQUENCE: 32
ctgggcggcc gggcgcgggg agagggcgcg ggagcggctc gtgcggcagg taccatgcgg        60
acgcgcgagc ccggcgaggg ccccggcagg cccggtccct gctcggggggc gcgctgagac      120 ggcgggtgag ctccacgaga gcgccgtcgc cacttcgggc caactttgcg attcccgaca       180
gttaagcaat ggggagacat ttggctttgc tcctgcttct gctccttctc ttccaacatt       240
ttggagacag tgatggcagc caacgacttg aacagactcc tctgcagttt acacacctcg       300
agtacaacgt caccgtgcag gagaactctg cagctaagac ttatgtgggg catcctgtca       360
agatgggtgt ttacattaca catccagcgt gggaagtaag gtacaaaatt gtttccggag       420
acagtgaaaa cctgttcaaa gctgaagagt acattctcgg agacttttgc tttctaagaa       480
taaggaccaa aggaggaaat acagctattc ttaatagaga agtgaaggat cactacacat       540
tgatagtgaa agcacttgaa aaaaatacta atgtggaggc gcgaacaaag gtcagggtgc       600
aggtgctgga tacaaatgac ttgagaccgt tattctcacc cacctcatac agcgtttctt       660
tacctgaaaa cacagctata aggaccagta tcgcaagagt cagcgccacg gatgcagaca       720
taggaaccaa cggggaattt tactacagtt ttaaagatcg aacagatatg tttgctattc       780
acccaaccag tggtgtgata gtgttaactg gtagacttga ttacctagag accaagctct       840
atgagatgga aatcctcgct gcggaccgtg gcatgaagtt gtatgggagc agtggcatca       900
gcagcatggc caagctaacg gtgcacatcg aacaggccaa tgaatgtgct ccggtgataa       960
cagcagtgac attgtcacca tcagaactgg acagggaccc agcatatgca attgtgacag      1020
tggatgactg cgatcagggt gccaatggtg acatagcatc tttaagcatc gtggcaggtg      1080
accttctcca gcagtttaga acagtgaggt ccttttccagg gagtaaggag tataaagtca      1140
aagccatcgg tggcattgat tgggacagtc atcctttcgg ctacaatctc acactacagg      1200
ctaaagataa aggaactccg cccccagttct cttctgttaa agtcattcac gtgacttctc      1260
cacagttcaa agccgggcca gtcaagtttg aaaaggatgt ttacagagca gaaataagtg      1320
aatttgctcc tcccaacaca cctgtggtca tggtaaaggc cattcctgct tattcccatt      1380
tgaggtatgt ttttaaaagt acacctgaaa aagctaaatt cagtttaaat tacaacactg      1440
gtctcatttc tatttttagaa ccagttaaaa gacagcaggc agcccatttt gaacttgaag      1500
taacaacaag tgacagaaaa gcgtccacca aggtcttggt gaaagtctta ggtgcaaata      1560
gcaatccccc tgaatttacc cagacagcgt acaaagctgc ttttgatgag aacgtgccca      1620
```

```
ttggtactac tgtcatgagc ctgagtgccg tagaccctga tgagggtgag aacgggtacg   1680
tgacatacag tatcgcaaat ttaaatcatg tgccgtttgc gattgaccat ttcactggtg   1740
ccgtgagtac gtcagaaaac ctggactacg aactgatgcc tcgggtttat actctgagga   1800
ttcgtgcatc agactggggc ttgccgtacc gccgggaagt cgaagtcctt gctacaatta   1860
ctctcaataa cttgaatgac aacacacctt tgtttgagaa aataaattgt gaagggacaa   1920
ttcccagaga tctaggcgtg ggagagcaaa taaccactgt ttctgctatt gatgcagatg   1980
aacttcagtt ggtacagtat cagattgaag ctggaaatga actggatttc tttagtttaa   2040
accccaactc gggggtattg tcattaaagc gatcgctaat ggatggctta ggtgcaaagg   2100
tgtctttcca cagtctgaga atcacagcta cagatggaga aaattttgcc acaccattat   2160
atatcaacat aacagtggct gccagtcaca agctggtaaa cttgcagtgt gaagagactg   2220
gtgttgccaa aatgctggca gagaagctcc tgcaggcaaa taattacac aaccagggag   2280 aggtggagga tattttcttc gattctcact ctgtcaatgc tcacataccg cagtttagaa   2340
gcactcttcc gactggtatt caggtaaagg aaaaccagcc tgtgggttcc agtgtaattt   2400
tcatgaactc cactgacctt gacactggct tcaatgaaaa actggtctat gctgtttctg   2460
gaggaaatga ggatagttgc ttcatgattg atatggaaac aggaatgctg aaaattttat   2520
ctcctcttga ccgtgaaaca acagacaaat acacctgaa tattaccgtc tatgaccttg   2580
ggatacccca gaaggctgcg tggcgtcttc tacatgtcgt ggttgtcgat gccaatgata   2640
atccacccga gttttacag gagagctatt ttgtggaagt gagtgaagac aaggaggtac   2700
atagtgaaat catccaggtt gaagccacag ataaagacct ggggcccaac ggacacgtga   2760
cgtactcaat tgttacagac acagacacat tttcaattga cagcgtgacg ggtgttgtta   2820
acatcgcacg ccctctggat cgagagctgc agcatgagca ctccttaaag attgaggcca   2880
gggaccaagc cagagaagag cctcagctgt tctccactgt cgttgtgaaa gtatcactag   2940
aagatgttaa tgacaaccca cctacatta ttccacctaa ttatcgtgtg aaagtccgag   3000
aggatcttcc agaaggaacc gtcatcatgt ggttagaagc ccacgatcct gatttaggtc   3060
agtctggtca ggtgagatac agccttctgg accacggaga aggaaacttc gatgtggata   3120
aactcagtgg agcagttagg atcgtccagc agttggactt tgagaagaag caagtgtata   3180
atctcactgt gagggccaaa gacaagggaa agccagtttc tctgtcttct acttgctatg   3240
ttgaagttga ggtggttgat gtgaatgaga acctgcaccc accgtgtttt ccagctttg   3300 tggaaaaggg gacagtgaaa gaagatgcac ctgttggttc attggtaatg acggtgtcgg   3360
ctcatgatga ggacgccaga agagatgggg agatccgata ctccattaga gatggctctg   3420
gcgttggtgt tttcaaaata ggtgaagaga caggtgtcat agagacgtca gatcgactgg   3480
accgtgaatc gacctcccat tattggctaa cagtctttgc aaccgatcag ggtgtcgtgc   3540
ctctttcatc gttcatagag atctacatag aggttgagga tgtcaatgac aatgcaccac   3600
agacatcaga gcctgtttat tacccagaaa tcatggaaaa ttctcctaaa gatgtatctg   3660
tggtccagat cgaggcattt gatccagatt cgagctctaa tgcaagctc atgtacaaaa   3720 ttacaagtgg aaatccacaa ggattctttt caatacatcc taaaacaggt ctcatcacaa   3780
ctacgtcaag gaagctagac cgagaacagc aagatgaaca catattagag gttactgtga   3840
cagacaatgg tagtccccc aaatcaacca ttgcaagagt cattgtgaaa atccttgatg   3900
aaaatgacaa caaacctcag tttctgcaaa agttctacaa aatcagactc cctgagcggg   3960
aaaagccaga ccgagaaaga aatgccagac gggagccgct ctatcacgtc atagccaccg   4020
```

```
acaaggatga gggccccaat gcagaaatct cctacagcat cgaagacggg aatgagcatg    4080
gcaaattttt catcgaaccg aaaactggag tggtttcgtc aagaggtttt tcagcagctg    4140
gagaatatga tattctttca attaaggcag ttgacaatgg tcgccctcaa aagtcatcaa    4200
ccaccagact ccatattgaa tggatctcca agcccaaacc gtccctggag cccatttcat    4260
ttgaagaatc attttttacc tttactgtga tggaaagtga ccccgttgct cacatgattg    4320
gagtaatatc tgtggagcct cctggcatac ccctttggtt tgacatcact ggtggcaact    4380
acgacagtca cttcgatgtg gacaagggaa ctggaaccat cattgttgcc aaacctcttg    4440
atgcagaaca gaagtcaaac tacaacctca cagtcgaggc tacagatgga accaccacta    4500
tcctcactca ggtattcatc aaagtaatag acacaaatga ccatcgtcct cagttttcta    4560
catcaaagta tgaagttgtt attcctgaag atacagcgcc agaaacagaa attttgcaaa    4620
tcagtgctgt ggatcaggat gagaaaaaca aactaatcta cactctgcag agcagtagag    4680
atccactgag tctcaagaaa tttcgtcttg atcctgcaac cggctctctc tatacttctg    4740
agaaactgga tcatgaagct gttcaccagc acaccctcac ggtcatggta cgagatcaag    4800
atgtgcctgt aaaacgcaac tttgcaagga ttgtggtcaa tgtcagcgac acgaatgacc    4860
acgccccgtg gttcaccgct tcctcctaca aaggcgggt ttatgaatcg cagccgttg    4920 gctcagttgt gttgcaggtg acggctctgg acaaggacaa agggaaaaat gctgaagtgc    4980
tgtactcgat cgagtcagga atattggaa attctttat gattgatcct gtcttgggct    5040
ctattaaaac tgccaaagaa ttagatcgaa gtaaccaagc ggagtatgat ttaatggtaa    5100
aagctacaga taagggcagt ccaccaatga gtgaaataac ttctgtgcgt atctttgtca    5160
caattgctga caacgcctct ccgaagttta tcaaaagaa atattctgtt gaacttagtg    5220
aaactgtcag cattgggagt ttcgttggga tggttacagc ccatagtcaa tcatcagtgg    5280
tgtatgaaat aaaagatgga aatacaggtg atgcttttga tattaatcca cattctggaa    5340
ctatcatcac tcagaaagcc ctggactttg aaactttgcc catttacaca ttgataatac    5400
aaggaactaa catggctggt ttgtccacta atacaacggt tctagttcac ttgcaggatg    5460
agaatgacaa cgcgccagtt tttatgcagg cagaatatac aggactcatt agtgaatcag    5520
cctcaattaa cagcgtggtc ctaacagaca ggaatgtccc actggtgatt cgagcagctg    5580
atgctgataa agactcaaat gctttgcttg tatatcacat tgttgaacca tctgtacaca    5640
catattttgc tattgattct agcactggtg ctattcatac agtactaagt ctggactatg    5700
aagaaacaag tattttttcac tttaccgtcc aagtgcatga catgggaacc ccacgtttat    5760
ttgctgagta tgcagcgaat gtaacagtac atgtaattga cattaatgac tgccccctg    5820 tgtttgccaa gccattatat gaagcatctc ttttgttacc aacatacaaa ggagtaaaag    5880
tcatcacagt aaatgctaca gatgctgatt caagtgcatt ctcacagttg atttactcca    5940
tcaccgaagg caacatcggg gagaagtttt ctatggacta caagactggt gctctcactg    6000
tccaaaacac aactcagtta agaagccgct acgagctaac cgttagagct tccgatggca    6060
gatttgccgg ccttacctct gtcaaaatta atgtgaaaga aagcaaagaa agtcacctaa    6120
agtttaccca ggatgtctac tctgcggtag tgaaagagaa ttccaccgag gccgaaacat    6180
tagctgtcat tactgctatt gggaatccaa tcaatgagcc tttgttttat cacatcctca    6240
acccagatcg cagatttaaa ataagccgca cttcaggagt tctgtcaacc actggcacgc    6300
ccttcgatcg tgagcagcag gaggcgtttg atgtggttgt agaagtgaca gaggaacata    6360
agccttctgc agtggcccac gttgtcgtga aggtcattgt agaagaccaa aatgataatg    6420
```

```
cgccggtgtt tgtcaacctt ccctactacg ccgttgttaa agtggacact gaggtgggcc    6480
atgtcattcg ctatgtcact gctgtagaca gagacagtgg cagaaacggg aagtgcatt     6540 actacctcaa ggaacatcat gaacactttc aaattggacc cttgggtgaa atttcactga    6600
aaaagcaatt tgagcttgac accttaaata agaatatct tgttacagtg gttgcaaaag    6660
atggagggaa cccggccttt tcagcggaag ttatcgttcc gatcactgtc atgaataaag    6720
ccatgcctgt gtttgaaaaa ccttttctaca gtgcagagat tgcagagagc atccaggtgc   6780
acagccctgt ggtccacgtg caggctaaca gcccggaagg cctgaaagtg ttctacagca    6840
tcacagacgg agacccttc agccagttca ctattaactt caatactgga gttatcaatg     6900
tcatagctcc tctggacttt gaggcccacc cggcatataa gctgagcata cgcgcaactg    6960
actccttgac gggcgctcat gctgaagtat ttgtggacat catagtagac gacatcaatg    7020
ataaccctcc tgtgtttgct cagcagtctt atgcggtgac cctgtctgag gcatctgtaa    7080
ttggaacgtc tgttgttcaa gttagagcca ccgattctga ttcagaaccag aatagaggaa    7140 tctcatacca gatgtttggg aatcacagca agagtcatga tcattttcat gtagacagca    7200
gcactggcct catctcacta ctcagaaccc tggattacga gcagtcccgg cagcacacga    7260
tttttgtgag ggcagttgat ggtggtatgc ccacgctgag cagtgatgtg attgtcacgg    7320
tggacgttac cgacctcaat gataatccac cactctttga acaacagatt tatgaagcca    7380
gaattagcga gcacgcccct catgggcatt tcgtgacctg tgtaaaagcc tatgatgcag    7440
acagttcaga catagacaag ttgcagtatt ccattctgtc tggcaatgat cataaacatt    7500
ttgtcattga cagtgcaaca gggattatca ccctctcaaa cctgcaccgg cacgccctga    7560
agccatttta cagtcttaac ctgtcagtgt ctgatggagt ttttagaagt tccacccagg    7620
ttcatgtaac tgtaattgga ggcaatttgc acagtcctgc tttccttcag aacgaatatg    7680
aagtggaact agctgaaaac gctccccta ataccctggt gatggaggtg aaaactacgg      7740
atggggattc tggtatttat ggtcacgtta cttaccatat tgtaaatgac tttgccaaag    7800
acagatttta cataaatgag agaggacaga tatttacttt ggaaaaactt gatcgagaaa    7860
ccccggcgga gaaagtgatc tcagtccgtt taatggctaa ggatgctgga ggaaaagttg    7920
ctttctgcac cgtgaatgtc atccttacag atgacaatga caatgcacca caatttcgag    7980
caaccaaata cgaagtgaat atcgggtcca gtgctgctaa agggacttca gtcgttaaag    8040
ttcttgcaag tgatgccgat gagggctcca atgccgacat cacctatgcc attgaagcag    8100
actctgaaag tgtaaaagag aatttggaaa ttaacaaact gtccggcgta atcactacaa    8160
aggagagcct cattggcttg gaaaatgaat tcttcactttt cttgttaga gctgtggata     8220 atgggtctcc atcaaaagaa tctgttgttc ttgtctatgt taaaatcctt ccaccggaaa    8280
tgcagcttcc aaaattttca gaaccttttct ataccttttac agtgtcagag gacgtgccta    8340
ttggaacaga gatagatctc atccgagcag aacatagtgg gactgttctt tacagcctgg    8400
tcaaagggaa tactccagaa agcaataggg atgagtcctt tgtgattgac agacagagcg    8460
ggagactgaa gttggagaag agtcttgatc atgagacaac taagtggtat cagttttcca    8520
tactggccag gtgcactcaa gatgaccatg agatggtggc ttctgtagat gttagtatcc    8580
aagtgaaaga tgcaaatgac aacagcccgg tctttgaatc tagtccatat gaggcattca    8640
ttgttgaaaa cctgccaggg ggaagtagag taattcagat caaggcatct gatgctgact    8700
caggaaccaa cggccaagtt atgtatagcc tggatcagtac acaaagtgtg gaagtcattg    8760
aatcctttgc cattaacatg gaaacaggct ggattacaac tttaaaggaa cttgaccatg    8820
```

```
aaaagagaga caattaccag attaaagtgg ttgcatcaga tcatggtgaa aagatccagc    8880
tatcctccac agccattgtg gatgttaccg tcaccgatgt caacgatagt ccaccacgat    8940
tcacggccga gatctataaa gggactgtga gtgaggatga cccccaaggt ggggtgattg    9000
ccatcttaag taccacggat gctgattctg aagagatcaa cagacaagtt acatatttca    9060
taacaggagg ggatccttta ggacagtttg ccgttgaaac tatacagaat gaatggaagg    9120
tatatgtgaa gaaacctcta gacagggaaa aaagggacaa ttaccttctt actatcacgg    9180
caactgatgg caccttctca tcaaaagcga tagttgaagt gaaagttctg gatgcaaatg    9240
acaacagtcc agtttgtgaa aagactttat attcagacac tattcctgaa gacgtccttc    9300
ctggaaaatt gatcatgcag atctctgcta cagacgcaga catccgctct aacgctgaaa    9360
ttacttacac gttattgggt tcaggtgcag aaaaattcaa actaaatcca gacacaggtg    9420
aactgaaaac gtcaaccccc cttgatcgtg aggagcaagc tgtttatcat cttctcgtca    9480
gggccacaga tggaggagga agattctgcc aagccagtat tgtgctcacg ctagaagatg    9540
tgaacgataa cgccccgaa ttctctgccg atccttatgc catcaccgtg tttgaaaaca    9600
cagagccggg aacgctgctg acaagagtgc aggccacaga tgccgacgca ggattaaatc    9660
ggaagatttt atactcactg attgactctg ctgatgggca gttctccatt aacgaattat    9720
ctggaattat tcagttagaa aaaccttttgg acagagaact ccaggcagta tacaccctct    9780 cttttgaaagc tgtggatcaa ggcttgccaa ggaggctgac tgccactggc actgtgattg    9840
tatcagttct tgacataaat gacaacccccc ctgtgtttga gtaccgtgaa tatggtgcca    9900
ccgtgtctga ggacattctt gttggaactg aagttcttca agtgtatgca gcaagtcggg    9960
atattgaagc aaatgcagaa atcacctact caataataag tggaaatgaa catgggaaat   10020
tcagcataga ttctaaaaca ggggccgtat ttatcattga gaatctggat tatgagagct   10080
ctcatgagta ttacctaaca gtagaggcca ctgatgagg cacgccttca ctgagcgacg   10140
ttgccactgt gaacgttaat gtaacagata tcaacgataa taccccctgtg ttcagccaag   10200 acacctacac gacagtcatc agtgaagatg ccgttcttga gcagtctgtc atcacggtta   10260
tggccgatga tgccgatgga ccttccaaca gccacatcca ctactcaatt atagatggca   10320
accaaggaag ctcgttcaca attgaccccg tcagggggaga agtcaaagtg accaaacttc   10380
tcgaccgaga aacgatttca ggttacacgc tcacggttca agcttctgat aatggcagtc   10440
cacccagagt caaacgacg accgtgaaca tcgatgtgtc cgatgtcaat gacaacgcgc   10500
ccgtcttctc caggggaaac tacagtgtca ttatccagga aaataagcca gtgggcttca   10560
gcgtgctgca gctggtagta acagatgagg attcttccca taacggtcca cccttcttct   10620
ttactattgt aactggaaat gatgagaagg cttttgaagt taacccgcaa ggagtcctcc   10680
tgacatcatc tgccatcaag aggaaggaga aagatcatta cttactgcag gtgaaggtgg   10740
cagataatgg aaagcctcag ttgtcatctt tgacatacat tgacattagg gtaattgagg   10800
agagcatcta tccgcctgcg attttgcccc tggagatttt catcacctct tctggagaag   10860
aatactcagg tggcgtcatt gggaagatcc atgccacaga ccaggacgtg tatgatactc   10920
taacctacag tctcgaccct cagatggaca acctgttctc tgtttccagc acaggggggca   10980 agctgatagc acacaaaaag ctagacatag gcaatacct tctcaatgtc agcgtaacag   11040
atgggaagtt cacgacggtg gccgacatca cagtgcatat cagacaagtc acacaggaga   11100
tgttgaacca caccatcgcg atccgctttg ccaacctcac tccggaagaa ttcgttggtg   11160
actactggcg caacttccag cgagctttac ggaacatcct gggtgtgagg aggaacgaca   11220
```

```
tacagattgt tagtttgcag tcctctgaac ctcacccaca tctggacgtc ttacttttg    11280
tagagaaacc aggtagtgct cagatctcaa caaaacaact tctgcacaag attaactctt   11340
ccgtgactga cattgaggaa atcattggag ttaggatact gaatgtattc cagaaactct   11400
gcgcgggact ggactgcccc tggaagttct gcgatgaaaa ggtgtctgtg gatgaaagtg   11460
tgatgtcaac acacagcaca gccagactga gttttgtgac tccccgccac cacagggcag   11520
cggtgtgtct ctgcaaagag ggaaggtgcc cacctgtcca ccatggctgt gaagatgatc   11580
cgtgccctga gggatccgaa tgtgtgtctg atccctggga ggagaaacac acctgtgtct   11640
gtcccagcgg caggtttggt cagtgcccag ggagttcatc tatgacactg actggaaaca   11700
gctacgtgaa ataccgtctg acggaaaatg aaaacaaatt agagatgaaa ctgaccatga   11760
ggctcagaac atattccacg catgcggttg tcatgtatgc tcgaggaact gactatagca   11820
tcttggagat tcatcatgga aggctgcagt acaagtttga ctgtggaagt ggccctggaa   11880
ttgtctctgt tcagagcatt caggtcaatg atgggcagtg gcacgcagtg gccctggaag   11940
tgaatggaaa ctatgctcgc ttggttctag accaagttca tactgcatcg ggcacagccc   12000
cagggactct gaaaaccctg aacctggata actatgtgtt ttttggtggc cacatccgtc   12060
agcagggaac aaggcatgga agaagtcctc aagttggtaa tggtttcagg ggttgtatgg   12120
actccattta tttgaatggg caggagctcc ctttaaacag caaacccaga agctatgcac   12180
acatcgaaga gtcggtggat gtatctccag gctgcttcct gacggccacg gaagactgcg   12240
ccagcaaccc ttgccagaat ggaggcgttt gcaatccgtc acctgctgga ggttattact   12300
gcaaatgcag tgccttgtac atagggaccc actgtgagat aagcgtcaat ccgtgttcct   12360
ccaagccatg cctctatggg ggcacgtgtg ttgtcgacaa cggaggcttt gtttgccagt   12420
gtagaggatt atatactggt cagaggtgtc agcttagtcc atactgcaaa gatgaaccct   12480
gtaagaatgg cggaacatgc tttgacagtt tggatggcgc cgtttgtcag tgtgattcgg   12540
gttttagggg agaaaggtgt cagagtgata tcgacgagtg ctctggaaac ccttgcctgc   12600
acggggccct ctgtgagaac acgcacggct cctatcactg caactgcagc cacgagtaca   12660
ggggacgtca ctgcgaggat gctgcgccca accagtatgt gtccacgccg tggaacattg   12720
ggttggcgga aggaattgga atcgttgtgt ttgttgcagg gatattttta ctggtggtgg   12780
tgtttgttct ctgccgtaag atgattagtc ggaaaaagaa gcatcaggct gaacctaaag   12840
acaagcacct gggacccgct acggctttct tgcaaagacc gtattttgat tccaagctaa   12900
ataagaacat ttactcagac ataccacccc aggtgcctgt ccggcctatt tcctacaccc   12960
cgagtattcc aagtgactca agaaacaatc tggaccgaaa ttccttcgaa ggatctgcta   13020
tcccagagca tccccgaattc agcacttta accccgagtc tgtgcacggg caccgaaaag   13080
cagtggcggt ctgcagcgtg gcgccaaacc tgcctccccc accccttca aactccctt    13140
ctgacagcga ctccatccag aagcctagct gggactttga ctatgacaca aaagtggtgg   13200
atctgatcc ctgtctttcc aagaagcctt tagaggaaaa gccttccag ccatacagtg    13260
cccgggaaag cctgtctgaa gtgcagtctc tgagctcctt ccagtccgaa tcgtgcgatg   13320
acaatgggta tcactgggat acatcagatt ggatgccaag cgttcctctg ccggacatac   13380
aagagttccc caactatgag gtgattgatg agcagacacc cctgtactca gcagatccaa   13440
acgccatcga tacggactat taccctggag gctacgacat cgaaagtgat tttcctccac   13500
ccccagaaga cttccccgca gctgatgagc taccaccgtt accgcccgaa ttcagcaatc   13560
agtttgaatc catccaccct cctagagaca tgcctgccgc gggtagcttg ggttcttcat   13620
```

```
caagaaaccg gcagaggttc aacttgaatc agtatttgcc caattttat ccctcgata    13680 tgtctgaacc tcaaacaaaa ggcactggtg agaatagtac ttgtagagaa ccccatgccc    13740
cttacccgcc agggtatcaa agacacttcg aggcgcccgc tgtcgagagc atgcccatgt    13800
ctgtgtacgc ctccaccgcc tcctgctctg acgtgtcagc ctgctgcgaa gtggagtccg    13860
aggtcatgat gagtgactat gagagcgggg acgacggcca cttcgaagag gtgacgatcc    13920 cgccctgga ttcccagcag cacacggaag tctgactctc aactcccccc aaagtgcctg     13980
actttagtga acctagaggt gatgtgagta atccgcgctg ttctttgcag cagtgcttcc    14040 aagcttttt tggtgagccg aatgggcatg gctgcgctgg atcctgcgcc tctggacgtg      14100
ctagccattt ccagtgtccc aactactgtc atcgtgaggt tttcatcggc tgtgccattt     14160
cccaacgtct tttgggattt acatctgtct gtgttaaaat aatcaaacga aaaatcagtc    14220
ctgtgttgtc agcatgattc atgtatttat atagatttga ttattttaat tttcctgtct    14280
cttttttttg taaattttat gtacagattt gattttcat agttttaact agatttccaa     14340
gatattttgt gcatttgttt caactgaatt ttggtggtgt cagtgccatt atctagcacc    14400 ctgattttt tttttttact ataaccaggg tttcattctg tctttttcca ctgaagtgtg     14460 acatttgtt agtacatttc agtgtagtca ttcatttcta gctgtacata ggatgaagga    14520
gagatcagat acatgaacat gtcttacatg ggttgctgta tttagaatta taaacatttt    14580
tcattattgg aaagtgtaac ggggaccttc tgcatacctg tttagaacca aaaccaccat    14640
gacacagttt ttatagtgtc tgtatatttg tgatgcaatg gtcttgtaaa ggttttaat     14700 gaaaactacc attagccagt ctttcttact gacaataaat tattaataaa atacttgagc    14760
tttaaaaaaa aaa                                                       14773
```

<210> SEQ ID NO 33
<211> LENGTH: 6774
<212> TYPE: DNA
<213> ORGANISM: Homo sapiens

<400> SEQUENCE: 33

```
cggcccaga aaacccgagc gagtaggggg cggcgcgcag gagggaggag aactgggggc       60
gcgggaggct ggtgggtgtg gggggtggag atgtagaaga tgtgacgccg cggcccggcg     120
ggtgccagat tagcggacgc ggtgcccgcg gttgcaacgg gatcccgggc gctgcagctt    180
gggaggcggc tctccccagg cggcgtccgc ggagacaccc atccgtgaac cccaggtccc     240
gggccgccgg ctcgccgcgc accaggggcc ggcggacaga agagcggccg agcggctcga    300
ggctggggga ccgcgggcgc ggccgcgcgc tgccgggcgg gaggctgggg ggccggggcc   360
ggggccgtgc cccggagcgg gtcggaggcc ggggccgggg ccggggacg gcggctcccc    420 gcgcggctcc agcggctcgg ggatcccggc cgggccccgc agggaccatg gcagccggga    480
gcatcaccac gctgcccgcc ttgcccgagg atggcggcag cggcgccttc ccgcccggcc   540
acttcaagga ccccaagcgg ctgtactgca aaaacggggg cttcttcctg cgcatccacc   600
ccgacggccg agttgacggg gtccgggaga gagcgaccc tcacatcaag ctacaacttc    660
aagcagaaga gagaggagtt gtgtctatca aggagtgtg tgctaaccgt tacctggcta    720
tgaaggaaga tggaagatta ctggcttcta atgtgttac ggatgagtgt ttcttttttg     780
aacgattgga atctaataac tacaatactt accggtcaag gaaatacacc agttggtatg    840
tggcactgaa acgaactggg cagtataaac ttggatccaa aacaggacct gggcagaaag    900
ctatactttt tcttccaatg tctgctaaga gctgatttta atggccacat ctaatctcat   960
```

```
ttcacatgaa agaagaagta tattttagaa atttgttaat gagagtaaaa gaaaataaat    1020
gtgtatagct cagtttggat aattggtcaa acaattttt  atccagtagt aaaatatgta    1080
accattgtcc cagtaaagaa aaataacaaa agttgtaaaa tgtatattct ccctttata     1140 ttgcatctgc tgttacccag tgaagcttac ctagagcaat gatcttttc  acgcatttgc    1200 tttattcgaa aagaggcttt taaaatgtgc atgtttagaa acaaaatttc ttcatggaaa    1260
tcatatacat tagaaaatca cagtcagatg tttaatcaat ccaaaatgtc cactatttct    1320
tatgtcattc gttagtctac atgtttctaa acatataaat gtgaatttaa tcaattcctt    1380
tcatagtttt ataattctct ggcagttcct tatgatagag tttataaaac agtcctgtgt    1440
aaactgctgg aagttcttcc acagtcaggt caattttgtc aaaccttct  ctgtacccat    1500 acagcagcag cctagcaact ctgctggtga tgggagttgt attttcagtc ttcgccaggt    1560
cattgagatc catccactca catcttaagc attcttcctg gcaaaattt  atggtgaatg    1620 aatatgcctt taggcggcag atgatataca tatctgactt cccaaaagct ccaggatttg    1680
tgtgctgttg ccgaatactc aggacggacc tgaattctga ttttatacca gtctcttcaa    1740
aaacttctcg aaccgctgtg tctcctacgt aaaaaaagag atgtacaaat caataataat    1800 tacacttta  gaaactgtat catcaaagat tttcagttaa agtagcatta tgtaaaggct    1860
caaaacatta ccctaacaaa gtaaagtttt caatacaaat tctttgcctt gtggatatca    1920
agaaatccca aaatattttc ttaccactgt aaattcaaga agcttttgaa atgctgaata    1980 tttcttggc  tgctacttgg aggcttatct acctgtacat ttttggggtc agctcttttt    2040
aacttcttgc tgctctttt  cccaaaaggt aaaaatatag attgaaaagt taaaacattt    2100
tgcatggctg cagttccttt gtttcttgag ataagattcc aaagaactta gattcatttc    2160
ttcaacaccg aaatgctgga ggtgtttgat cagttttcaa gaaacttgga atataaataa    2220
ttttataatt caacaaaggt tttcacattt tataaggttg attttcaat  taaatgcaaa    2280 tttgtgtggc aggattttta ttgccattaa catatttttg tggctgcttt tctacacat     2340 ccagatggtc cctctaactg ggctttctct aattttgtga tgttctgtca ttgtctccca    2400
aagtatttag gagaagccct ttaaaaagct gccttcctct accactttgc tggaaagctt    2460
cacaattgtc acagacaaag atttttgttc caatactcgt tttgcctcta ttttcttgt     2520 ttgtcaaata gtaaatgata tttgcccttg cagtaattct actggtgaaa acatgcaaa     2580 gaagaggaag tcacagaaac atgtctcaat tcccatgtgc tgtgactgta gactgtctta    2640
ccatagactg tcttacccat cccctggata tgctcttgtt ttttccctct aatagctatg    2700
gaaagatgca tagaaagagt ataatgtttt aaaacataag gcattcgtct gccattttc     2760 aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940 tgaaacccccg tctctacaaa aaaacacaaa aaatagccag gcatggtggc gtgtacatgt   3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt ttccttaata agaaaagtaa ttttactct  gatgtgcaat    3180 acatttgtta ttaaatttat tatttaagat ggtagcacta gtcttaaatt gtataaaata    3240 tccccctaaca tgtttaaatg tccattttta ttcattatgc tttgaaaaat aattatgggg   3300
aaatacatgt ttgttattaa atttattatt aaagatagta gcactagtct taaatttgat    3360
```

```
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg gaagcaccgg atggggtag tgagcaaatc tgccctgctc    3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggatt caagatgaat    3720 tgaaattttt aatcaagata gtgtgcttta ttctgttgta ttttttatta ttttaatata   3780
ctgtaagcca aactgaaata acatttgctg ttttataggt ttgaagaaca taggaaaaac   3840
taagaggttt tgttttatt tttgctgatg aagagatatg tttaaatatg ttgtattgtt    3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgatttttt   4140
aagaaggcag tttgtcaatt ttaatcttgt ggataccttt atactcttag ggtattattt   4200
tatacaaaag ccttgaggat tgcattctat tttctatatg accctcttga tatttaaaaa   4260
acactatgga taacaattct tcatttacct agtattatga agaatgaag gagttcaaac    4320 aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
ttagaaatgc cttcatatag acatagtctt tcagacctct actgtcagtt tcatttcta    4560 gctgctttca gggttttatg aattttcagg caaagcttta atttatacta gcttaggaa    4620 gtatggctaa tgccaacggc agttttttt ttcttaattc cacatgactg aggcatatat    4680
gatctctggg taggtgagtt gttgtgacaa ccacaagcac tttttttttt tttaaagaaa   4740
aaaaggtagt gaattttaa tcatctggac tttaagaagg attctggagt atacttaggc    4800
ctgaaattat atatatttgg cttggaaatg tgttttttctt caattacatc tacaagtaag   4860
tacagctgaa attcagagga cccataagag ttcacatgaa aaaaatcaat ttatttgaaa   4920
aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
acaccactac aaaatcatct tttatatcaa cagaagaata agcataaact aagcaaaagg   5160
tcaataagta cctgaaacca agattggcta gagatatatc ttaatgcaat ccatttttctg  5220 atggattgtt acgagttggc tatataatgt atgtatggta ttttgatttg tgtaaaagtt   5280
ttaaaaatca agctttaagt acatggacat ttttaaataa atatttaaa gacaatttag    5340 aaaattgcct taatatcatt gttggctaaa tagaataggg gacatgcata ttaaggaaaa   5400
ggtcatggag aaataatatt ggtatcaaac aaatacattg atttgtcatg atacacattg   5460
aatttgatcc aatagtttaa ggaataggta ggaaatttg gtttctattt ttcgatttcc    5520
tgtaaatcag tgacataaat aattcttagc ttatttata tttccttgtc ttaaatactg    5580
agctcagtaa gttgtgttag gggattattt ctcagttgag actttcttat atgacatttt   5640
actatgtttt gacttcctga ctattaaaaa taaatagtag atacaatttt cataaagtga   5700
agaattatat aatcactgct ttataactga ctttattata tttatttcaa agttcattta   5760
```

| | |
|---|---|
| aaggctacta ttcatcctct gtgatggaat ggtcaggaat ttgttttctc atagtttaat | 5820 |
| tccaacaaca atattagtcg tatccaaaat aacctttaat gctaaacttt actgatgtat | 5880 |
| atccaaagct tctcattttc agacagatta atccagaagc agtcataaac agaagaatag | 5940 |
| gtggtatgtt cctaatgata ttatttctac taatggaata aactgtaata ttagaaatta | 6000 |
| tgctgctaat tatatcagct ctgaggtaat ttctgaaatg ttcagactca gtcggaacaa | 6060 |
| attggaaaat ttaaattttt attcttagct ataaagcaag aaagtaaaca cattaatttc | 6120 |
| ctcaacattt ttaagccaat taaaaatata aagatacac accatatct tcttcaggct | 6180 |
| ctgacaggcc tcctggaaac ttccacatat ttttcaactg cagtataaag tcagaaaata | 6240 |
| aagttaacat aactttcact aacacacaca tatgtagatt tcacaaaatc cacctataat | 6300 |
| tggtcaaagt ggttgagaat atatttttta gtaattgcat gcaaaatttt tctagcttcc | 6360 |
| atcctttctc cctcgtttct tctttttttg ggggagctgg taactgatga aatcttttcc | 6420 |
| caccttttct cttcaggaaa tataagtggt tttgtttggt taacgtgata cattctgtat | 6480 |
| gaatgaaaca ttggagggaa acatctactg aatttctgta atttaaaata ttttgctgct | 6540 |
| agttaactat gaacagatag aagaatctta cagatgctgc tataaataag tagaaaatat | 6600 |
| aaatttcatc actaaaatat gctattttaa aatctatttc ctatattgta tttctaatca | 6660 |
| gatgtattac tcttattatt tctattgtat gtgttaatga tttatgtaa aaatgtaatt | 6720 |
| gcttttcatg agtagtatga ataaaattga ttagtttgtg ttttcttgtc tccc | 6774 |

<210> SEQ ID NO 34
<211> LENGTH: 2838
<212> TYPE: DNA
<213> ORGANISM: Homo sapiens

<400> SEQUENCE: 34

| | |
|---|---|
| gggcgcagag ctgggccgag ccgtcgccgg cgccacgcga gtcccgcagc cgccgcgccc | 60 |
| gggcaatggg ccgggggcac tgagggccgc cggggccgag cgcggagggg ggaccgagcc | 120 |
| agtgccgtgc cctcgggccg cgccaacatg ccccgcggct tcctggtgaa gcgcagcaag | 180 |
| aagtccacgc ccgtttccta ccgggtccgc ggcggcgagg acggcgaccg cgcactgctg | 240 |
| ctctcgccca gctgcggggg cgcccgcgcc gagcccccgg cgccgagccc ggtcccgggg | 300 |
| ccgctgccgc cgccgccgcc cgcggagcgc gcccatgcag cgctcgccgc cgcgcttgcc | 360 |
| tgcgcgcctg ggccgcagcc accccgcag ggcccgcggg ccgcgcactt cggcaacccc | 420 |
| gaggctgcgc accccgcgcc gctctacagt cccacgcggc ccgtgagccg cgagcacgag | 480 |
| aagcacaagt acttcgaacg cagcttcaac ctgggctcgc cggtctcggc cgagtccttc | 540 |
| cccacgcccg ccgcgctgct cggaggggc ggcggcggcg gcgcgagcgg agctggcgga | 600 |
| ggcggcacct gcggcggcga cccgctgctc ttcgcgcccg ccgagctcaa gatgggcacg | 660 |
| gcgttctcgg ctggcgccga gcggccccgc ggcccgggcc ccggcccccc actgccccct | 720 |
| gccgccgccc tgcggccccc gggaaagcgc ccccgccccc ctaccgccgc ggagccgccc | 780 |
| gccaaggcag tcaaggcccc gggcgccaag aagcccaagg ccatccgcaa gctgcacttc | 840 |
| gaggacgagg tgaccacgtc gcccgtgctg gggctcaaga tcaaggaggg cccggtggag | 900 |
| gcgccgcggg ccgcgcggg gggcgcggcg cggccgctgg gcgagttcat ctgccagctg | 960 |
| tgcaaggagg agtacgccga cccgttcgcg ctggcgcagc acaaatgctc gcgcatcgtg | 1020 |
| cgtgtggagt accgctgtcc cgagtgcgcc aaggtcttca gctgcccggc caacctggcc | 1080 |
| tcgcaccgcc gctggcacaa accgcggccc gcgcccgccg ccgcccgcgc gccggagcca | 1140 |

-continued

| | |
|---|---|
| gaagcagcag ccagggctga ggcgcgggag gcacccggcg gcggcagcga ccgggacacg | 1200 |
| ccgagcccg gcggcgtgtc cgagtcgggc tccgaggacg ggctctacga gtgccatcac | 1260 |
| tgcgccaaga agttccgccg ccaggcctac ctacgcaagc acctgctggc gcaccaccag | 1320 |
| gcgctgcagg ccaagggcgc gccgctagcg cccccggccg aggacctact ggccttgtac | 1380 |
| cccgggcccg acgagaaggc gccccaggag gcggccggcg acggcgaggg ggccggcgtg | 1440 |
| ctgggcctga gtgcgtccgc cgagtgccac ctgtgcccag tgtgcggaga gtcgttcgcc | 1500 |
| agcaagggcg ctcaggagcg ccacctgcgc ctgctgcacg ccgcccaggt gttcccctgc | 1560 |
| aagtactgcc cggccacctt ctacagctcg cccggcctta cgcggcacat caacaagtgc | 1620 |
| cacccatccg aaaacagaca ggtgatcctc ctgcaggtgc ccgtgcgccc ggcctgctag | 1680 |
| agcgcgccct ccaccccggc ccccgaactg tgccttcgct tggagaccca caaagagagt | 1740 |
| gcgccctgca cgccccgaac ccgagtccgc gctgggggag cctcgccccc gcccccaccg | 1800 |
| ggtgaaagtg tcgtctccgc ttctctcggt gtggcgtgac ggtaacccca tactctcctt | 1860 |
| ttgactcctt ttggaacccc cacttttacg ttgtgtccct ccgcctcccc catggcgcaa | 1920 |
| caggagtcag tctcttttctg tacaagggag aaaagctgta cgcgtttgtc tcgtggttgg | 1980 |
| aagcctcccc ttggcgggga gaagcttttt ttcttgctag tattcgctgt gttcatggtc | 2040 |
| tagaaatgcg gtctggtctc gcctcgccta ccaatctctg ctctctatgt atgtagcgta | 2100 |
| cgggttgttt tgggtgaatc ttgaggaata aatgccttta tatttcacag gctgtaaatt | 2160 |
| gaacttccca cacgattagc tttattatgg cttgtgaact gctggagtct ggctttacct | 2220 |
| ttttgtatgt gaacaaatca aattgcttaa aaaagagttt tctttagtat agccacaaat | 2280 |
| gccttgaact gttgtctggg attgttttgt gggggggaggg aagggagtgt tccgaagatg | 2340 |
| ctgtagtaac tgcctcagtg tttcacgtaa gacttttggg tttgatcatc tttgttgagg | 2400 |
| taggactatc agttccctct aaatgtatat gttgatttat gagtaattgt tatttattct | 2460 |
| ttatttattt atattaatta tgaagattat gatattattt gattgcagat tttttttggcg | 2520 |
| cgctgccccc tccccacccct gccactcttg acattccact gtgcgtttta aagagagcc | 2580 |
| tttttctaaa gggatctgct taaagtttta acttttatac ctatctgagt gaattacaga | 2640 |
| caacctatca tttattctgc ttcgagggtc cccagggccc ttgtacaacc gacagctctt | 2700 |
| acttttaaat gcaatctctt ttctacatac attattttct taattgttag ctatttatag | 2760 |
| aaagcttcaa tagaactgtt tcaactgtat aactatttac tattcaaata aaatattttc | 2820 |
| aaagtcaaaa aaaaaaaa | 2838 |

<210> SEQ ID NO 35
<211> LENGTH: 2900
<212> TYPE: DNA
<213> ORGANISM: Homo sapiens

<400> SEQUENCE: 35

| | |
|---|---|
| gcccggcagg ttggcggacc ggcgggaggc gcagcctggg cagagctcag cttggtcccg | 60 |
| ccgcccggcc ggtgctccct ggcgcagcca cgcaggcgca ccgcagacag accccctctgc | 120 |
| catgaaccag tccatcccag tggctcccac cccaccccgc cgcgtgcggc tgaagccctg | 180 |
| gctggtggcc caggtgaaca gctgccagta cccaggcctt caatgggtca acggggaaaa | 240 |
| gaaattattc tgcatcccct ggaggcatgc cacaaggcat ggtcccagcc aggacggaga | 300 |
| taacaccatc ttcaaggcct gggccaagga gacagggaaa tacaccgaag gcgtggatga | 360 |
| agccgatccg gccaagtgga aggccaacct gcgctgtgcc cttaacaaga gccgggactt | 420 |

```
ccgcctcatc tacgacgggc cccgggacat gccacctcag ccctacaaga tctacgaggt    480
ctgctccaat ggccctgctc ccacagactc ccagcccct gaggattact cttttggtgc     540
aggagaggag gaggaagaag aggaagagct gcagaggatg ttgccaagcc tgagcctcac   600
agatgcagtg cagtctggcc cccacatgac accctattct ttactcaaag aggatgtcaa   660
gtggccgccc actctgcagc cgcccactct gcggccgcct actctgcagc cgcccactct   720
gcagccgccc gtggtgctgg gtcccctgc tccagacccc agcccctgg ctcctccccc     780 tggcaaccct gctggcttca gggagcttct ctctgaggtc ctggagcctg gcccctgcc    840 tgccagcctg ccccctgcag gcgaacagct cctgccagac ctgctgatca gccccacat    900 gctgcctctg accgacctgg agatcaagtt tcagtaccgg gggcggccac cccgggccct   960
caccatcagc aaccccatg gctgccggct cttctacagc cagctggagg ccacccagga   1020
gcaggtggaa ctcttcggcc ccataagcct ggagcaagtg cgcttcccca gccctgagga   1080 catcccagt gacaagcagc gcttctacac gaaccagctg ctggatgtcc tggaccgcgg    1140
gctcatcctc cagctacagg gccaggacct ttatgccatc cgcctgtgtc agtgcaaggt   1200
gttctggagc gggccttgtg cctcagccca tgactcatgc cccaacccca tccagcggga   1260
ggtcaagacc aagctttcca gcctggagca ttttctcaat gagctcatcc tgttccaaaa   1320
gggccagacc aacaccccac cacccttcga gatcttcttc tgctttgggg aagaatggcc   1380
tgaccgcaaa ccccgagaga agaagctcat tactgtacag gtggtgcctg tagcagctcg   1440
actgctgctg gagatgttct caggggagct atcttggtca gctgatagta tccggctaca   1500
gatctcaaac ccagacctca agaccgcat ggtggagcaa ttcaaggagc tccatcacat    1560
ctggcagtcc cagcagcggt tgcagcctgt ggcccaggcc cctcctggag caggccttgg   1620
tgttggccag gggccctggc ctatgcaccc agctggcatg caataacaag gctgcagacg   1680
gtgactggcc ctggcttcct gggtggcggt gcggactgat gtggagatgt gacagccccg   1740
atgagcacct ggctggctgc agggtcctac ctctgggttt cctggaagtg gatttgggcc   1800
aagaaggaga gggagaaagg cccgagcccc tgccttcccg ggcctttctc tcctgggctg   1860
tctctggtct ggtcagcctg gctctcggga aattcagcca tgagcaggga agaactctc    1920 ccaaccctgg ggcctagctg tataggagga attgcctaag ggtggcccac tcttgtgatt   1980
gccccatttc ctctggcaac aaaagccaga gtgttgtggg ccaagtcccc ccacagggcc   2040
tctgcagggc atggccctga tttccctggt ttgagactca cttcctcatc tccctgtcct   2100
ctgagataat atgagtgagc acttaggtat catatcagat gctcaaggct ggcagctacc   2160
cccttcttga gagtccaaga acctggagca gaaataattt ttatgtattt ttggattaat   2220
gaatgttaaa aacagactca gctgtttctt tccttttact actaccagtt gctcccatgc   2280
tgctccacca ggccctgttt cggatgccaa ctggcccact ccccaagcac ttgccccag    2340 cttgcgacca ttggcactgg gagggcctgg cttctgggct gatgggtcag ttgggccttc   2400
ataaacactc acctggctgg ctttgccttc caggaggaag ctggctgaag caagggtgtg   2460
gaattttaaa tgtgtgcaca gtctggaaaa ctgtcagaat cagttttccc ataaaagggt   2520
gggctagcat tgcagctgca tttgggacca ttcaaatctg tcactctctt gtgtatattc   2580
ctgtgctatt aaatatatca gggcagtgca tgtaaatcat cctgatatat ttaatatatt   2640
tattatattg tccccgagg tggggacagt gagtgagttc tcttagtccc cccagagctg    2700
gttgttaaag agcctggcac ctacccgctc tcacttcatc tgtgtcatct ctgcacactc   2760
cagcccactt tctgccttca gccattgagt ggaagctgcc ccaggccctt accaggtgca   2820
```

```
gatgcccaat cttgatgccc agccatcaga actgtgagcc aaataaacct ttttctgtat    2880
aaaaaaaaaa aaaaaaaaaa                                                2900
```

<210> SEQ ID NO 36
<211> LENGTH: 2870
<212> TYPE: DNA
<213> ORGANISM: Homo sapiens

<400> SEQUENCE: 36

```
gcccggcagg ttggcggacc ggcgggaggc gcagcctggg cagagctcag cttggtcccg      60
ccgcccggcc ggtgctccct ggcgcagcca cgcaggcgca ccgcagacag acccctctgc     120
catgaaccag tccatcccag tggctcccac cccaccccgc cgcgtgcggc tgaagccctg     180
gctggtggcc caggtgaaca gctgccagta cccagggctt caatgggtca acggggaaaa     240
gaaattattc tgcatcccct ggaggcatgc cacaaggcat ggtcccagcc aggacggaga     300
taacaccatc ttcaaggcct gggccaagga gacagggaaa tacaccgaag cgtggatga      360
agccgatccg gccaagtgga aggccaacct gcgctgtgcc cttaacaaga gccgggactt     420
ccgcctcatc tacgacgggc cccgggacat gccacctcag ccctacaaga tctacgaggt     480
ctgctccaat ggccctgctc ccacagactc ccagccccct gaggattact cttttggtgc     540
aggagaggag gaggaagaag aggaagagct gcagaggatg ttgccaagcc tgagcctcac     600
agatgcagtg cagtctggcc cccacatgac accctattct ttactcaaag aggatgtcaa     660
gtggccgcct actctgcagc cgcccactct gcagccgccc gtggtgctgg gtccccctgc     720
tccagacccc agcccctgg ctcctccccc tggcaaccct gctggcttca gggagcttct     780
ctctgaggtc ctggagcctg gcccctgcc tgccagcctg cccctgcag gcgaacagct     840
cctgccagac tgctgatca gccccacat gctgcctctg accgacctgg agatcaagtt     900
tcagtaccgg gggcggccac cccgggccct caccatcagc aaccccatg gctgccggct     960
cttctacagc cagctggagg ccacccagga gcaggtggaa ctcttcggcc ccataagcct    1020
ggagcaagtg cgcttcccca gccctgagga catccccagt gacaagcagc gcttctacac    1080
gaaccagctg ctggatgtcc tggaccgcgg gctcatcctc cagctacagg ccaggacct     1140
ttatgccatc cgcctgtgtc agtgcaaggt gttctggagc gggccttgtg cctcagccca    1200
tgactcatgc cccaacccca tccagcggga ggtcaagacc aagcttttca gcctggagca    1260
ttttctcaat gagctcatcc tgttccaaaa gggccagacc aacaccccac cacccttcga    1320
gatcttcttc tgctttgggg aagaatggcc tgaccgcaaa cccgagaga agaagctcat     1380
tactgtacag gtggtgcctg tagcagctcg actgctgctg gagatgttct caggggagct    1440
atcttggtca gctgatagta tccggctaca gatctcaaac ccagacctca aagaccgcat    1500
ggtggagcaa ttcaaggagc tccatcacat ctggcagtcc cagcagcggt tgcagcctgt    1560
ggcccaggcc cctcctggag caggccttgg tgttggccag gggccctggc ctatgcaccc    1620
agctggcatg caataacaag gctgcagacg gtgactggcc ctggcttcct gggtggcggt    1680
gcggactgat gtggagatgt gacagcccg atgagcacct ggctggctgc agggtcctac    1740
ctctgggttt cctggaagtg gatttggggcc aagaaggaga gggagaaagg cccgagcccc    1800
tgccttcccg ggcctttctc tcctgggctg tctctggtct ggtcagcctg gctctcggga    1860
aattcagcca tgagcaggga aagaactctc ccaaccctgg ggcctagctg tataggagga    1920
attgcctaag ggtggcccac tcttgtgatt gcccatttc ctctggcaac aaaagccaga    1980
gtgttgtggg ccaagtcccc ccacagggcc tctgcagggc atggccctga tttccctggt    2040
```

```
ttgagactca cttcctcatc tccctgtcct ctgagataat atgagtgagc acttaggtat    2100
catatcagat gctcaaggct ggcagctacc cccttcttga gagtccaaga acctggagca    2160
gaaataattt ttatgtattt ttggattaat gaatgttaaa aacagactca gctgtttctt    2220
tccttttact actaccagtt gctcccatgc tgctccacca ggccctgttt cggatgccaa    2280 ctggccccact ccccaagcac ttgccccag cttgcgacca ttggcactgg gagggcctgg    2340
cttctgggct gatgggtcag ttgggccttc ataaacactc acctggctgg ctttgccttc    2400
caggaggaag ctggctgaag caagggtgtg gaattttaaa tgtgtgcaca gtctggaaaa    2460
ctgtcagaat cagttttccc ataaaagggt gggctagcat tgcagctgca tttgggacca    2520
ttcaaatctg tcactctctt gtgtatattc ctgtgctatt aaatatatca gggcagtgca    2580
tgtaaatcat cctgatatat ttaatatatt tattatattg tcccccgagg tggggacagt    2640
gagtgagttc tcttagtccc cccagagctg gttgttaaag agcctggcac ctacccgctc    2700
tcacttcatc tgtgtcatct ctgcacactc cagcccactt tctgccttca gccattgagt    2760
ggaagctgcc ccaggccctt accaggtgca gatgcccaat cttgatgccc agccatcaga    2820
actgtgagcc aaataaacct ttttctgtat aaaaaaaaaa aaaaaaaaaa              2870

<210> SEQ ID NO 37
<211> LENGTH: 2870
<212> TYPE: DNA
<213> ORGANISM: Homo sapiens

<400> SEQUENCE: 37
gagcgttctg aacacctccc cgtcccagcc cctgggccag gcaagggccg gccttacctc      60
tcctgggttg gtggcagcag agctgggctc tgagggaggc ctgcaatgtg agacagtagc     120
agctcagagg cggcactagg caggtgcaac cccaaaagac ccctctgcca tgaaccagtc     180
catcccagtg gctcccaccc caccccgccg cgtgcggctg aagccctggc tggtggccca     240
ggtgaacagc tgccagtacc cagggcttca atgggtcaac ggggaaaaga aattattctg     300
catcccctgg aggcatgcca caaggcatgg tcccagccag gacggagata acaccatctt     360
caaggcctgg gccaaggaga cagggaaata caccgaaggc gtggatgaag ccgatccggc     420
caagtggaag gccaacctgc gctgtgccct taacaagagc cgggacttcc gcctcatcta     480
cgacgggccc cgggacatgc cacctcagcc ctacaagatc tacgaggtct gctccaatgg     540
ccctgctccc acagactccc agcccccctga ggattactct tttggtgcag agaggagga     600 ggaagaagag gaagagctgc agaggatgtt gccaagcctg agcctcacag aggatgtcaa     660
gtggccgccc actctgcagc cgcccactct gcagccgccc gtggtgctgg gtccccctgc     720
tccagacccc agcccccctgg ctcctccccc tggcaaccct gctggcttca gggagcttct     780
ctctgaggtc ctggagcctg gcccctgcc tgccagcctg cccctgcag gcgaacagct     840 cctgccagac ctgctgatca gccccacat gctgcctctg accgacctgg agatcaagtt     900
tcagtaccgg gggcggccac cccgggccct caccatcagc aaccccccatg gctgccggct     960 cttctacagc cagctggagg ccacccagga gcaggtggaa ctcttcggcc ccataagcct    1020
ggagcaagtg cgcttcccca gccctgagga catcccagt gacaagcagc gcttctacac    1080
gaaccagctg ctggatgtcc tggaccgcgg gctcatcctc cagctacagg gccaggacct    1140
ttatgccatc cgcctgtgtc agtgcaaggt gttctggagc gggccttgtg cctcagccca    1200
tgactcatgc cccaacccca tccagcggga ggtcaagacc aagcttttca gcctggagca    1260
ttttctcaat gagctcatcc tgttccaaaa gggccagacc aacacccac caccccttcga    1320
```

| | |
|---|---|
| gatcttcttc tgctttgggg aagaatggcc tgaccgcaaa ccccgagaga agaagctcat | 1380 |
| tactgtacag gtggtgcctg tagcagctcg actgctgctg gagatgttct caggggagct | 1440 |
| atcttggtca gctgatagta tccggctaca gatctcaaac ccagacctca aagaccgcat | 1500 |
| ggtggagcaa ttcaaggagc tccatcacat ctggcagtcc cagcagcggt tgcagcctgt | 1560 |
| ggcccaggcc cctcctggag caggccttgg tgttggccag gggccctggc ctatgcaccc | 1620 |
| agctggcatg caataacaag gctgcagacg gtgactggcc ctggcttcct gggtggcggt | 1680 |
| gcggactgat gtggagatgt gacagccccg atgagcacct ggctggctgc agggtcctac | 1740 |
| ctctgggttt cctggaagtg gatttgggcc aagaaggaga gggagaaagg cccgagcccc | 1800 |
| tgccttcccg ggccttttctc tcctgggctg tctctggtct ggtcagcctg gctctcggga | 1860 |
| aattcagcca tgagcaggga aagaactctc ccaaccctgg ggcctagctg tataggagga | 1920 |
| attgcctaag ggtggcccac tcttgtgatt gccccatttc ctctggcaac aaaagccaga | 1980 |
| gtgttgtggg ccaagtcccc ccacagggcc tctgcagggc atggccctga tttccctggt | 2040 |
| ttgagactca cttcctcatc tccctgtcct ctgagataat atgagtgagc acttaggtat | 2100 |
| catatcagat gctcaaggct ggcagctacc cccttcttga gagtccaaga acctggagca | 2160 |
| gaaataattt ttatgtattt ttggattaat gaatgttaaa aacagactca gctgtttctt | 2220 |
| tccttttact actaccagtt gctcccatgc tgctccacca ggccctgttt cggatgccaa | 2280 |
| ctggcccact ccccaagcac ttgccccag cttgcgacca ttggcactgg gagggcctgg | 2340 |
| cttctgggct gatgggtcag ttgggccttc ataaacactc acctggctgg ctttgccttc | 2400 |
| caggaggaag ctggctgaag caagggtgtg gaattttaaa tgtgtgcaca gtctggaaaa | 2460 |
| ctgtcagaat cagttttccc ataaaagggt gggctagcat tgcagctgca tttgggacca | 2520 |
| ttcaaatctg tcactctctt gtgtatattc ctgtgctatt aaatatatca gggcagtgca | 2580 |
| tgtaaatcat cctgatatat ttaatatatt tattatattg tccccgagg tggggacagt | 2640 |
| gagtgagttc tcttagtccc cccagagctg gttgttaaag agcctggcac ctacccgctc | 2700 |
| tcacttcatc tgtgtcatct ctgcacactc cagcccactt tctgccttca gccattgagt | 2760 |
| ggaagctgcc ccaggccctt accaggtgca gatgcccaat cttgatgccc agccatcaga | 2820 |
| actgtgagcc aaataaacct ttttctgtat aaaaaaaaa aaaaaaaaa | 2870 |

<210> SEQ ID NO 38
<211> LENGTH: 2852
<212> TYPE: DNA
<213> ORGANISM: Homo sapiens

<400> SEQUENCE: 38

| | |
|---|---|
| gcccggcagg ttggcggacc ggcgggaggc gcagcctggg cagagctcag cttggtcccg | 60 |
| ccgcccggcc ggtgctccct ggcgcagcca cgcaggcgca ccgcagacag acccctctgc | 120 |
| catgaaccag tccatcccag tggctcccac cccacccccgc cgcgtgcggc tgaagccctg | 180 |
| gctggtggcc caggtgaaca gctgccagta cccagggctt caatgggtca acggggaaaa | 240 |
| gaaattattc tgcatcccct ggaggcatgc cacaaggcat ggtccagcc aggacggaga | 300 |
| taacaccatc ttcaaggcct gggccaagga gacaggaaa tacaccgaag gcgtggatga | 360 |
| agccgatccg gccaagtgga aggccaacct gcgctgtgcc cttaacaaga gcgggactt | 420 |
| ccgcctcatc tacgcgggc cccgggacat gccaccctcag ccctacaaga tctacgaggt | 480 |
| ctgctccaat ggccctgctc ccacagactc ccagccccct gaggattact cttttggtgc | 540 |
| aggagaggag gaggaagaag aggaagagct gcagaggatg ttgccaagcc tgagcctcac | 600 |

```
agaggatgtc aagtggccgc ccactctgca gccgcccact ctgcggccgc ctactctgca    660
gccgcccact ctgcagccgc cgtggtgct gggtccccct gctccagacc ccagcccct    720 ggctcctccc cctggcaacc ctgctggctt cagggagctt ctctctgagg tcctggagcc    780
tgggcccctg cctgccagcc tgcccctgc aggcgaacag ctcctgccag acctgctgat    840 cagccccac atgctgcctc tgaccgacct ggagatcaag tttcagtacc ggggcggcc    900 accccgggcc ctcaccatca gcaacccca tggctgccgg ctcttctaca gccagctgga    960
ggccacccag gagcaggtgg aactcttcgg ccccataagc ctggagcaag tgcgcttccc   1020
cagccctgag gacatcccca gtgacaagca gcgcttctac acgaaccagc tgctggatgt   1080
cctggaccgc gggctcatcc tccagctaca gggccaggac ctttatgcca tccgcctgtg   1140
tcagtgcaag gtgttctgga gcgggccttg tgcctcagcc catgactcat gccccaaccc   1200
catccagcgg gaggtcaaga ccaagctttt cagcctggag cattttctca atgagctcat   1260
cctgttccaa aagggccaga ccaacacccc accacccttc gagatcttct tctgctttgg   1320
ggaagaatgg cctgaccgca aaccccgaga agaagctc attactgtac aggtggtgcc   1380
tgtagcagct cgactgctgc tggagatgtt ctcaggggag ctatcttggt cagctgatag   1440
tatccggcta cagatctcaa acccagacct caaagaccgc atggtggagc aattcaagga   1500
gctccatcac atctggcagt cccagcagcg gttgcagcct gtggcccagg ccctcctgg   1560 agcaggcctt ggtgttggcc aggggccctg gcctatgcac ccagctggca tgcaataaca   1620
aggctgcaga cggtgactgg ccctggcttc tgggtggcg gtgcggactg atgtggagat   1680
gtgacagccc cgatgagcac ctggctggct gcagggtcct acctctgggt ttcctggaag   1740
tggatttggg ccaagaagga gagggagaaa ggcccgagcc cctgccttcc cgggcctttc   1800
tctcctgggc tgtctctggt ctggtcagcc tggctctcgg gaaattcagc catgagcagg   1860
gaaagaactc tcccaaccct ggggcctagc tgtataggag gaattgccta agggtggccc   1920
actcttgtga ttgccccatt tcctctggca acaaaagcca gagtgttgtg ggccaagtcc   1980
ccccacaggg cctctgcagg gcatggccct gatttccctg gtttgagact cacttcctca   2040
tctccctgtc ctctgagata atatgagtga gcacttaggt atcatatcag atgctcaagg   2100
ctggcagcta cccccttctt gagagtccaa gaacctggag cagaaataat ttttatgtat   2160
ttttggatta atgaatgtta aaacagact cagctgtttc tttccttta ctactaccag   2220 ttgctcccat gctgctccac caggcccgt ttcggatgcc aactggccca ctccccaagc   2280
acttgccccc agcttgcgac cattggcact gggagggcct ggcttctggg ctgatgggtc   2340
agttgggcct tcataaacac tcacctggct ggctttgcct tccaggagga agctggctga   2400
agcaagggtg tggaattta atgtgtgca cagtctggaa aactgtcaga atcagttttc   2460
ccataaaagg gtgggctagc attgcagctg catttgggac cattcaaatc tgtcactctc   2520
ttgtgtatat tcctgtgcta ttaaatatat cagggcagtg catgtaaatc atcctgatat   2580
atttaatata tttattatat tgtcccccga ggtggggaca gtgagtgagt tctcttagtc   2640
cccccagagc tggttgttaa agagcctggc acctacccgc tctcacttca tctgtgtcat   2700
ctctgcacac tccagcccac tttctgcctt cagccattga gtggaagctg ccccaggccc   2760
ttaccaggtg cagatgccca atcttgatgc ccagccatca gaactgtgag ccaaataaac   2820 cttttttctgt ataaaaaaaa aaaaaaaaaa aa                                2852
```

<210> SEQ ID NO 39
<211> LENGTH: 2822

<212> TYPE: DNA
<213> ORGANISM: Homo sapiens

<400> SEQUENCE: 39

```
gcccggcagg ttggcggacc ggcgggaggc gcagcctggg cagagctcag cttggtcccg        60
ccgcccggcc ggtgctccct ggcgcagcca cgcaggcgca ccgcagacag acccctctgc       120
catgaaccag tccatcccag tggctcccac cccacccccgc cgcgtgcggc tgaagccctg      180
gctggtggcc caggtgaaca gctgccagta cccagggctt caatgggtca acggggaaaa      240
gaaattattc tgcatcccct ggaggcatgc cacaaggcat ggtcccagcc aggacggaga      300
taacaccatc ttcaaggcct gggccaagga gacagggaaa tacaccgaag gcgtggatga      360
agccgatccg gccaagtgga aggccaacct gcgctgtgcc cttaacaaga gccgggactt      420
ccgcctcatc tacgacgggc cccgggacat gccacctcag ccctcaaga tctacgaggt       480
ctgctccaat ggccctgctc ccacagactc ccagcccccct gaggattact cttttggtgc     540
aggagaggag gaggaagaag aggaagagct gcagaggatt ttgccaagcc tgagcctcac      600
agaggatgtc aagtggccgc ccactctgca gccgcccact ctgcagccgc ccgtggtgct     660
gggtccccct gctccagacc ccagcccccct ggctcctccc cctggcaacc ctgctggctt    720
cagggagctt ctctctgagg tcctggagcc tgggcccctg cctgccagcc tgccccctgc      780
aggcgaacag ctcctgccag acctgctgat cagcccccac atgctgcctc tgaccgacct      840
ggagatcaag tttcagtacc gggggcggcc accccgggcc ctcaccatca gcaaccccca     900
tggctgccgg ctcttctaca gccagctgga ggccacccag gagcaggtgg aactcttcgg     960
ccccataagc ctggagcaag tgcgcttccc cagccctgag gacatcccca gtgacaagca     1020
gcgcttctac acgaaccagc tgctggatgt cctggaccgc gggctcatcc tccagctaca    1080
gggccaggac cttatgcca tccgcctgtg tcagtgcaag gtgttctgga gcgggccttg    1140
tgcctcagcc catgactcat gccccaaccc catccagcgg gaggtcaaga ccaagctttt    1200
cagcctggag cattttctca atgagctcat cctgttccaa aagggccaga ccaacacccc     1260
accacccttc gagatcttct tctgctttgg ggaagaatgg cctgaccgca aaccccgaga     1320
gaagaagctc attactgtac aggtggtgcc tgtagcagct cgactgctgc tggagatgtt     1380
ctcaggggag ctatcttggt cagctgatag tatccggcta cagatctcaa acccagacct     1440
caaagaccgc atggtggagc aattcaagga gctccatcac atctggcagt cccagcagcg     1500
gttgcagcct gtggcccagg cccctcctgg agcaggcctt ggtgttggcc aggggccctg    1560
gcctatgcac ccagctggca tgcaataaca aggctgcaga cggtgactgg ccctggcttc     1620
ctgggtggcg gtgcggactg atgtggagat gtgacagccc cgatgagcac ctggctggct     1680
gcagggtcct acctctgggt ttcctggaag tggatttggg ccaagaagga gagggagaaa    1740
ggcccgagcc cctgccttcc cgggccttc tctcctgggc tgtctctggt ctggtcagcc     1800
tggctctcgg gaaattcagc catgagcagg gaaagaactc tcccaaccct ggggcctagc    1860
tgtataggag gaattgccta agggtggccc actcttgtga ttgccccatt tcctctggca    1920
acaaaagcca gagtgttgtg ggccaagtcc ccccacaggg cctctgcagg gcatggcct     1980
gatttccctg gtttgagact cacttcctca tctccctgtc ctctgagata atatgagtga    2040
gcacttaggt atcatatcag atgctcaagg ctggcagcta ccccttctt gagagtccaa      2100
gaacctggag cagaaataat ttttatgtat ttttggatta atgaatgtta aaaacagact    2160
cagctgtttc tttcctttta ctactaccag ttgctcccat gctgctccac caggccctgt    2220
ttcggatgcc aactggccca ctccccaagc acttgccccc agcttgcgac cattggcact   2280
```

```
gggagggcct ggcttctggg ctgatgggtc agttgggcct tcataaacac tcacctggct    2340
ggctttgcct tccaggagga agctggctga agcaagggtg tggaatttta aatgtgtgca    2400
cagtctggaa aactgtcaga atcagttttc ccataaaagg gtgggctagc attgcagctg    2460
catttgggac cattcaaatc tgtcactctc ttgtgtatat tcctgtgcta ttaaatatat    2520
cagggcagtg catgtaaatc atcctgatat atttaatata tttattatat tgtcccccga    2580
ggtggggaca gtgagtgagt tctcttagtc cccccagagc tggttgttaa agagcctggc    2640
acctacccgc tctcacttca tctgtgtcat ctctgcacac tccagcccac tttctgcctt    2700
cagccattga gtggaagctg ccccaggccc ttaccaggtg cagatgccca atcttgatgc    2760
ccagccatca gaactgtgag ccaaataaac ctttttctgt ataaaaaaaa aaaaaaaaa     2820 aa                                                                  2822

<210> SEQ ID NO 40
<211> LENGTH: 2771
<212> TYPE: DNA
<213> ORGANISM: Homo sapiens

<400> SEQUENCE: 40
gtccagctgc gcctggaaag cgagctcgga cccctctgcc atgaaccagt ccatcccagt      60
ggctcccacc ccaccccgcc gcgtgcggct gaagccctgg ctggtggccc aggtgaacag    120
ctgccagtac ccagggcttc aatgggtcaa cggggaaaag aaattattct gcatcccctg    180
gaggcatgcc acaaggcatg gtcccagcca ggacggagat aacaccatct tcaaggcctg    240
ggccaaggag acagggaaat acaccgaagg cgtggatgaa gccgatccgg ccaagtggaa    300
ggccaacctg cgctgtgccc ttaacaagag ccgggacttc cgcctcatct acgacgggcc    360
ccgggacatg ccacctcagc cctacaagat ctacgaggtc tgctccaatg ccctgctcc     420 cacagactcc cagccccctg aggattactc ttttggtgca ggagaggagg aggaagaaga    480
ggaagagctg cagaggatgt tgccaagcct gagcctcaca gaggatgtca agtggccgcc    540
cactctgcag ccgcccactc tgcggccgcc tactctgcag ccgcccactc tgcagccgcc    600
cgtggtgctg ggtccccctg ctccagaccc cagccccctg gctcctcccc ctggcaaccc    660
tgctggcttc agggagcttc tctctgaggt cctggagcct gggcccctgc ctgccagcct    720 gcccctgca ggcgaacagc tcctgccaga cctgctgatc agccccccaca tgctgcctct    780 gaccgacctg gagatcaagt ttcagtaccg ggggcggcca ccccgggccc tcaccatcag    840 caaccccat ggctgccggc tcttctacag ccagctggag gccacccagg agcaggtgga    900
actcttcggc cccataagcc tggagcaagt gcgcttcccc agccctgagg acatccccag    960
tgacaagcag cgcttctaca cgaaccagct gctggatgtc ctggaccgcg ggctcatcct    1020
ccagctacag ggccaggacc tttatgccat ccgcctgtgt cagtgcaagg tgttctggag    1080
cgggccttgt gcctcagccc atgactcatg ccccaacccc atccagcggg aggtcaagac    1140
caagcttttc agcctggagc attttctcaa tgagctcatc ctgttccaaa agggccagac    1200
caacacccca ccacccttcg agatcttctt ctgctttggg gaagaatggc ctgaccgcaa    1260 acccgagag aagaagctca ttactgtaca ggtggtgcct gtagcagctc gactgctgct    1320
ggagatgttc tcaggggagc tatcttggtc agctgatagt atccggctac agatctcaaa    1380
cccagacctc aaagaccgca tggtggagca attcaaggag ctccatcaca tctggcagtc    1440
ccagcagcgc ttgcagcctg tggcccaggc ccctcctgga gcaggccttg gtgttggcca    1500
ggggccctgg cctatgcacc cagctggcat gcaataacaa ggctgcagac ggtgactggc    1560
```

| | |
|---|---|
| cctggcttcc tgggtggcgg tgcggactga tgtggagatg tgacagcccc gatgagcacc | 1620 |
| tggctggctg cagggtccta cctctgggtt tcctggaagt ggatttgggc caagaaggag | 1680 |
| agggagaaag gcccgagccc ctgccttccc gggccttct ctcctgggct gtctctggtc | 1740 |
| tggtcagcct ggctctcggg aaattcagcc atgagcaggg aaagaactct cccaaccctg | 1800 |
| gggcctagct gtataggagg aattgcctaa gggtggccca ctcttgtgat tgccccattt | 1860 |
| cctctggcaa caaaagccag agtgttgtgg gccaagtccc cccacagggc ctctgcaggg | 1920 |
| catggccctg atttccctgg tttgagactc acttcctcat ctccctgtcc tctgagataa | 1980 |
| tatgagtgag cacttaggta tcatatcaga tgctcaaggc tggcagctac ccccttcttg | 2040 |
| agagtccaag aacctggagc agaaataatt tttatgtatt tttggattaa tgaatgttaa | 2100 |
| aaacagactc agctgtttct ttcctttttac tactaccagt tgctcccatg ctgctccacc | 2160 |
| aggccctgtt tcggatgcca actggcccac tccccaagca cttgccccca gcttgcgacc | 2220 |
| attggcactg gagggcctg gcttctgggc tgatgggtca gttgggcctt cataaacact | 2280 |
| cacctggctg gctttgcctt ccaggaggaa gctggctgaa gcaagggtgt ggaattttaa | 2340 |
| atgtgtgcac agtctggaaa actgtcagaa tcagttttcc cataaagggg tgggctagca | 2400 |
| ttgcagctgc atttgggacc attcaaatct gtcactctct tgtgtatatt cctgtgctat | 2460 |
| taaatatatc agggcagtgc atgtaaatca tcctgatata tttaatatat ttattatatt | 2520 |
| gtcccccgag gtggggacag tgagtgagtt ctcttagtcc ccccagagct ggttgttaaa | 2580 |
| gagcctggca cctacccgct ctcacttcat ctgtgtcatc tctgcacact ccagcccact | 2640 |
| ttctgccttc agccattgag tggaagctgc cccaggccct taccaggtgc agatgcccaa | 2700 |
| tcttgatgcc cagccatcag aactgtgagc caaataaacc tttttctgta taaaaaaaaa | 2760 |
| aaaaaaaaaa a | 2771 |

<210> SEQ ID NO 41
<211> LENGTH: 2741
<212> TYPE: DNA
<213> ORGANISM: Homo sapiens

<400> SEQUENCE: 41

| | |
|---|---|
| gtccagctgc gcctggaaag cgagctcgga cccctctgcc atgaaccagt ccatcccagt | 60 |
| ggctcccacc ccaccccgcc gcgtgcggct gaagccctgg ctggtggccc aggtgaacag | 120 |
| ctgccagtac ccagggcttc aatgggtcaa cggggaaaag aaattattct gcatcccctg | 180 |
| gaggcatgcc acaaggcatg gtcccagcca ggacggagat aacaccatct tcaaggcctg | 240 |
| ggccaaggag acagggaaat acaccgaagg cgtggatgaa gccgatccgg ccaagtggaa | 300 |
| ggccaacctg cgctgtgccc ttaacaagag ccgggacttc cgcctcatct acgacgggcc | 360 |
| ccgggacatg ccacctcagc cctacaagat ctacgaggtc tgctccaatg ccctgctcc | 420 |
| cacagactcc cagcccctg aggattactc ttttggtgca ggagaggagg aggaagaaga | 480 |
| ggaagagctg cagaggatgt tgccaagcct gagcctcaca gaggatgtca agtggccgcc | 540 |
| cactctgcag ccgccactc tgcagccgcc cgtggtgctg gtcccctg ctccagaccc | 600 |
| cagcccctg gctcctcccc ctggcaaccc tgctggcttc agggagcttc tctctgaggt | 660 |
| cctggagcct gggcccctgc ctgccagcct gccccctgca ggcgaacagc tcctgccaga | 720 |
| cctgctgatc agcccccaca tgctgcctct gaccgacctg gagatcaagt ttcagtaccg | 780 |
| ggggcggcca cccggggccc tcaccatcag caaccccat ggctgccggc tcttctacag | 840 |
| ccagctggag gccacccagg agcaggtgga actcttcggc cccataagcc tggagcaagt | 900 |

```
gcgcttcccc agccctgagg acatcccag tgacaagcag cgcttctaca cgaaccagct    960
gctggatgtc ctggaccgcg ggctcatcct ccagctacag ggccaggacc tttatgccat   1020
ccgcctgtgt cagtgcaagg tgttctggag cgggccttgt gcctcagccc atgactcatg   1080
ccccaacccc atccagcggg aggtcaagac caagcttttc agcctggagc attttctcaa   1140
tgagctcatc ctgttccaaa agggccagac caacaccca ccaccttcg agatcttctt    1200
ctgctttggg gaagaatggc ctgaccgcaa accccgagag aagaagctca ttactgtaca   1260
ggtggtgcct gtagcagctc gactgctgct ggagatgttc tcaggggagc tatcttggtc   1320
agctgatagt atccggctac agatctcaaa cccagacctc aaagaccgca tggtggagca   1380
attcaaggag ctccatcaca tctggcagtc ccagcagcgg ttgcagcctg tggcccaggc   1440
ccctcctgga gcaggccttg tgttggcca ggggccctgg cctatgcacc cagctggcat    1500
gcaataacaa ggctgcagac ggtgactggc cctggcttcc tgggtggcgg tgcggactga   1560
tgtggagatg tgacagcccc gatgagcacc tggctggctg cagggtccta cctctgggtt   1620
tcctggaagt ggatttgggc caagaaggag agggagaaag gcccgagccc ctgccttccc   1680
gggccttttct ctcctgggct gtctctggtc tggtcagcct ggctctcggg aaattcagcc   1740
atgagcaggg aaagaactct cccaaccctg gggcctagct gtataggagg aattgcctaa   1800
gggtggccca ctcttgtgat tgccccattt cctctggcaa caaaagccag agtgttgtgg   1860
gccaagtccc cccacagggc ctctgcaggg catggccctg atttccctgg tttgagactc   1920
acttcctcat ctccctgtcc tctgagataa tatgagtgag cacttaggta tcatatcaga   1980
tgctcaaggc tggcagctac ccccttcttg agagtccaag aacctggagc agaaataatt   2040
tttatgtatt tttggattaa tgaatgttaa aaacagactc agctgtttct ttcctttac    2100
tactaccagt tgctcccatg ctgctccacc aggccctgtt tcggatgcca actggcccac   2160
tccccaagca cttgccccca gcttgcgacc attggcactg ggagggcctg gcttctgggc   2220
tgatgggtca gttgggcctt cataaacact cacctggctg gctttgcctt ccaggaggaa   2280
gctggctgaa gcaagggtgt ggaattttaa atgtgtgcac agtctggaaa actgtcagaa   2340
tcagttttcc cataaaaggg tgggctagca ttgcagctgc atttgggacc attcaaatct   2400
gtcactctct tgtgtatatt cctgtgctat taaatatatc agggcagtgc atgtaaatca   2460
tcctgatata tttaatatat ttattatatt gtccccgag gtggggacag tgagtgagtt    2520
ctcttagtcc cccagagct ggttgttaaa gagcctggca cctacccgct ctcacttcat    2580
ctgtgtcatc tctgcacact ccagcccact ttctgccttc agccattgag tggaagctgc   2640
cccaggccct taccaggtgc agatgcccaa tcttgatgcc cagccatcag aactgtgagc   2700
caaataaacc tttttctgta taaaaaaaaa aaaaaaaaa a                        2741

<210> SEQ ID NO 42
<211> LENGTH: 2770
<212> TYPE: DNA
<213> ORGANISM: Homo sapiens

<400> SEQUENCE: 42
gttgggcggg gcagggagtt cgtagccgcc tctgggtaac tcgactcggg cggccaaacc     60
tccgaggcc ggggacggaa ggcgggcccg cagcagatcc tggatccgga atctcccggg     120
caggagcgga atctgtcccg aaccgggtct gtgaggaact cgcgaacttg gattaggaaa    180
tcccggagcc cggatcgaca aatcccggaa cccggaatta agatcgccaa gtcccggatc    240
gcggagcaca gagcacggag tggactcgac gcggagcccg gagtccggat cgcggcaccg    300
```

```
cgggacggga cggagcgatg tcgggccgag gcgcgggcgg gttcccgctg cccccgctaa    360
gccctggcgg cggcgccgtg gctgcggccc tgggagcgcc gcctcccccc gcgggacccg    420
gcatgctgcc cggaccggcg ctccggggac cgggtccggc aggaggcgtg gggggccccg    480
gggccgccgc cttccgcccc atgggccccg cgggccccgc ggcgcagtac cagcgacctg    540
gcatgtcacc agggaaccgg atgcccatgg ctggcttgca ggtggacccc cctgctggct    600
ccccatttgg tgcagcagct ccgcttcgac ctggcatgcc acccaccatg atggatccat    660
tccgaaaacg cctgcttgtg ccccaggcgc agcctcccat gcctgcccag cgccgggggt    720
taaagaggag gaagatggca gataaggttc tacctcagcg aatccgggag cttgttccag    780
agtctcaggc gtacatggat ctcttggctt ttgagcggaa gctggaccag accattgctc    840
gcaagcggat ggagatccag gaggccatca aaaagcctct gacacaaaag cgaaagcttc    900
ggatctacat ttccaatacg ttcagtccca gcaaggcgga aggcgatagt gcaggaactg    960
cagggacccc tggggaacc ccagcagggg acaaggtggc ttcctgggaa ctccgagtgg   1020
aaggaaaact gctggatgat cctagcaaac agaagaggaa gttttcttca ttctttaaga   1080
gcctcgtcat tgagctggac aaggagctgt acgggcctga caatcacctg gtggagtggc   1140
accggatgcc caccacccag gagacagatg gcttccaagt aaaacggcct ggagacctca   1200
acgtcaagtg caccctcctg ctcatgctgg atcatcagcc tccccagtac aaattggacc   1260
cccgattggc aaggctgctg ggagtgcaca cgcagacgag ggccgccatc atgcaggccc   1320
tgtggcttta catcaagcac aaccagctgc aggatgggca cgagcgggag tacatcaact   1380
gcaaccgtta cttccgccag atcttcagtt gtggccgact ccgtttctcc gagattccca   1440
tgaagctggc agggttgctg cagcatccag accccattgt catcaaccat gtcattagtg   1500
tcgaccctaa cgaccagaag aagacagcct gttacgacat cgatgtggag gtggacgacc   1560
cactgaaggc ccaaatgagc aattttctgg cctctaccac caatcagcag gagatcgcct   1620
cccttgatgt caagatccat gagaccattg agtccatcaa ccagctgaag acccagagag   1680
atttcatgct cagttttagc accgaccccc aggacttcat ccaggaatgg ctccgttccc   1740
agcgccgaga cctcaagatc atcactgatg tgattggaaa tcctgaggag gagagacgag   1800
ctgctttcta ccaccagccc tgggcccagg aagcagtagg caggcacatc tttgccaagg   1860
tgcagcagcg aaggcaggaa ctggaacagg tgctgggaat tcgcctgacc taactgctca   1920
gggatctttc ttcccagccc tggagcctgg agggagacca ccctctgggt ccttgctggg   1980
gccgcagaca cgtaggctgg ggtgaggagt gtctgctgtc accctctact ctccagcttt   2040
agtcttataa atgtagtgat aggattcctt gttgcttggt ccccaaagcc ttatactttt   2100
tgcattggct ttaattgggt tcagcagatg cctcctctgc cccctgcag gcaggcccaa    2160 gtaggactgc tggaggctgt gctttgacat tgtaagacat ttccgaacca aaggctgctg   2220
ggtttgcatg tttacagact cccctggggg cgagggtcag agctggctct ggggagctgg   2280
gctaggaaga ggaggtgcag cccagactct tcctagcctt tctaaaccaa agttctttgc   2340
cattcctaca agcccagcct tgctgctggt tttttccttt cctttgggta tttgcactat   2400
tttgggagca agttttctat gtgggagcca cttttttgt acaggggtaa gttgggggtt   2460
ttcagggagc ctgttaggtg cctccttctt ttctttcctc aatctatgca agcggctctg   2520
gccgccatca tctcctggga tgccagaggg ctgcctctcc agcggcttgg gccggggagg   2580
ggacactcca gttctctagc atggcctgag gtatggggta tgtgcatgtg gaggccaggg   2640
taaggtgaat ggggaggctg ggaggactgg tgttgcccct tggagcttgg tgaggagggt   2700
```

```
gggcctaggg cttggcgagt gccacatctg gcaggtttgg aaatttccaa ataaatcctt    2760
ttgtctattg                                                          2770

<210> SEQ ID NO 43
<211> LENGTH: 2707
<212> TYPE: DNA
<213> ORGANISM: Homo sapiens

<400> SEQUENCE: 43
gttgggcggg gcagggagtt cgtagccgcc tctgggtaac tcgactcggg cggccaaacc     60
tccggaggcc ggggacggaa ggcgggcccg cagcagatcc tggatccgga atctcccggg    120
caggagcgga atctgtcccg aaccgggtct gtgaggaact cgcgaacttg gattaggaaa    180
tcccggagcc cggatcgaca aatcccggaa cccggaatta agatcgccaa gtcccggatc    240
gcggagcaca gagcacggag tggactcgac gcggagcccg gagtccggat cgcggcaccg    300
cgggacggga cggagcgatg tcgggccgag gcgcgggcgg gttcccgctg cccccgctaa    360
gccctggcgg cggcgccgtg gctgcggccc tgggagcgcc gcctcccccc gcgggacccg    420
gcatgctgcc cggaccggcg ctccggggac cgggtccggc gcagtaccag cgacctggca    480
tgtcaccagg gaaccggatg cccatggctg gcttgcaggt gggaccccct gctggctccc    540
catttggtgc agcagctccg cttcgacctg gcatgccacc caccatgatg gatccattcc    600
gaaaacgcct gcttgtgccc caggcgcagc ctcccatgcc tgcccagcgc cggggggttaa    660 agaggaggaa gatggcagat aaggttctac ctcagcgaat ccgggagctt gttccagagt    720
ctcaggcgta catggatctc ttggcttttg agcggaagct ggaccagacc attgctcgca    780
agcggatgga gatccaggag gccatcaaaa agcctctgac acaaaagcga agcttcgga     840 tctacatttc caatacgttc agtcccagca aggcggaagg cgatagtgca ggaactgcag    900
ggacccctgg gggaaccccca gcaggggaca aggtggcttc ctgggaactc cgagtggaag    960
gaaaactgct ggatgatcct agcaaacaga agaggaagtt ttcttcattc tttaagagcc   1020
tcgtcattga gctggacaag gagctgtacg ggcctgacaa tcacctggtg gagtggcacc   1080
ggatgcccac cacccaggag acagatggct tccaagtaaa acggcctgga gacctcaacg   1140
tcaagtgcac cctcctgctc atgctggatc atcagcctcc ccagtacaaa ttggaccccc   1200
gattggcaag gctgctggga gtgcacacgc agacgagggc cgccatcatg caggccctgt   1260
ggctttacat caagcacaac cagctgcagg atgggcacga gcgggagtac atcaactgca   1320
accgttactt ccgccagatc ttcagttgtg gccgactccg tttctccgag attcccatga   1380
agctggcagg gttgctgcag catccagacc ccattgtcat caaccatgtc attagtgtcg   1440
accctaacga ccagaagaag acagcctgtt acgacatcga tgtggaggtg gacgacccac   1500
tgaaggccca aatgagcaat tttctggcct ctaccaccaa tcagcaggag atcgcctccc   1560
ttgatgtcaa gatccatgag accattgagt ccatcaacca gctgaagacc agagagatt    1620 tcatgctcag ttttagcacc gaccccccagg acttcatcca ggaatggctc cgttcccagc   1680
gccgagacct caagatcatc actgatgtga ttggaaatcc tgaggaggag agacgagctg   1740 cttctctacca ccagccctgg gcccaggaag cagtaggcag gcacatctttt gccaaggtgc   1800 agcagcgaag gcaggaactg gaacaggtgc tgggaattcg cctgacctaa ctgctcaggg   1860
atctttcttc ccagccctgg agctggagg gagaccaccc tctgggtcct gctggggcc    1920 gcagacacgt aggctggggt gaggagtgtc tgctgtcacc ctctactctc cagctttagt   1980
cttataaatg tagtgatagg attccttgtt gcttggtccc caaagcctta acttttttgc   2040
```

```
attggcttta attgggttca gcagatgcct cctctgcccc cctgcaggca ggcccaagta   2100
ggactgctgg aggctgtgct ttgacattgt aagacatttc cgaaccaaag gctgctgggt   2160
ttgcatgttt acagactccc cctggggcga gggtcagagc tggctctggg gagctgggct   2220
aggaagagga ggtgcagccc agactcttcc tagcctttct aaaccaaagt tctttgccat   2280
tcctacaagc ccagccttgc tgctggtttt tccttttcct ttgggtattt gcactatttt   2340
gggagcaagt tttctatgtg ggagccactt tttttgtaca ggggtaagtt gggggttttc   2400
agggagcctg ttaggtgcct ccttcttttc tttcctcaat ctatgcaagc ggctctggcc   2460
gccatcatct cctgggatgc cagagggctg cctctccagc ggcttgggcc ggggagggga   2520
cactccagtt ctctagcatg gcctgaggta tggggtatgt gcatgtggag gccagggtaa   2580
ggtgaatggg gaggctggga ggactggtgt tgcccttggg agcttggtga ggagggtggg   2640
cctagggctt ggcgagtgcc acatctggca ggtttggaaa tttccaaata aatccttttg   2700
tctattg                                                            2707

<210> SEQ ID NO 44
<211> LENGTH: 1759
<212> TYPE: DNA
<213> ORGANISM: Homo sapiens

<400> SEQUENCE: 44
cccctgcctc tcggactcgg gctgcggcgt cagccttctt cgggcctcgg cagcggtagc     60
ggctcgctcg cctcagcccc agcgcccctc ggctaccctc ggcccaggcc cgcagcgccg    120
cccgccctcg gccgccccga cgccggcctg ggccgcggcc gcagcccggg gctcgcgtag    180
gcgccgaccg ctcccggccc gcccctatg gccccggct agaggcgccg ccgccgccgg     240
cccgcggagc cccgatgctg gccggagga agccggtgct gccggcgctc accatcaacc    300
ctaccatcgc cgagggccca tcccctacca gcgagggcgc ctccgaggca aacctggtgg    360
acctgcagaa gaagctggag gagctggaac ttgacgagca gcagaagaag cggctggaag    420
cctttctcac ccagaaagcc aaggtcgcg aactcaaaga cgatgacttc gaaaggatct    480
cagagctggg cgcgggcaac ggcggggtgg tcaccaaagt ccagcacaga ccctcgggcc    540
tcatcatggc caggaagctg atccaccttg agatcaagcc ggccatccgg aaccagatca    600
tccgcgagct gcaggtcctg cacgaatgca actcgccgta catcgtgggc ttctacgggg    660
ccttctacag tgacggggag atcagcattt gcatggaaca catggacggc ggctcccctg    720
accaggtgct gaaagaggcc aagaggattc ccgaggagat cctggggaaa gtcagcatcg    780
cggttctccg gggcttggcg tacctccgag agaagcacca gatcatgcac cgagatgtga    840 agcccctccaa catcctcgtg aactctagag gggagatcaa gctgtgtgac ttcggggtga    900
gcggccagct catagactcc atggccaact ccttcgtggg cacgcgctcc tacatggctc    960
cggagcggtt gcagggcaca cattactcgg tgcagtcgga catctggagc atgggcctgt   1020
ccctggtgga gctggccgtc ggaaggtacc ccatcccccc gccgacgcc aaagagctgg    1080 aggccatctt tggccggccc gtggtcgacg gggaagaagg agagcctcac agcatctcgc   1140
ctcggccgag gccccgggg cgccccgtca gcggtcacgg gatggatagc ggcctgcca    1200 tggccatctt tgaactcctg gactatattg tgaacgagcc acctcctaag ctgcccaacg   1260
gtgtgttcac ccccgacttc caggagtttg tcaataaatg cctcatcaag aacccagcgg   1320
agcgggcgga cctgaagatg ctcacaaacc acaccttcat caagcggtcc gaggtggaag   1380
aagtggattt tgccggctgg ttgtgtaaaa ccctgcggct gaaccagccc ggcacaccca   1440
```

-continued

```
cgcgcaccgc cgtgtgacag tggccgggct ccctgcgtcc cgctggtgac ctgcccaccg    1500
tccctgtcca tgccccgccc ttccagctga ggacaggctg gcgcctccac ccaccctcct    1560
gcctcacccc tgcggagagc accgtggcgg ggcgacagcg catgcaggaa cgggggtctc    1620
ctctcctgcc cgtcctggcc ggggtgcctc tggggacggg cgacgctgct gtgtgtggtc    1680
tcagaggctc tgcttccttq ggttacaaaa caaaacaggg agagaaaaag caaaaaaaaa    1740
aaaaaaaaaa aaaaaaaa                                                   1759
```